United States Patent
Cai et al.

(10) Patent No.: US 12,162,874 B2
(45) Date of Patent: Dec. 10, 2024

(54) PEPTIDOMIMETIC-BASED ANTIBODY SURROGATE FOR HER2

(71) Applicant: University of South Florida, Tampa, FL (US)

(72) Inventors: Jianfeng Cai, Tampa, FL (US); Mengmeng Zheng, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 33 days.

(21) Appl. No.: 17/705,208

(22) Filed: Mar. 25, 2022

(65) Prior Publication Data
US 2022/0332833 A1    Oct. 20, 2022

Related U.S. Application Data

(60) Provisional application No. 63/200,820, filed on Mar. 30, 2021.

(51) Int. Cl.
| | |
|---|---|
| *C07D 417/06* | (2006.01) |
| *A61K 47/54* | (2017.01) |
| *B01L 3/00* | (2006.01) |
| *B01L 9/00* | (2006.01) |
| *C07D 311/44* | (2006.01) |
| *C07D 317/46* | (2006.01) |
| *C07K 16/28* | (2006.01) |
| *C07K 16/30* | (2006.01) |

(52) U.S. Cl.
CPC .......... *C07D 417/06* (2013.01); *A61K 47/545* (2017.08); *B01L 3/50273* (2013.01); *B01L 9/527* (2013.01); *C07D 311/44* (2013.01); *C07D 317/46* (2013.01); *C07K 16/2863* (2013.01); *C07K 16/3015* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2020/0276199 A1    9/2020    Buggy et al.

OTHER PUBLICATIONS

Sporn et al. ("Proliferative Diseases" The American Journal of Medicine, vol. 70 (6), Jun. 1981, pp. 1231-1236).*
cancer.gov (https://www.cancer.gov/about-cancer/understanding/what-is-cancer accessed Nov. 30, 2023).*
Cancer Research UK (https://www.cancerresearchuk.org/about-cancer/treatment/drugs/trastuzumab accessed Nov. 30, 2023).*
Hynes, N. E.; Lane, H. A., ERBB receptors and cancer: the complexity of targeted inhibitors. Nat. Rev. Cancer 2005, 5 (5), 341-354.
Petrelli, F.; Tomasello, G.; Barni, S.; Lonati, V.; Passalacqua, R.; Ghidini, M., Clinical and pathological characterization of HER2 mutations in human breast cancer: a systematic review of the literature. Breast Cancer Res. Tr. 2017, 166 (2), 339-349.
King, C.; Kraus, M.; Aaronson, S., Amplification of a novel v-erbB-related gene in a human mammary carcinoma. Science 1985, 229 (4717), 974-976.
Arteaga, Carlos L.; Engelman, Jeffrey A., ERBB Receptors: From Oncogene Discovery to Basic Science to Mechanism-Based Cancer Therapeutics. Cancer Cell 2014, 25 (3), 282-303.
Burstein, H. J., The Distinctive Nature of HER2-Positive Breast Cancers. N. Engl. J. Med. 2005, 353 (16), 1652-1654.
Vogel, C. L.; Cobleigh, M. A.; Tripathy, D.; Gutheil, J. C.; Harris, L. N.; Fehrenbacher, L.; Slamon, D. J.; Murphy, M.; Novotny, W. F.; Burchmore, M.; Shak, S.; Stewart, S. J.; Press, M., Efficacy and Safety of Trastuzumab as a Single Agent in First-Line Treatment of HER2-Overexpressing Metastatic Breast Cancer. J. Clin. Oncol. 2002, 20 (3), 719-726.
Capelan, M.; Pugliano, L.; De Azambuja, E.; Bozovic, I.; Saini, K. S.; Sotiriou, C.; Loi, S.; Piccart-Gebhart, M. J., Pertuzumab: new hope for patients with HER2-positive breast cancer. Ann. Oncol. 2012, 24 (2), 273-282.
Moy, B.; Goss, P. E., Lapatinib: Current Status and Future Directions in Breast Cancer. Oncol. 2006, 11 (10), 1047-1057.
Chan, A., Neratinib in HER-2-positive breast cancer: results to date and clinical usefulness. Ther. Adv. Med. Oncol. 2016, 8 (5), 339-350.
Garrett, J. T.; Arteaga, C. L., Resistance to HER2-directed antibodies and tyrosine kinase inhibitors. Cancer Bio. Ther. 2011, 11 (9), 793-800.
Ku, Z.-q.; Zhang, Y.; Li, N.; Liu, P.-j.; Gao, L.; Gao, X.; Tie, X.-j., Efficacy and safety of lapatinib and trastuzumab for HER2-positive breast cancer: a systematic review and meta-analysis of randomised controlled trials. BMJ Open 2017, 7 (3), e013053.
Scheuer, W.; Friess, T.; Burtscher, H.; Bossenmaier, B.; Endl, J.; Hasmann, M., Strongly Enhanced Antitumor Activity of Trastuzumab and Pertuzumab Combination Treatment on HER2-Positive Human Xenograft Tumor Models. Cancer Res. 2009, 69 (24), 9330-9336.
Baselga, et al., Pertuzumab plus Trastuzumab plus Docetaxel for Metastatic Breast Cancer. N. Engl. J. Med. 2011, 366 (2), 109-119.
Swain, S. M.; Baselga, J.; Kim, S.-B.; Ro, J.; Semiglazov, V.; Campone, M.; Ciruelos, E.; Ferrero, J.-M.; Schneeweiss, A.; Heeson, S.; Clark, E.; Ross, G.; Benyunes, M. C.; Cortés, J., Pertuzumab, Trastuzumab, and Docetaxel in HER2-Positive Metastatic Breast Cancer. N. Engl. J. Med. 2015, 372 (8), 724-734.
Shi, Y.; Teng, P.; Sang, P.; She, F.; Wei, L.; Cai, J., γ-AApeptides: Design, Structure, and Applications. Acc. Chem. Res 2016, 49 (3), 428-441.
Teng, P.; Shi, Y.; Sang, P.; Cai, J., γ-AApeptides as a New Class of Peptidomimetics. Chem. Eur. J. 2016, 22 (16), 5458-5466.

(Continued)

*Primary Examiner* — Jeanette M Lieb
*Assistant Examiner* — Tara L Martinez
(74) *Attorney, Agent, or Firm* — Quarles & Brady LLP

(57) ABSTRACT

Disclosed are cyclic γ-amino acid peptide compounds, methods of using said compounds, and kits comprising said compounds. More specifically, disclosed are human epidermal growth factor receptor 2 (HER2) specific cyclic γ-amino acid peptide compounds, methods of using said compounds in the treatment of cell proliferative diseases or disorders, methods of detecting HER2 using the compounds, and kits comprising the compounds.

29 Claims, 52 Drawing Sheets
Specification includes a Sequence Listing.

(56) References Cited

OTHER PUBLICATIONS

Teng, P.; Ma, N.; Cerrato, D. C.; She, F.; Odom, T.; Wang, X.; Ming, L.-J.; van der Vaart, A.; Wojtas, L.; Xu, H.; Cai, J., Right-Handed Helical Foldamers Consisting of De Novo d-AApeptides. J. Am. Chem. Soc. 2017, 139 (21), 7363-7369.
She, F.; Teng, P.; Peguero-Tejada, A.; Wang, M.; Ma, N.; Odom, T.; Zhou, M.; Gjonaj, E.; Wojtas, L.; van der Vaart, A.; Cai, J., De Novo Left-Handed Synthetic Peptidomimetic Foldamers. Angew. Chem. Int. Ed. 2018, 57 (31), 9916-9920.
Teng, P.; Niu, Z.; She, F.; Zhou, M.; Sang, P.; Gray, G. M.; Verma, G.; Wojtas, L.; van der Vaart, A.; Ma, S.; Cai, J., Hydrogen-Bonding-Driven 3D Supramolecular Assembly of Peptidomimetic Zipper. J. Am. Chem. Soc. 2018, 140 (17), 5661-5665.
Teng, P.; Gray, G. M.; Zheng, M.; Singh, S.; Li, X.; Wojtas, L.; van der Vaart, A.; Cai, J., Orthogonal Halogen- Bonding-Driven 3D Supramolecular Assembly of Right-Handed Synthetic Helical Peptides. Angew. Chem. Int. Ed. 2019, 58 (23), 7778-7782.
Sang, P.; Zhang, M.; Shi, Y.; Li, C.; Abdulkadir, S.; Li, Q.; Ji, H.; Cai, J., Inhibition of β-catenin/B cell lymphoma 9 protein-protein interaction using α-helix-mimicking sulfono-γ-AApeptide inhibitors. Proc. Natl. Acad. Sci. U. S. A. 2019, 116 (22), 10757-10762.
Shi, Y.; Challa, S.; Sang, P.; She, F.; Li, C.; Gray, G. M.; Nimmagadda, A.; Teng, P.; Odom, T.; Wang, Y.; van der Vaart, A.; Li, Q.; Cai, J., One-Bead-Two-Compound Thioether Bridged Macrocyclic γ-AApeptide Screening Library against EphA2. J. Med. Chem. 2017, 60 (22), 9290-9298.
Shi, Y.; Parag, S.; Patel, R.; Lui, A.; Murr, M.; Cai, J.; Patel, N. A., Stabilization of lncRNA GAS5 by a Small Molecule and Its Implications in Diabetic Adipocytes. Cell Chem. Bio. 2019, 26 (3), 319-330.e6.
Yan, H.; Zhou, M.; Bhattarai, U.; Song, Y.; Zheng, M.; Cai, J.; Liang, F.-S., Cyclic Peptidomimetics as Inhibitor for miR-155 Biogenesis. Mol. Pharm. 2019, 16 (2), 914-920.
Handl, H. L.; Sankaranarayanan, R.; Josan, J. S.; Vagner, J.; Mash, E. A.; Gillies, R. J.; Hruby, V. J., Synthesis and Evaluation of Bivalent NDP-α-MSH(7) Peptide Ligands for Binding to the Human Melanocortin Receptor 4 (hMC4R). Bioconjugate Chemistry 2007, 18 (4), 1101-1109.
Udugamasooriya, D. G.; Dineen, S. P.; Brekken, R. A.; Kodadek, T., A Peptoid "Antibody Surrogate" That Antagonizes VEGF Receptor 2 Activity. J. Am. Chem. Soc. 2008, 130 (17), 5744-5752.
Kodadek, T., Development of antibody surrogates for the treatment of cancers and autoimmune disease. Curr. Opin. Chem. Bio. 2010, 14 (6), 721-727.
Sarkar, M.; Liu, Y.; Morimoto, J.; Peng, H.; Aquino, C.; Rader, C.; Chiorazzi, N.; Kodadek, T., Recognition of Antigen-Specific B-Cell Receptors from Chronic Lymphocytic Leukemia Patients by Synthetic Antigen Surrogates. Chem. Bio. 2014, 21 (12), 1670-1679.
Sarkar, M.; Liu, Y.; Qi, J.; Peng, H.; Morimoto, J.; Rader, C.; Chiorazzi, N.; Kodadek, T., Targeting Stereotyped B Cell Receptors from Chronic Lymphocytic Leukemia Patients with Synthetic Antigen Surrogates. J. Bio.Chem. 2016, 291 (14), 7558-7570.
Garrett, T. P. J.; McKern, N. M.; Lou, M.; Elleman, T. C.; Adams, T. E.; Lovrecz, G. O.; Kofler, M.; Jorissen, R. N.; Nice, E. C.; Burgess, A. W.; Ward, C. W., The Crystal Structure of a Truncated ErbB2 Ectodomain Reveals an Active Conformation, Poised to Interact with Other ErbB Receptors. Molecular Cell 2003, 11 (2), 495-505.
Yarden, Y.; Pines, G., The ERBB network: at last, cancer therapy meets systems biology. Nat. Rev. Cancer 2012, 12 (8), 553-563.
Larionov, A. A., Current Therapies for Human Epidermal Growth Factor Receptor 2-Positive Metastatic Breast Cancer Patients. Front Oncol 2018, 8, 89-89.
Ritter, C. A.; Perez-Torres, M.; Rinehart, C.; Guix, M.; Dugger, T.; Engelman, J. A.; Arteaga, C. L., Human Breast Cancer Cells Selected for Resistance to Trastuzumab <em>In vivo</em> Overexpress Epidermal Growth Factor Receptor and ErbB Ligands and Remain Dependent on the ErbB Receptor Network. Clin. Cancer Res. 2007, 13 (16), 4909-4919.
Holliday, D. L.; Speirs, V., Choosing the right cell line for breast cancer research. Breast Cancer Res. 2011, 13 (4), 215.
Dong, Q., Yu, P., Ye, L. et al. PCC0208027, a novel tyrosine kinase inhibitor, inhibits tumor growth of NSCLC by targeting EGFR and HER2 aberrations. Sci Rep 9, 5692 (2019). https://doi.org/10.1038/s41598-019-42245-3.

\* cited by examiner

A

Cyclic-γ-AApeptides

B

M-3-6-F

SEQUENCE LISTING

<160> NUMBER OF SEQ ID NOS: 1

<210> SEQ ID NO 1
<211> LENGTH: 419
<212> TYPE: PRT
<213> ORGANISM: Homo sapiens

<400> SEQUENCE: 1

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220
```

```
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
        260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
        290             295             300

Ser Thr Asp Val Gly Ser Cys Thr Leu Val Cys Pro Leu His Asn Gln
305             310             315                 320

Glu Val Thr Ala Glu Asp Gly Thr Gln Arg Cys Glu Lys Cys Ser Lys
                325             330             335

Pro Cys Ala Arg Gly Thr His Ser Leu Pro Pro Arg Pro Ala Ala Val
            340             345             350

Pro Val Pro Leu Arg Met Gln Pro Gly Pro Ala His Pro Val Leu Ser
        355             360             365

Phe Leu Arg Pro Ser Trp Asp Leu Val Ser Ala Phe Tyr Ser Leu Pro
        370             375             380

Leu Ala Pro Leu Ser Pro Thr Ser Val Pro Ile Ser Pro Val Ser Val
385             390             395             400

Gly Arg Gly Pro Asp Pro Asp Ala His Val Ala Val Asp Leu Ser Arg
            405             410             415

Tyr Glu Gly
```

PEPTIDOMIMETIC-BASED ANTIBODY SURROGATE FOR HER2

CROSS-REFERENCE TO RELATED APPLICATIONS

This application claims priority to U.S. Provisional Application No. 63/200,820 filed on Mar. 30, 2021, the contents of which is incorporated by reference in its entirety.

STATEMENT REGARDING FEDERALLY SPONSORED RESEARCH OR DEVELOPMENT

Not applicable.

Sequence Listing

A Sequence Listing accompanies this application and is submitted as an ASCII text file of the sequence listing named "173738_02445_ST25.txt" which is 3937 bytes in size and was created on Mar. 23, 2022. The sequence listing is electronically submitted via EFS-Web with the application and is incorporated herein by reference in its entirety.

BACKGROUND

Human epidermal growth factor receptor 2 (HER2), also known as ERBB2, is a member of the human epidermal growth factor receptor family[1], and is associated with fundamental processes including tumor cell proliferation, apoptosis, adhesion, migration and differentiation[2-4]. Previous work has suggested that approximately 20% of breast cancers have genomic amplification or overexpression of this HER2 gene[5], therefore, HER2 is an important therapeutic target for the treatment of breast cancer. Accordingly, there is a need in the art for therapeutics that target HER2.

SUMMARY

In one aspect of the current disclosure, cyclic g-amino acid peptide compounds (cyclic γ-AAs) are provided. In some embodiments, the compounds comprise: formula (i)

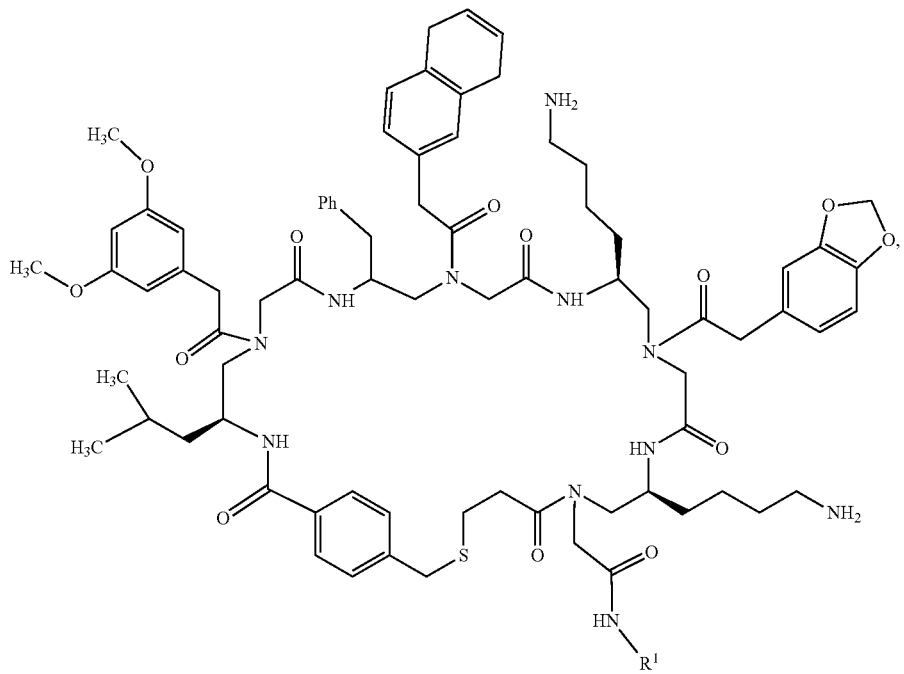

wherein R1 comprises H, a tag, a linker or a linker-tag complex. In some embodiments, R1 is a tag. In some embodiments, the tag is a fluorophore. In some embodiments, the tag is FITC, and comprises formula (ii):
formula (ii)
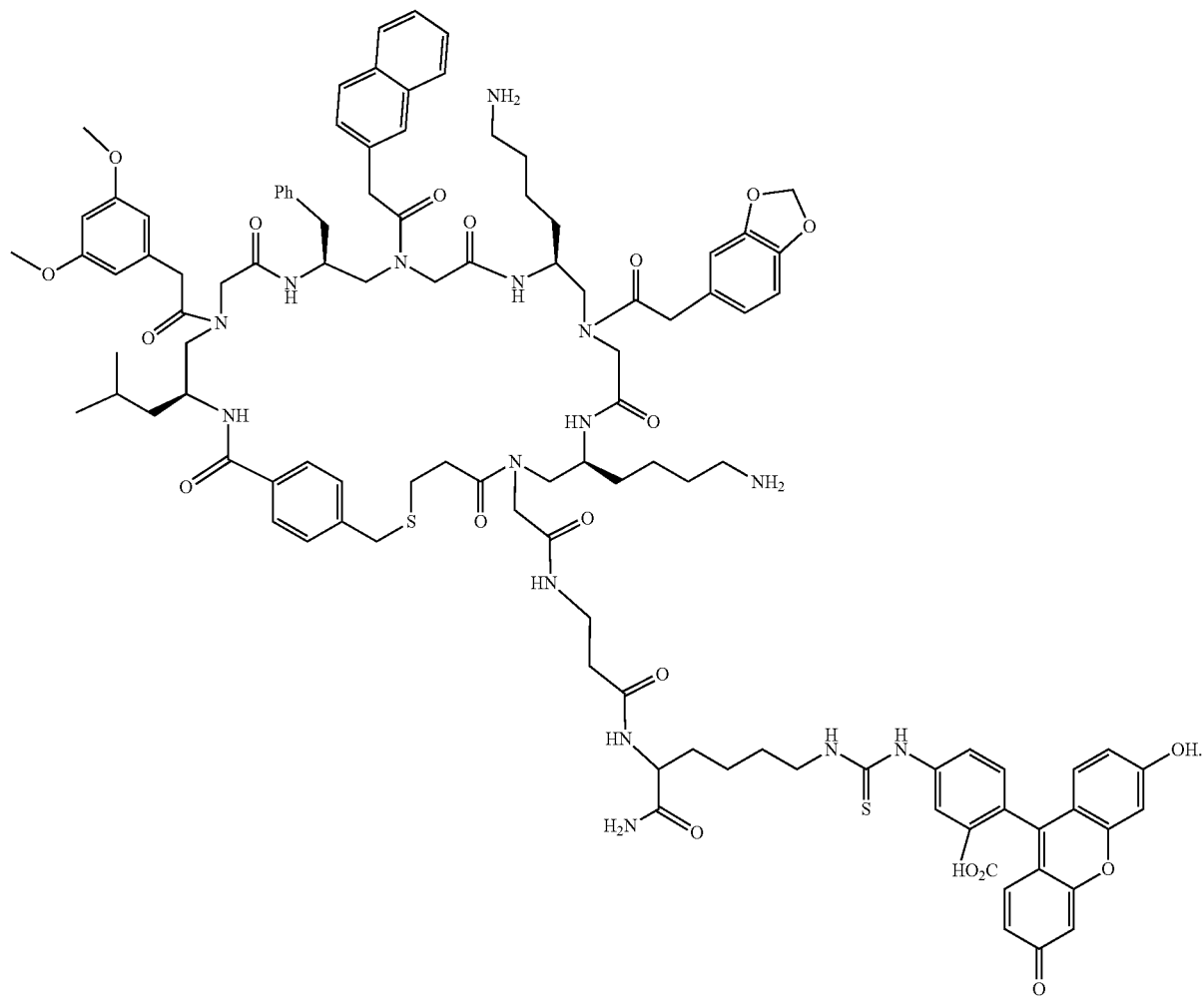

In some embodiments, R1 is a linker. In some embodiments, the linker is selected from an unsubstituted $C_1$-$C_{20}$ alkyl, substituted $C_1$-$C_{20}$ alkyl, $C_2$-$C_{20}$ alkenyl, phenyl, phenyl substituted $C_1$-$C_{20}$ alkyl, cycloalkyl substituted $C_1$-$C_{20}$ alkyl, an amino acid, and polyethylene glycol (PEG). In some embodiments, the linker is PEG chain, and the compound is formula (iii)

formula (iii)

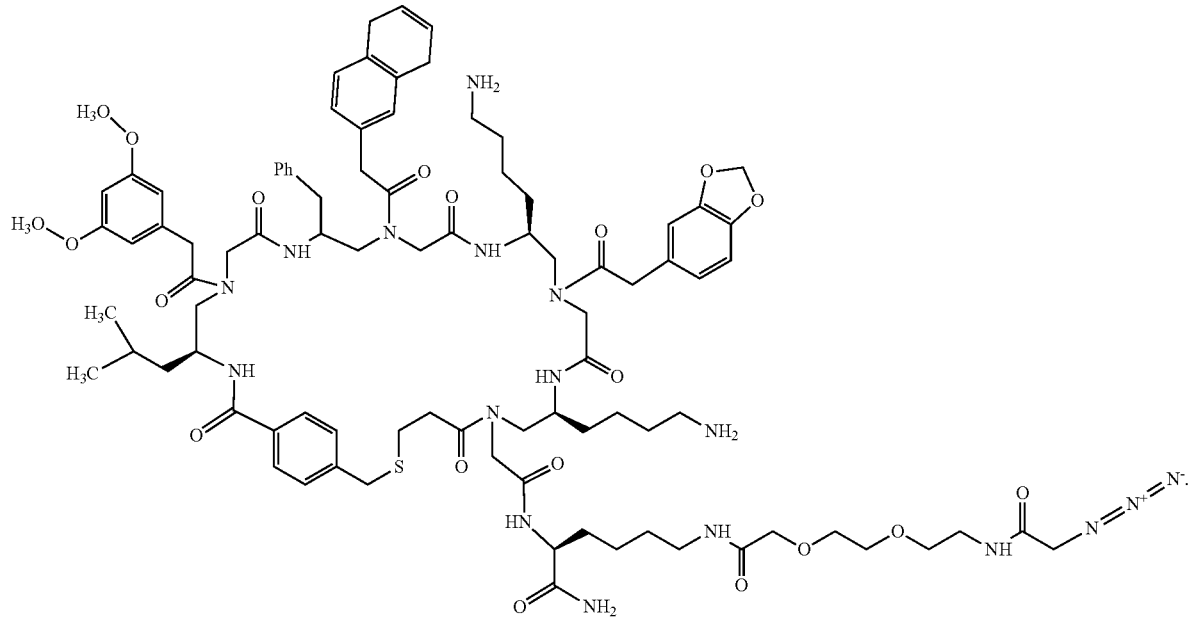

In some embodiments, the compound binds to Her2 with a dissociation constant ($K_d$) of less than about 230 nM. In some embodiments, the compound binds to Her2 with a dissociation constant ($K_d$) of less than about 50 nM. In some embodiments, the compound binds to Her2 and prevents heterodimerization of Her2.

In another aspect of the current disclosure, dimeric compounds are provided. In some embodiments, the dimeric compounds comprise formula (i)

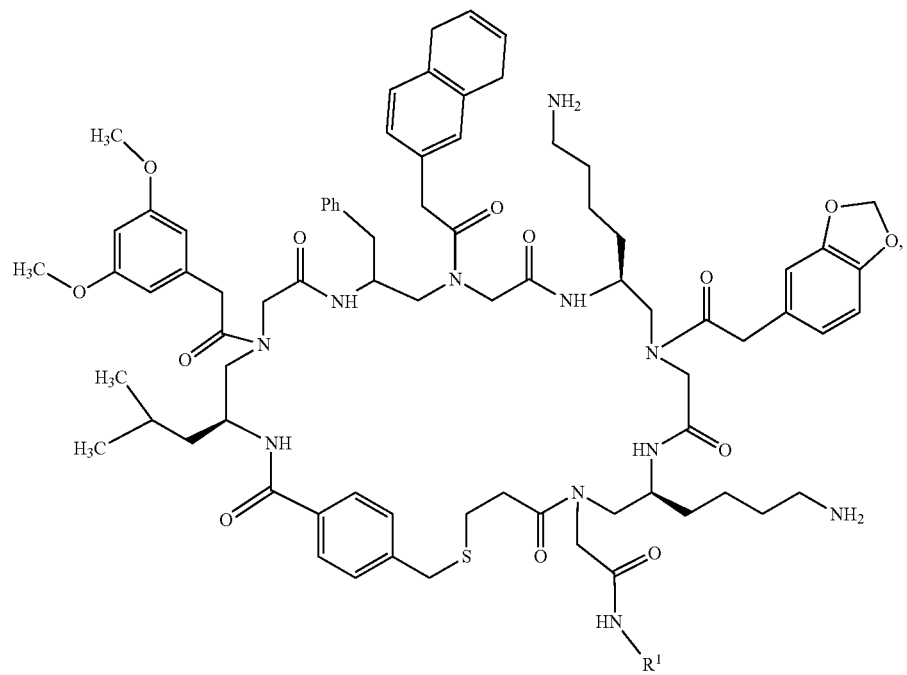

wherein the structure of the dimeric compound is formula (i)-linker-formula (i), wherein the first and second formula (i) compounds are linked via a linker through R1. In some embodiments, the linker is selected from an unsubstituted $C_1$-$C_{20}$ alkyl, substituted $C_1$-$C_{20}$ alkyl, $C_2$-$C_{20}$ alkenyl, phenyl, phenyl substituted $C_1$-$C_{20}$ alkyl, cycloalkyl substituted $C_1$-$C_{20}$ alkyl, an amino acid, and polyethylene glycol (PEG). In some embodiments, the compound is formula (iv)

formula (iv)

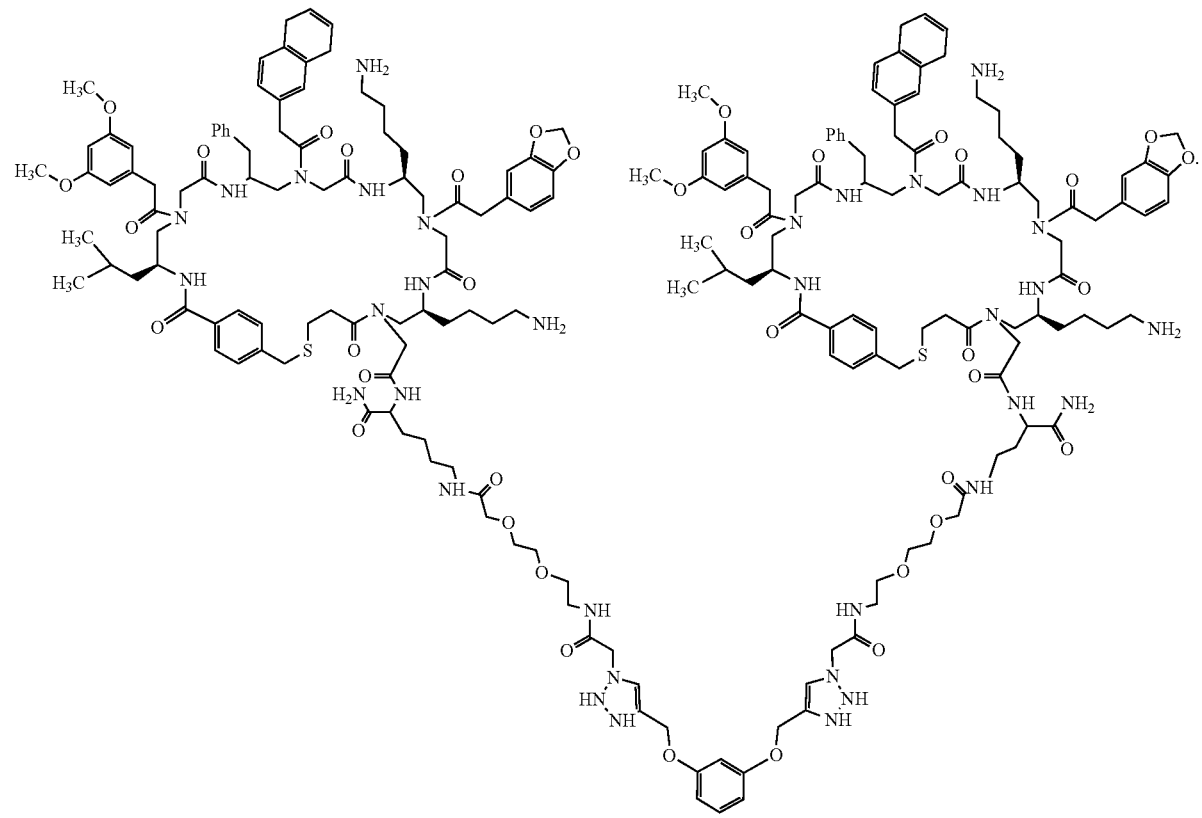 [SMILES: COc1cc(CC(=O)N2CC(=O)NC(Cc3ccccc3)CN(C(=O)Cc3ccc4c(c3)CC=CC4)CC(=O)N[C@@H](CCCCN)CN(C(=O)Cc3ccc4c(c3)OCO4)CC(=O)N[C@@H](CCCCN)CN(CC(=O)NC(CCCCNC(=O)COCCOCCNC(=O)CN3C=C(COc4cccc(OCC5=CN(CC(=O)NCCOCCOCC(=O)NCCC(NC(=O)CN6C[C@H](CCCCN)NC(=O)CN(C(=O)Cc7ccc8c(c7)OCO8)C[C@H](CCCCN)NC(=O)CN(C(=O)Cc7ccc8c(c7)CC=CC8)CC(Cc7ccccc7)NC(=O)CN(C(=O)Cc7cc(OC)cc(OC)c7)C[C@H](CC(C)C)NC(=O)c7ccc(cc7)CSCCC6=O)C(N)=O)NN5)c4)NN3)C(N)=O)C(=O)CCSCc3ccc(cc3)C(=O)N[C@@H](CC(C)C)C2)cc(OC)c1]

In some embodiments, the compound binds to Her2 with a dissociation constant ($K_d$) of less than about 230 nM. In some embodiments, the compound binds to Her2 with a dissociation constant ($K_d$) of less than about 50 nM. In some embodiments, the compound binds to Her2 and prevents heterodimerization of Her2.

In another aspect of the current disclosure, pharmaceutical compositions are provided. In some embodiments, the pharmaceutical compositions comprise a cyclic g-amino acid peptide (cyclic γ-AA) selected from the compounds having the formula:

formula (i)

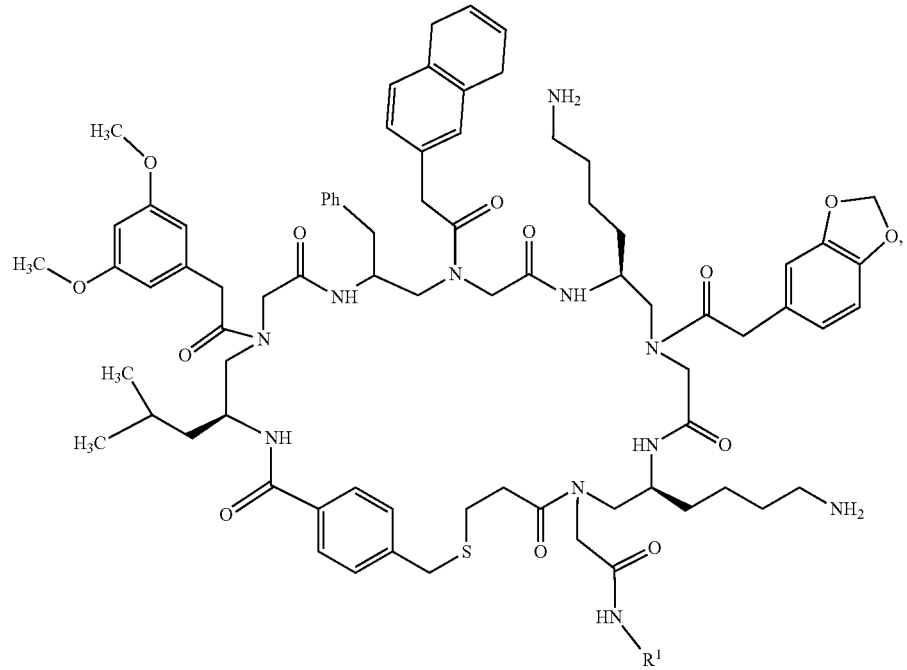

wherein R1 comprises H, a tag, a linker or a linker-tag complex, formula (iii)

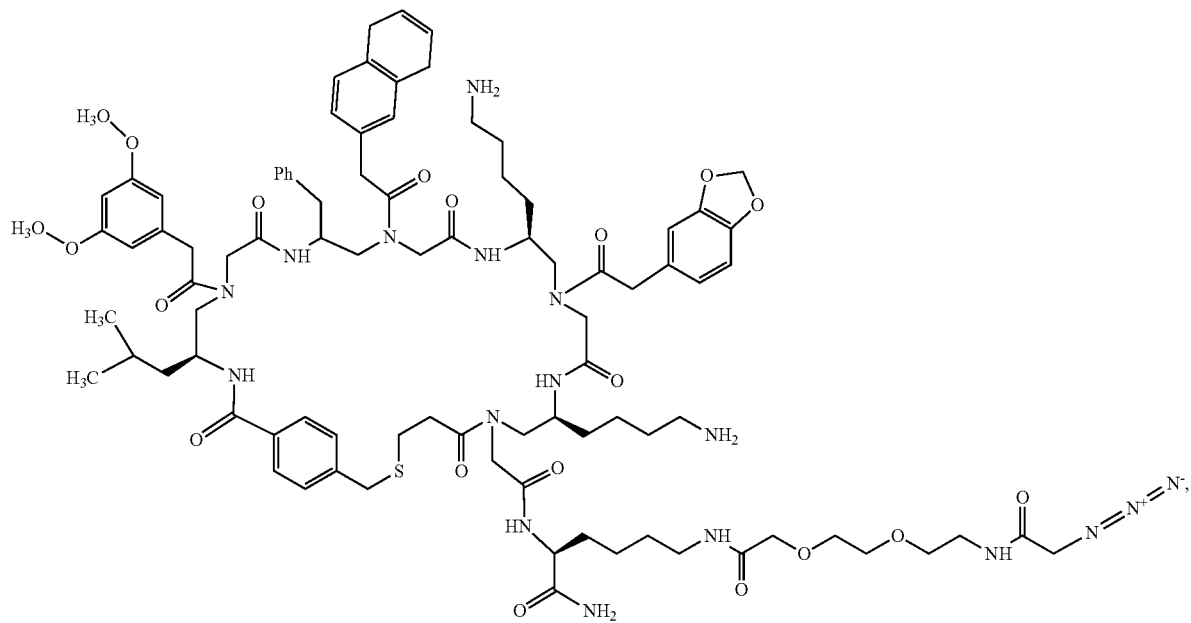

or formula (iv)
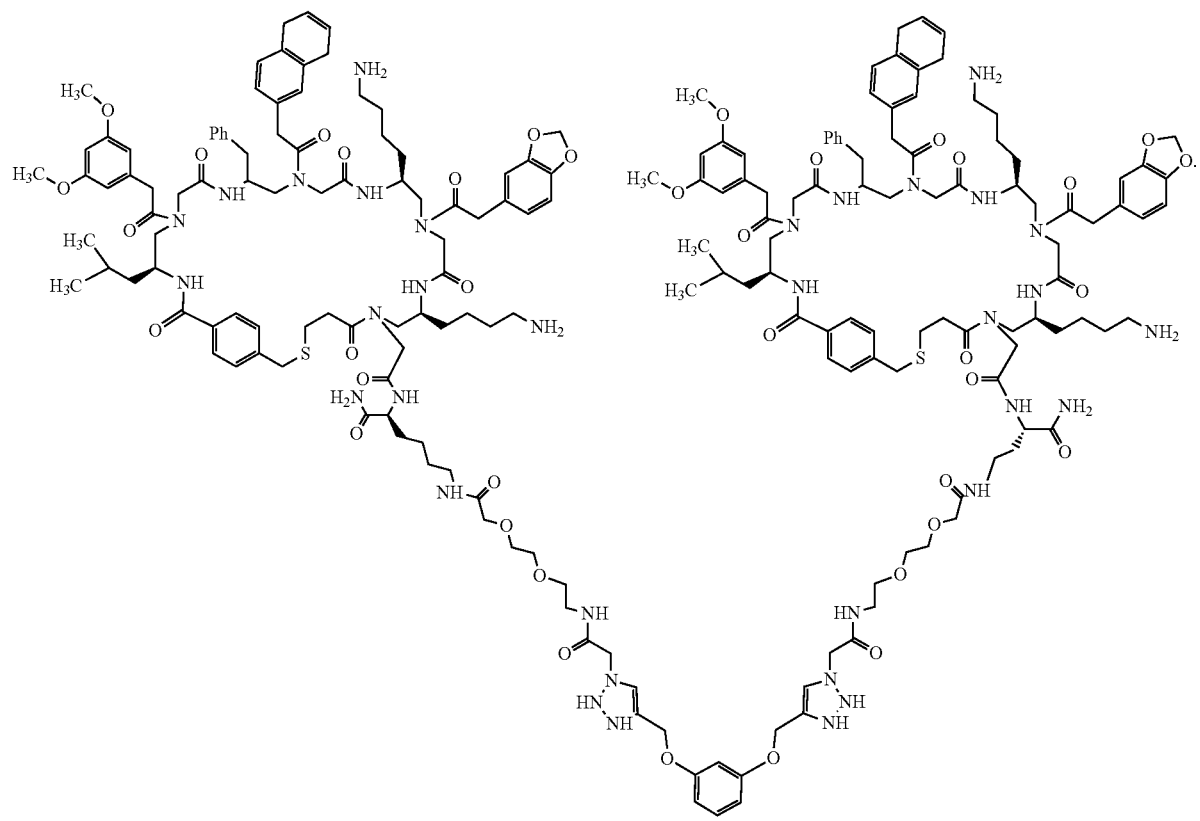 [SMILES: COc1cc(CC(=O)N2CC(=O)NC(Cc3ccccc3)CN(C(=O)Cc3ccc4c(c3)CC=CC4)CC(=O)N[C@@H](CCCCN)CN(C(=O)Cc3ccc4c(c3)OCO4)CC(=O)N[C@@H](CCCCN)CN(CC(=O)N[C@@H](CCCCNC(=O)COCCOCCNC(=O)CN3C=C(COc4cccc(OCC5=CN(CC(=O)NCCOCCOCC(=O)NCC[C@H](NC(=O)CN6C[C@H](CCCCN)NC(=O)CN(C(=O)Cc7ccc8c(c7)OCO8)C[C@H](CCCCN)NC(=O)CN(C(=O)Cc7ccc8c(c7)CC=CC8)CC(Cc7ccccc7)NC(=O)CN(C(=O)Cc7cc(OC)cc(OC)c7)C[C@H](CC(C)C)NC(=O)c7ccc(cc7)CSCCC6=O)C(N)=O)NN5)c4)NN3)C(N)=O)C(=O)CCSCc3ccc(cc3)C(=O)N[C@@H](CC(C)C)C2)cc(OC)c1]
, and a pharmaceutically acceptable carrier.

In another aspect of the current disclosure, methods of treating a cell proliferative disease or disorder in a subject in need thereof are provided. In some embodiments, the methods comprise: administering a therapeutically effective amount of a cyclic g-amino acid peptide comprising formula (i)

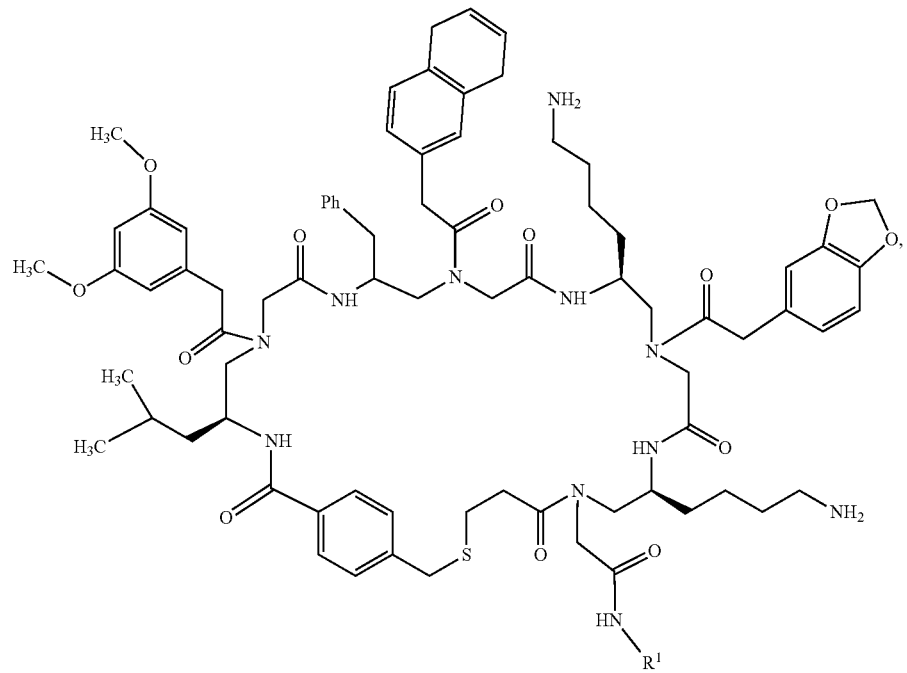

wherein R1 comprises H, a tag, a linker or a linker-tag complex,
formula (iii)

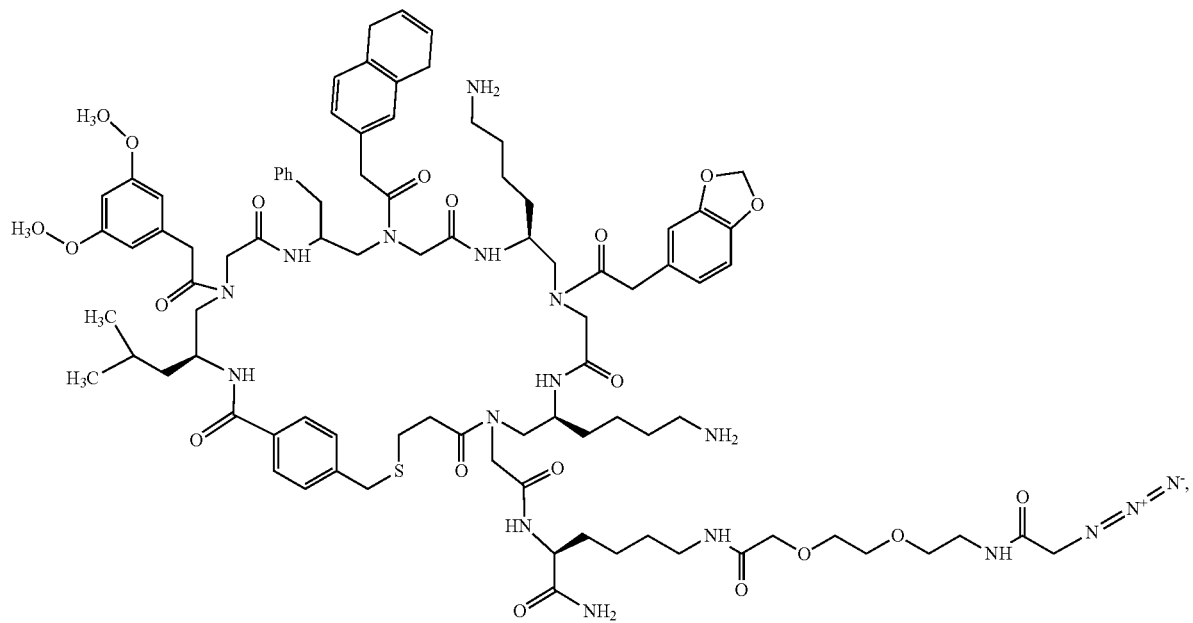

or formula (iv)

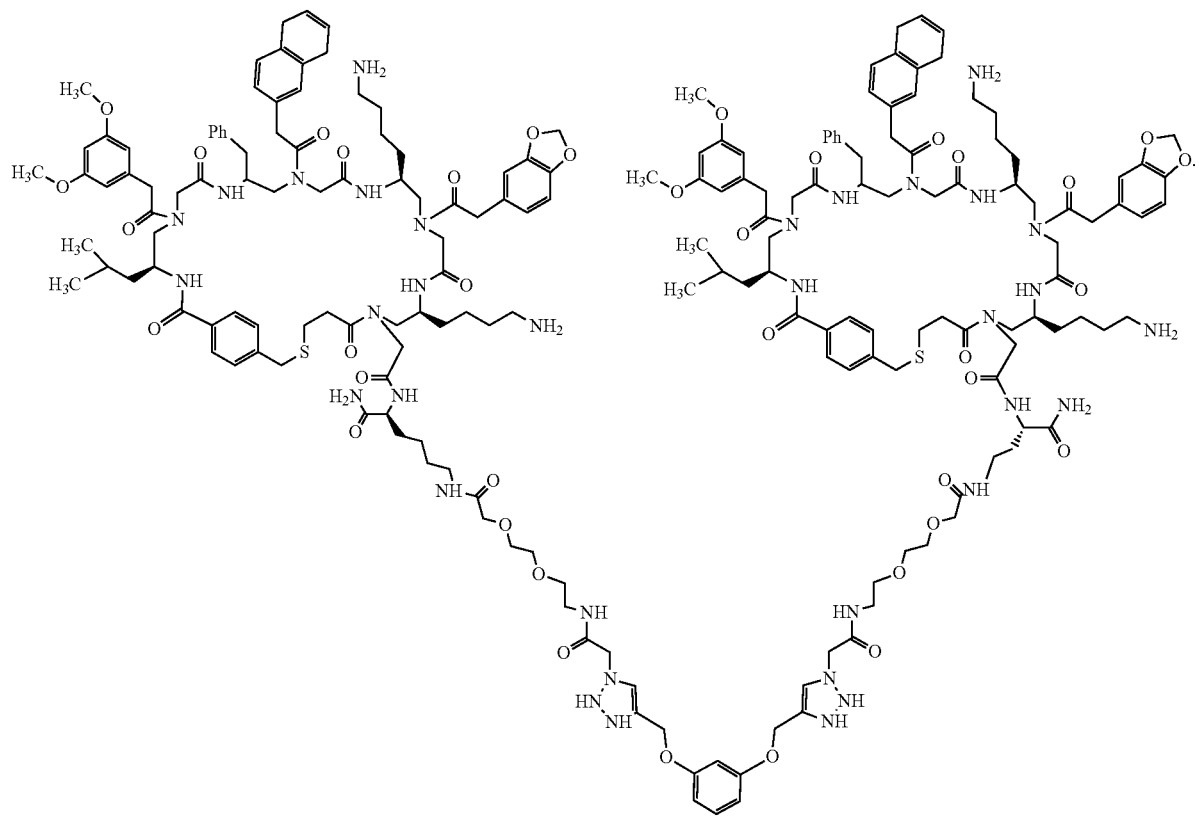 [SMILES: COc1cc(CC(=O)N2CC(=O)NC(Cc3ccccc3)CN(C(=O)Cc3ccc4c(c3)CC=CC4)CC(=O)N[C@@H](CCCCN)CN(C(=O)Cc3ccc4c(c3)OCO4)CC(=O)N[C@@H](CCCCN)CN(CC(=O)N[C@@H](CCCCNC(=O)COCCOCCNC(=O)CN3C=C(COc4cccc(OCC5=CN(CC(=O)NCCOCCOCC(=O)NCC[C@H](NC(=O)CN6C[C@H](CCCCN)NC(=O)CN(C(=O)Cc7ccc8c(c7)OCO8)C[C@H](CCCCN)NC(=O)CN(C(=O)Cc7ccc8c(c7)CC=CC8)CC(Cc7ccccc7)NC(=O)CN(C(=O)Cc7cc(OC)cc(OC)c7)C[C@H](CC(C)C)NC(=O)c7ccc(cc7)CSCCC6=O)C(N)=O)NN5)c4)NN3)C(N)=O)C(=O)CCSCc3ccc(cc3)C(=O)N[C@@H](CC(C)C)C2)cc(OC)c1]

, and a pharmaceutically acceptable carrier, to the subject to treat the cell proliferative disease or disorder. In some embodiments, the cell proliferative disease or disorder is cancer. In some embodiments, the cancer is characterized by expression of Her2. In some embodiments, the cancer is breast cancer. In some embodiments, the method reduces the growth of the tumor in the subject. In some embodiments, the method reduces phosphorylation of Her2, Erk, or Akt in the subject. In some embodiments, the method reduces proliferation of tumor cells in the subject. In some embodiments, the method reduces the volume of a tumor in the subject. In some embodiments, the methods further comprise administering a therapeutically effective amount of an additional chemotherapeutic or immunotherapeutic agent to the subject.

In another aspect of the current disclosure, methods of detecting Her2 in a sample from a subject suffering from a cancer suspected of expressing Her2 are provided. In some embodiments, the methods comprise: i) contacting the sample with the cyclic g-amino acid peptide compound comprising formula (i)

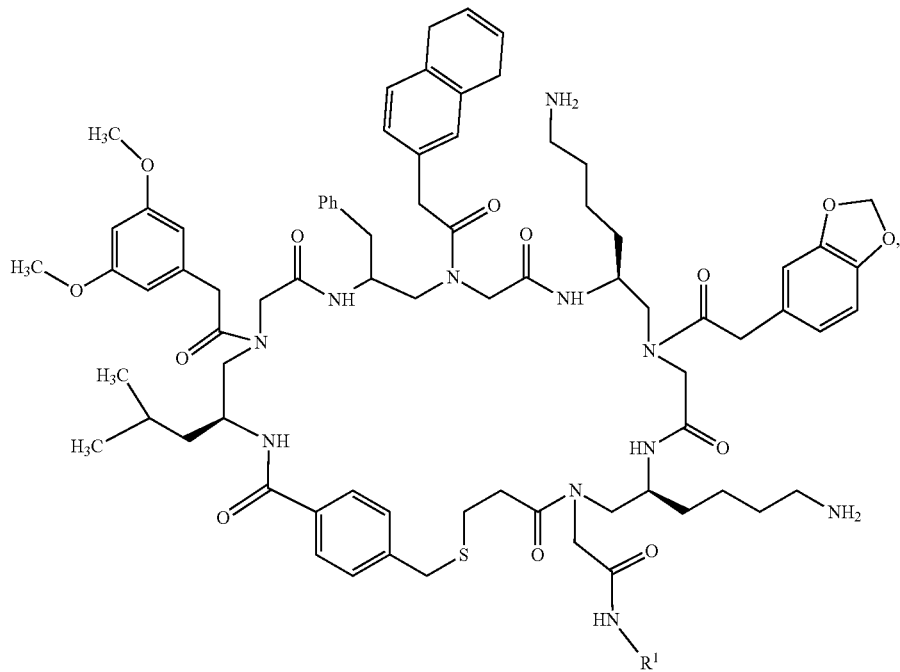

wherein R1 comprises H, a tag, a linker or a linker-tag complex to generate cyclic g-amino acid peptide-Her2 complex (complex), ii) detecting the presence of the complex wherein the presence of the complex indicates the presence of Her2 in a sample from the subject. In some embodiments, the method further comprises iii) administering a therapeutically effective amount of an anti-Her2 therapy. In some embodiments, the anti-Her2 therapy comprises: formula (i)

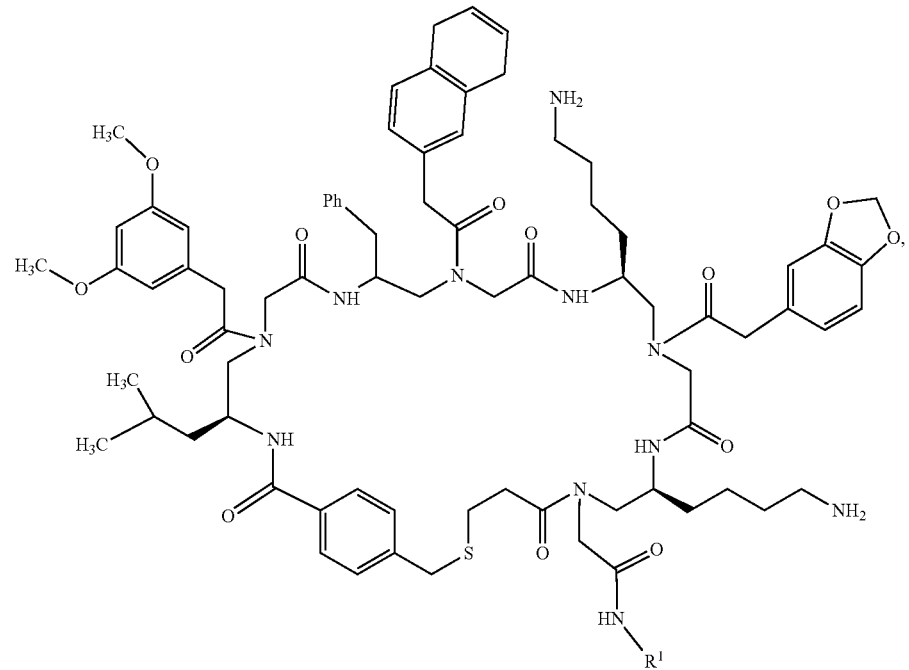

wherein R1 comprises H, a tag, a linker or a linker-tag complex,
formula (iii)
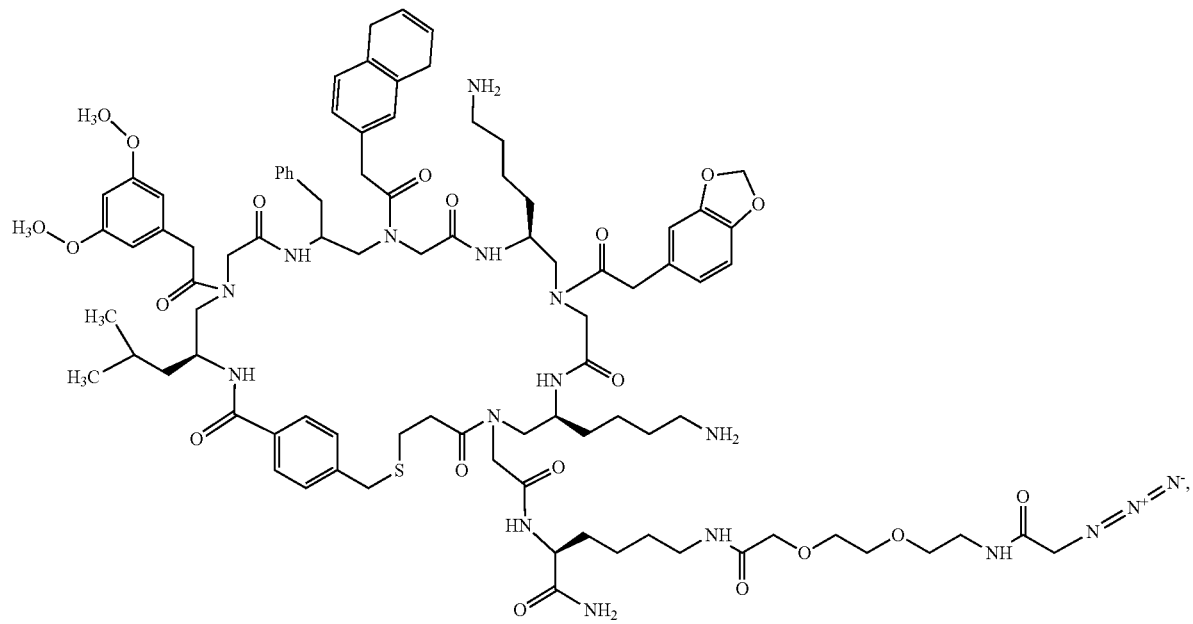
or formula (iv)
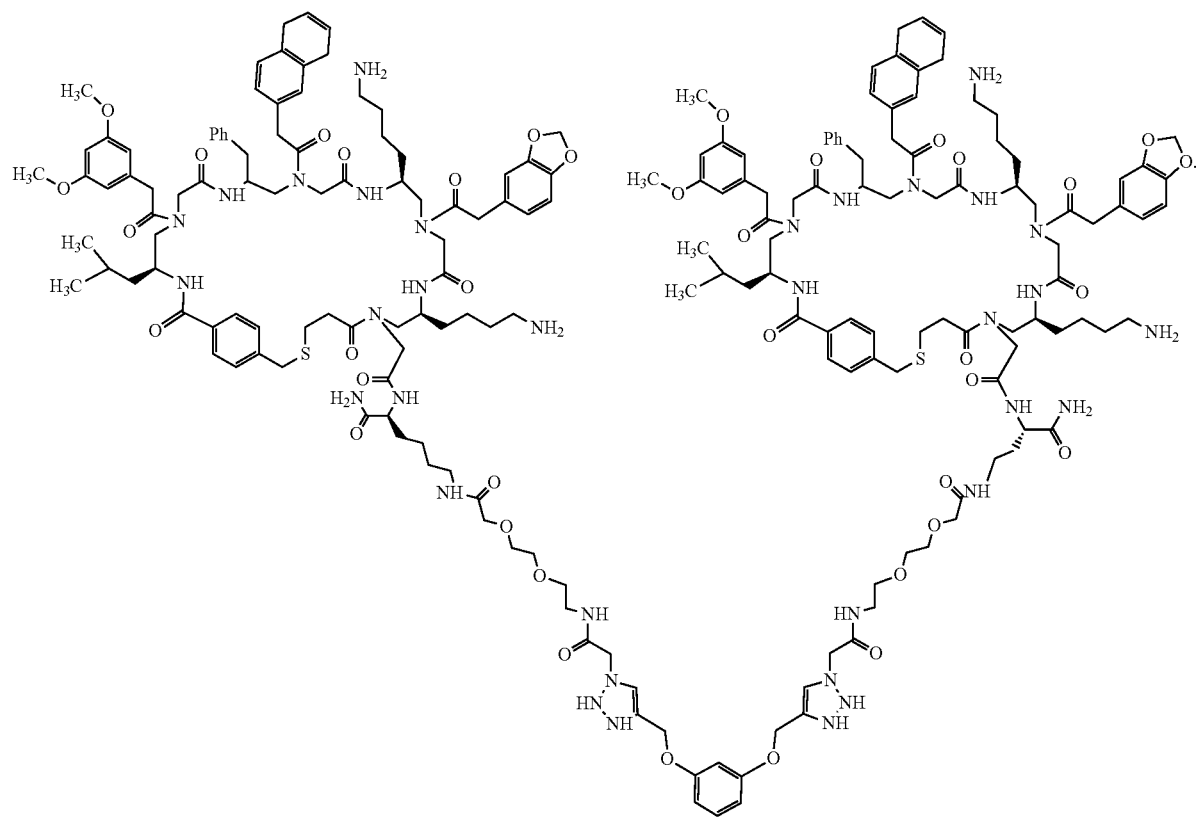 [SMILES: COc1cc(CC(=O)N2CC(=O)NC(Cc3ccccc3)CN(C(=O)Cc3ccc4c(c3)CC=CC4)CC(=O)N[C@@H](CCCCN)CN(C(=O)Cc3ccc4c(c3)OCO4)CC(=O)N[C@@H](CCCCN)CN(CC(=O)N[C@@H](CCCCNC(=O)COCCOCCNC(=O)CN3C=C(COc4cccc(OCC5=CN(CC(=O)NCCOCCOCC(=O)NCC[C@H](NC(=O)CN6C[C@H](CCCCN)NC(=O)CN(C(=O)Cc7ccc8c(c7)OCO8)C[C@H](CCCCN)NC(=O)CN(C(=O)Cc7ccc8c(c7)CC=CC8)CC(Cc7ccccc7)NC(=O)CN(C(=O)Cc7cc(OC)cc(OC)c7)C[C@H](CC(C)C)NC(=O)c7ccc(cc7)CSCCC6=O)C(N)=O)NN5)c4)NN3)C(N)=O)C(=O)CCSCc3ccc(cc3)C(=O)N[C@@H](CC(C)C)C2)cc(OC)c1]
, and a pharmaceutically acceptable carrier.

In another aspect of the current disclosure, kits are provided. In some embodiments, the kits comprise: i) the cyclic γ-AA compound with the structure of formula (i)

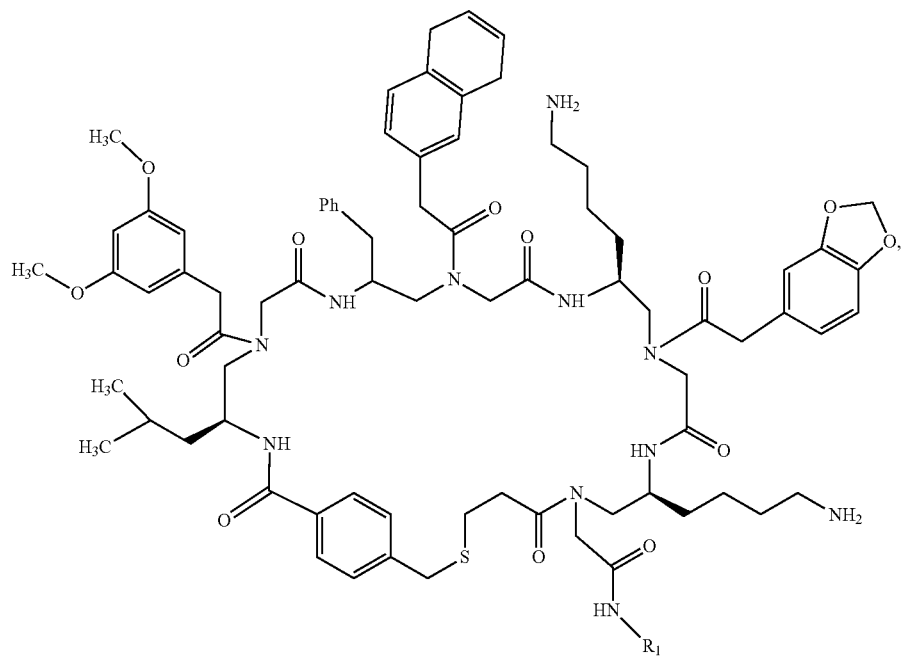

wherein R1 comprises H, a tag, a linker or a linker-tag complex, and ii) a detection reagent. In some embodiments, the kits further comprise: iii) a solid support. In some embodiments, the solid support comprises a microplate, a lateral flow device, or a microfluidic device. In some embodiments, the cyclic g-AA comprises a compound with the formula (ii)

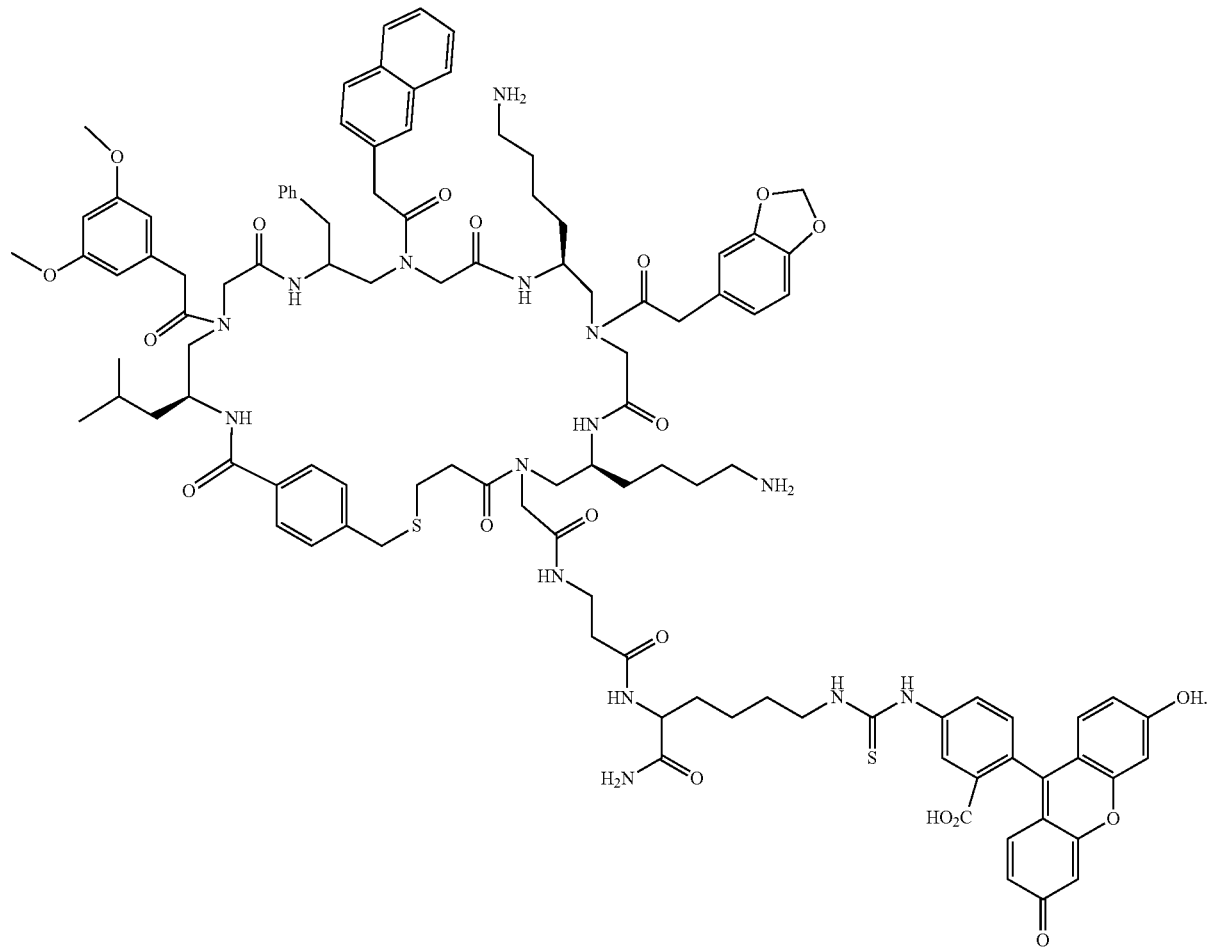

In some embodiments, the detection reagent comprises a secondary antibody specific for the cyclic γ-AA.

DETAILED DESCRIPTION

Figure 1:
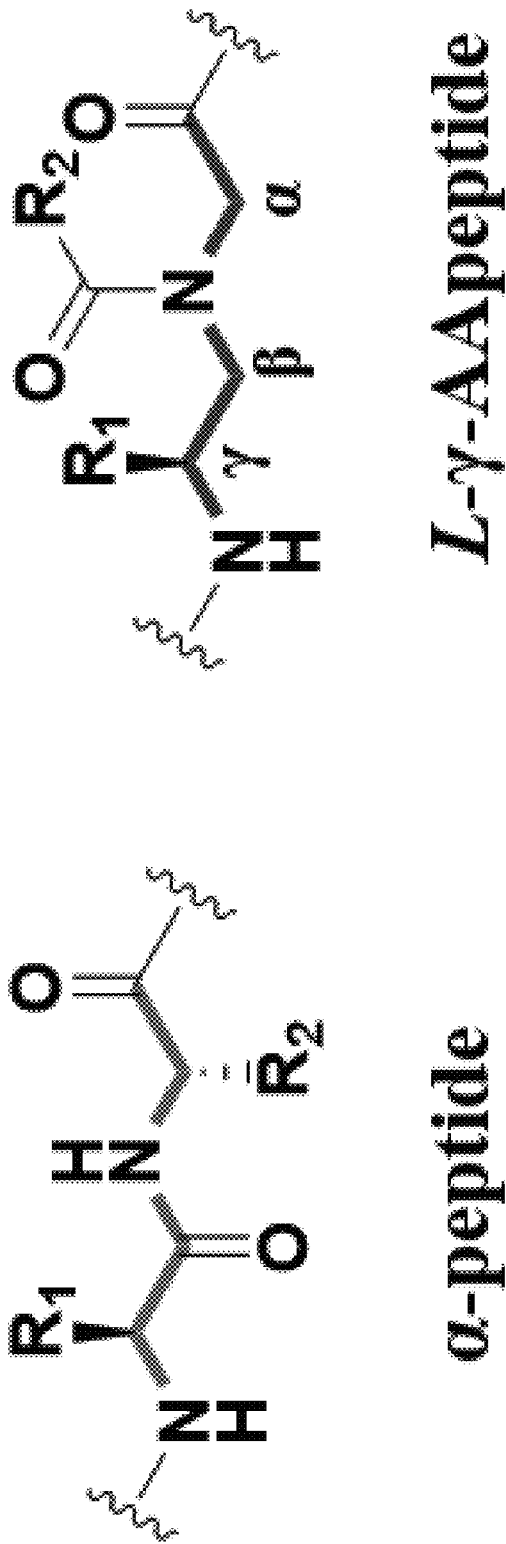
FIG. 1. General structure of α-peptide and L-γ-AApeptide.

In the present disclosure, the inventors used a one-bead-two-compounds (OBTC) combinatorial library of cyclic γ-amino acid peptides to identify novel compounds with high affinity for human epidermal growth factor receptor 2 (HER2) extracellular domain. Disclosed herein are novel cyclic γ-amino acid compounds, pharmaceutical compositions comprising said compounds, and methods of using the same. In one embodiment, a dimeric compound of the cyclic γ-amino acid compounds, having a structure that mimic antibody structures.

The present invention is described herein using several definitions, as set forth below and throughout the application.

Peptidomimetic-Based Antibody Surrogates for HER2

Disclosed herein are compounds, pharmaceutical compositions comprising the compounds, and methods of using the compounds and pharmaceutical compositions for treating a subject having or at risk for developing a disease or disorder associated with human epidermal growth factor receptor 2 (HER2) biological activity. The disclosed compounds may inhibit the biological activity of HER2, including the heterodimerization of HER2 and/or the receptor tyrosine kinase activity of HER2. As such, the disclosed compounds and pharmaceutical compositions may be utilized in methods for treating a subject having or at risk for developing a disease or disorder that is associated with HER2 activity which may be, for example, a cell proliferative disease or disorder, e.g., cancer.

As used herein, HER2 refers to the human epidermal growth factor receptor 2 coding sequence or protein with the sequence SEQ ID NO: 1, or a fragment thereof. The HER family proteins are type I transmembrane growth factor receptors that function to activate intracellular signaling pathways in response to extracellular signals. Their structure consists of an extracellular ligand binding domain, a transmembrane domain, and an intracellular tyrosine kinase domain. The function of this family is simplest in *C. elegans* where signaling is mediated by a single ligand and a single receptor and slightly more complex in *Drosophila* where four ligands signal through a single receptor. The system is far more complicated in mammalians where the functions of this family are performed by at least twelve ligands and four receptors. While the reasons behind such multiplicity in this system are not well understood, much is now known regarding the molecular basis underlying their signaling activities. Upon ligand binding to their extracellular domains, HER proteins undergo dimerization and transphosphorylation of their intracellular domains. These phosphorylated tyrosine residues dock numerous intracellular signaling molecules leading to activation of a plethora of downstream second messenger pathways and crosstalk with other transmembrane signaling pathways leading to diverse biological effects. The structural bases for receptor dimerization have been coming to light in the past few years by crystallographic data. The extracellular domain of HER proteins can exist in a closed inhibited or an open active conformation. Ligand binding induces a conformational change in their extracellular domain that induces the active conformation and promotes their dimerization and consequent transphosphorylation. Partner selection appears to be a key determinant of signaling activity among HER proteins and their signaling functions follow a distinct hierarchical order favoring heterodimers over homodimers. HER2 has the strongest catalytic kinase activity and HER2-containing heterodimers have the strongest signaling functions. The expansion of the HER family in mammalian systems has been associated with functional differentiation necessitating interdependence rather than promoting independent or redundant functions. This is exemplified by HER2 and HER3 which are functionally incomplete receptor molecules. Unlike the other members of the family, the extracellular domain of HER2 does not pivot between active and inactive conformations and constitutively exists in an activated conformation. Consistent with its constitutively active conformation, HER2 lacks ligand binding activity and its signaling function is engaged by its ligand-bound heterodimeric partners. On the other hand HER3, unlike the other members, lacks ATP binding within its catalytic domain and is catalytically inactive. Consistent with this, the signaling functions of HER3 are mediated entirely through the kinase activity of its heterodimeric partners. Even chimeric kinase-active HER3 constructs fail to signal without hetero-partners suggesting that HER3 even lacks the ability to homodimerize and is an obligate heterodimerization partner. Although individually they are incomplete signaling molecules, a large body of evidence not only establishes HER2 and HER3 as obligate partners, but their complex forms the most active signaling heterodimer of the family and essential for many biologic and developmental processes.

Thus, by targeting cyclic γ-amino acid peptide compounds to HER2 and disrupting its biological function, e.g., heterodimerization, the disclosed compounds provide a novel therapeutic for the treatment of diseases or disorders characterized by HER2 expression.

Figure 10:
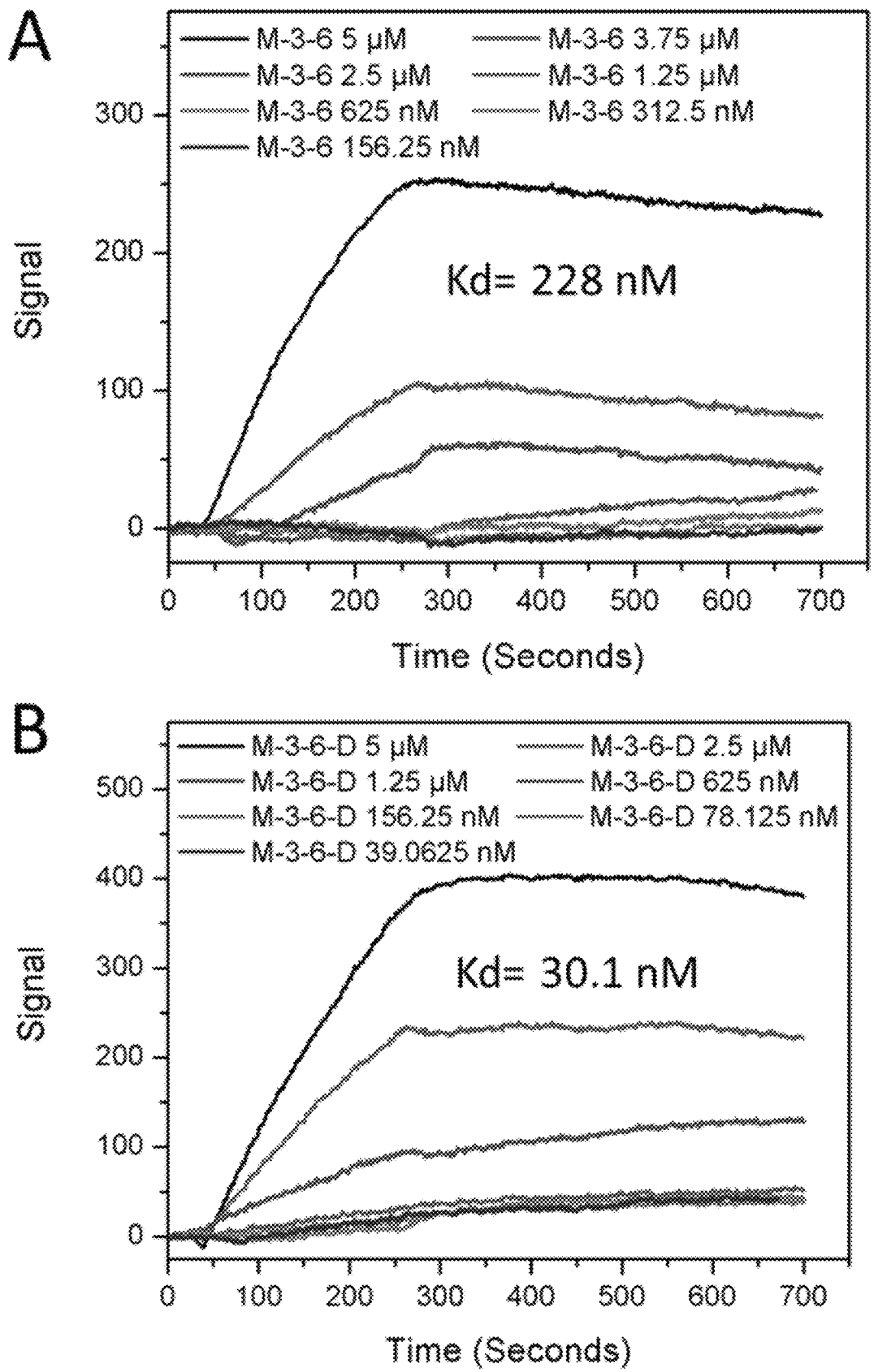
FIG. 10. Binding affinity of compounds M-3-6 (A), M-3-6-D (B) to HER2 as determined by SPR.
Figure 11:
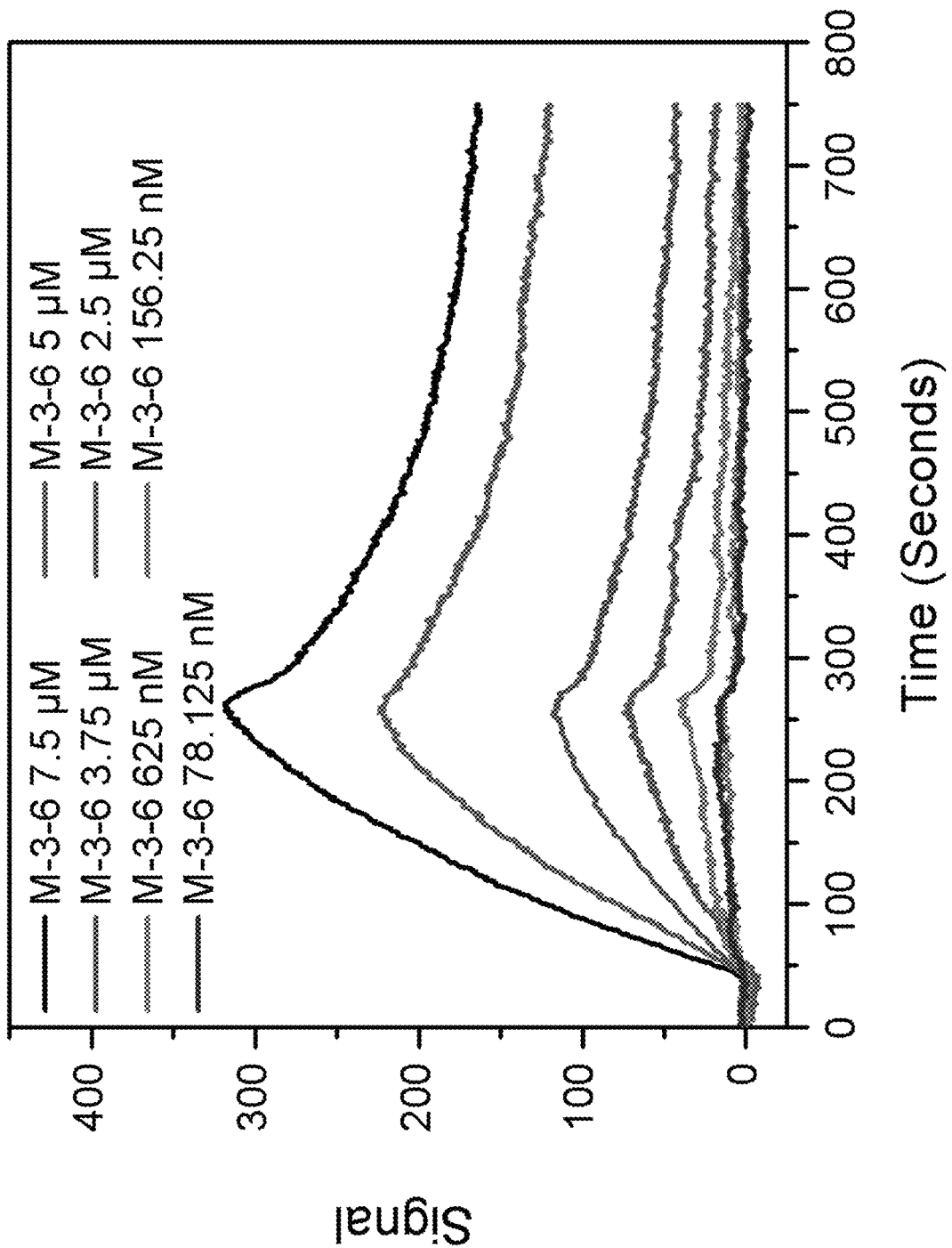
FIG. 11. Binding affinity of cyclic γ-AApeptides M-3-6 to EGFR as determined by SPR with a KD of 1.95 μM.
Figure 12:
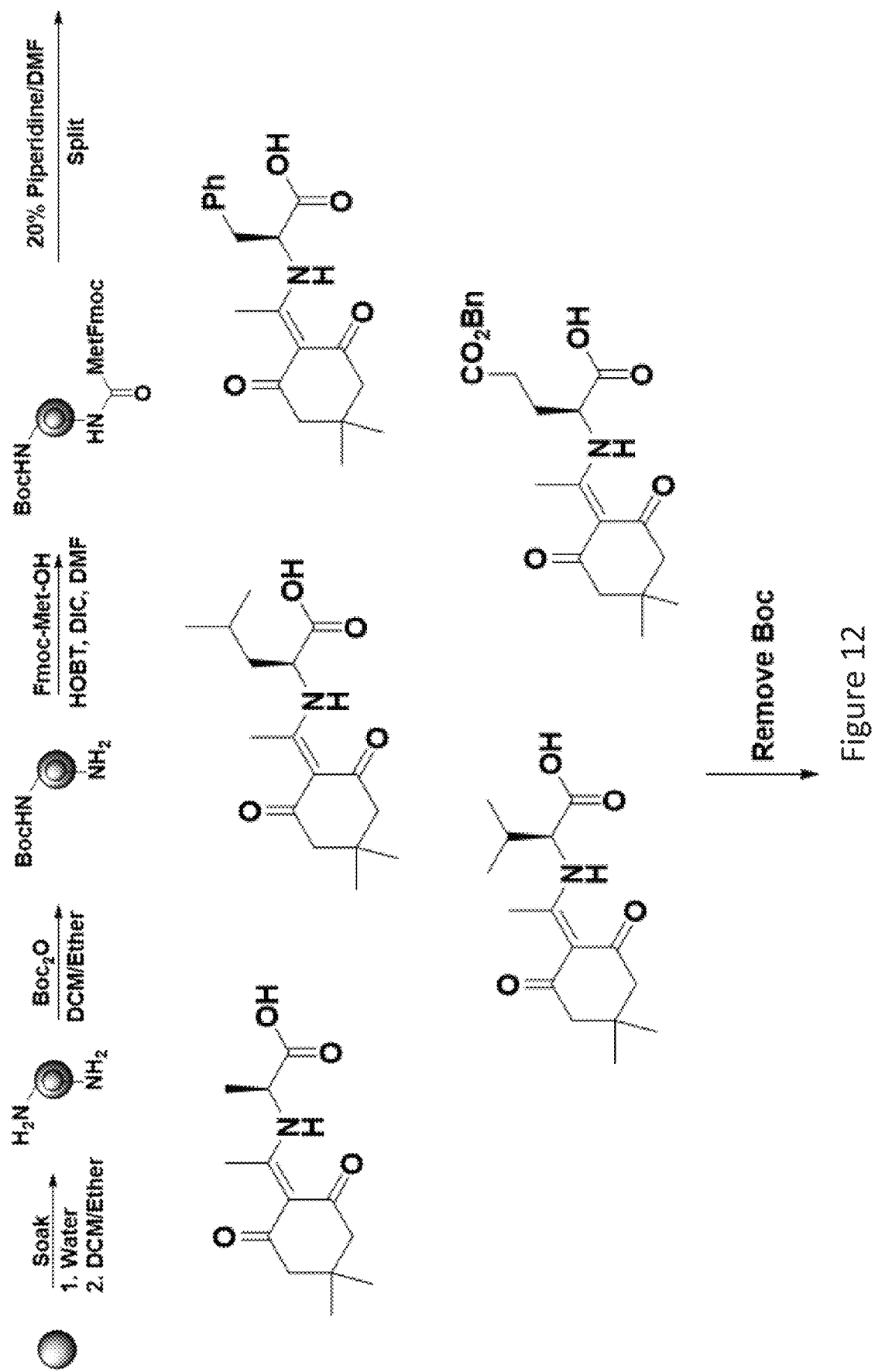
FIG. 12. The preparation of the cyclic γ-AApeptides library.
Figure 12:
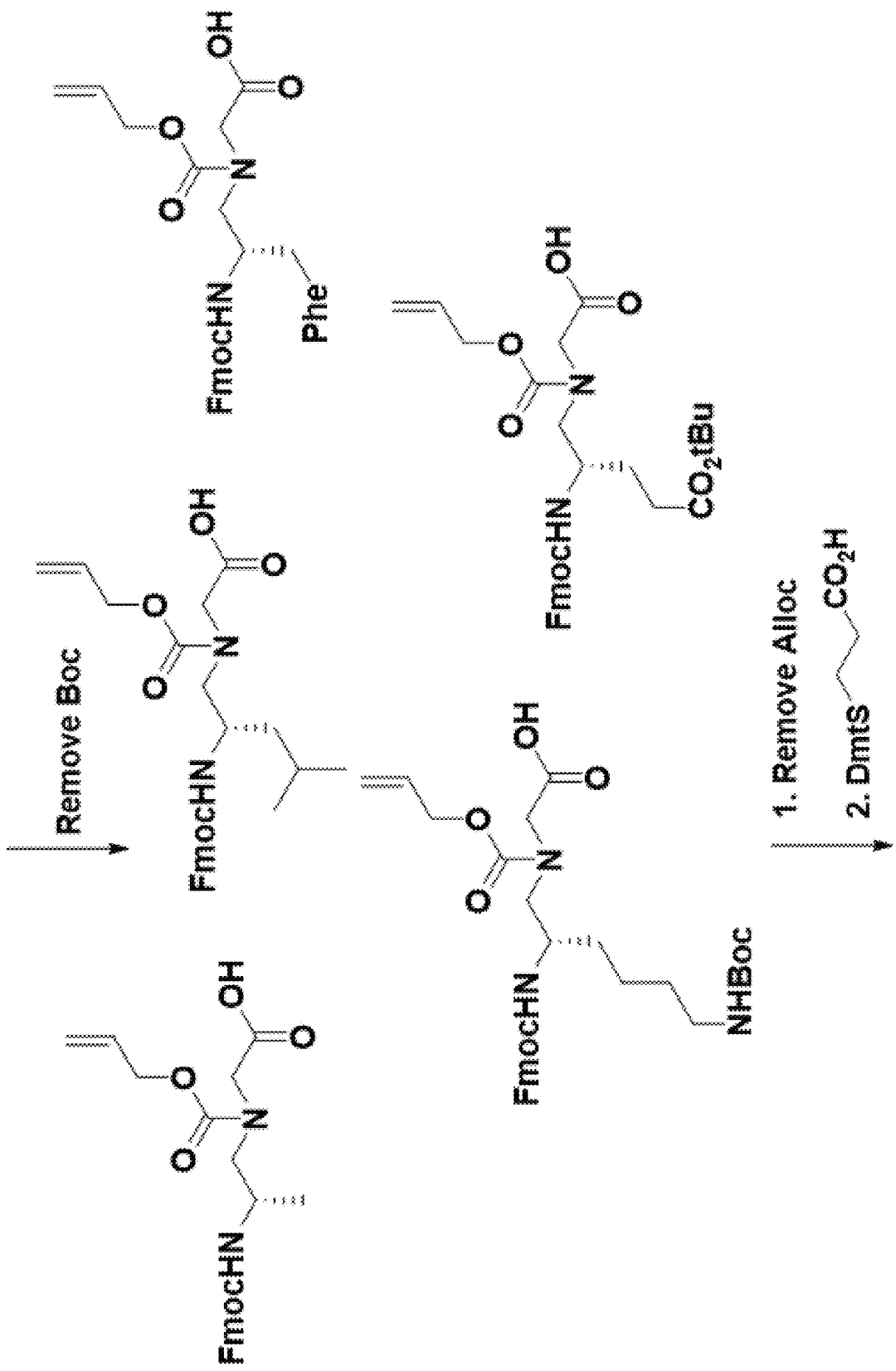
Figure 12:
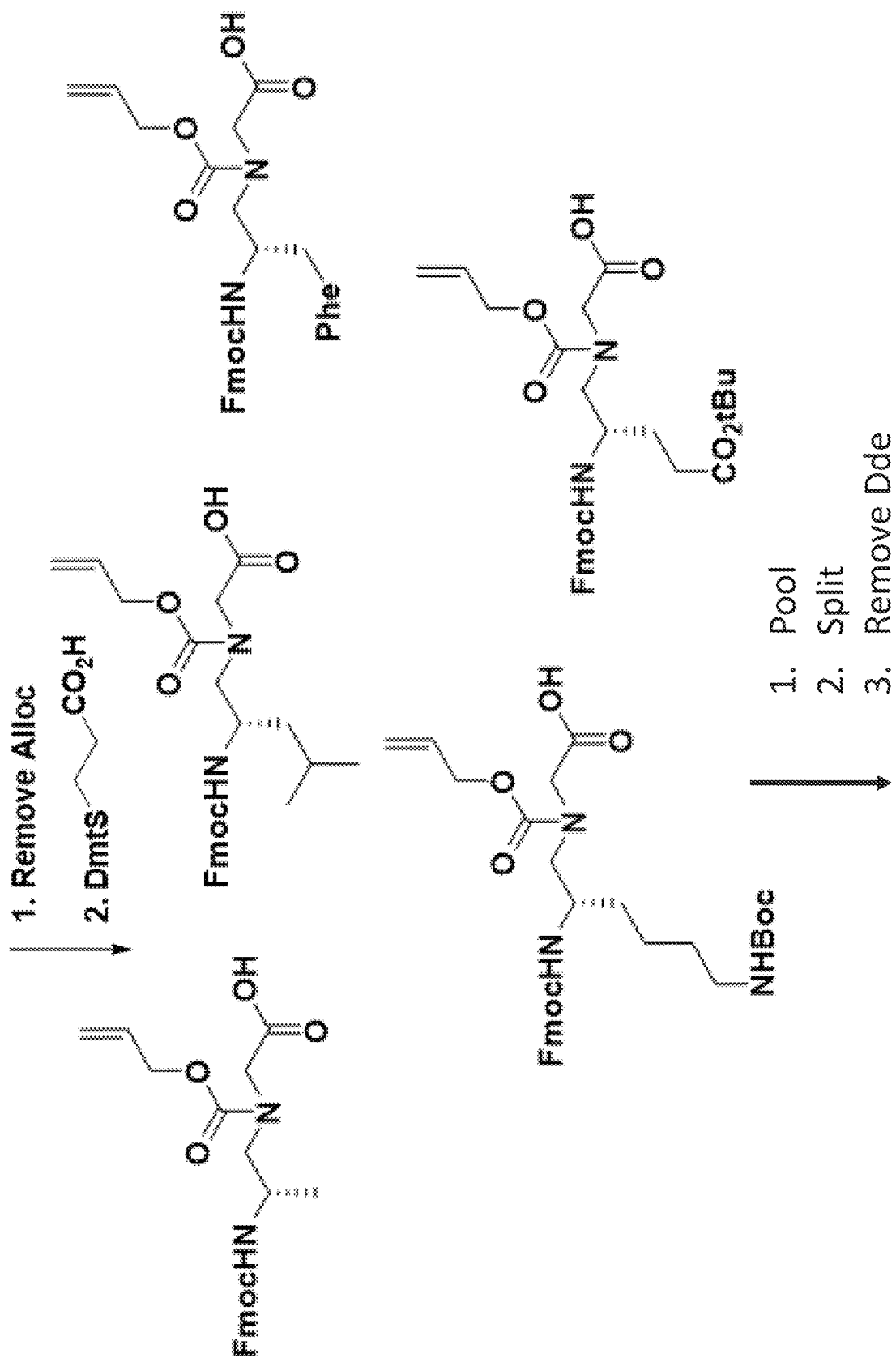
Figure 12:
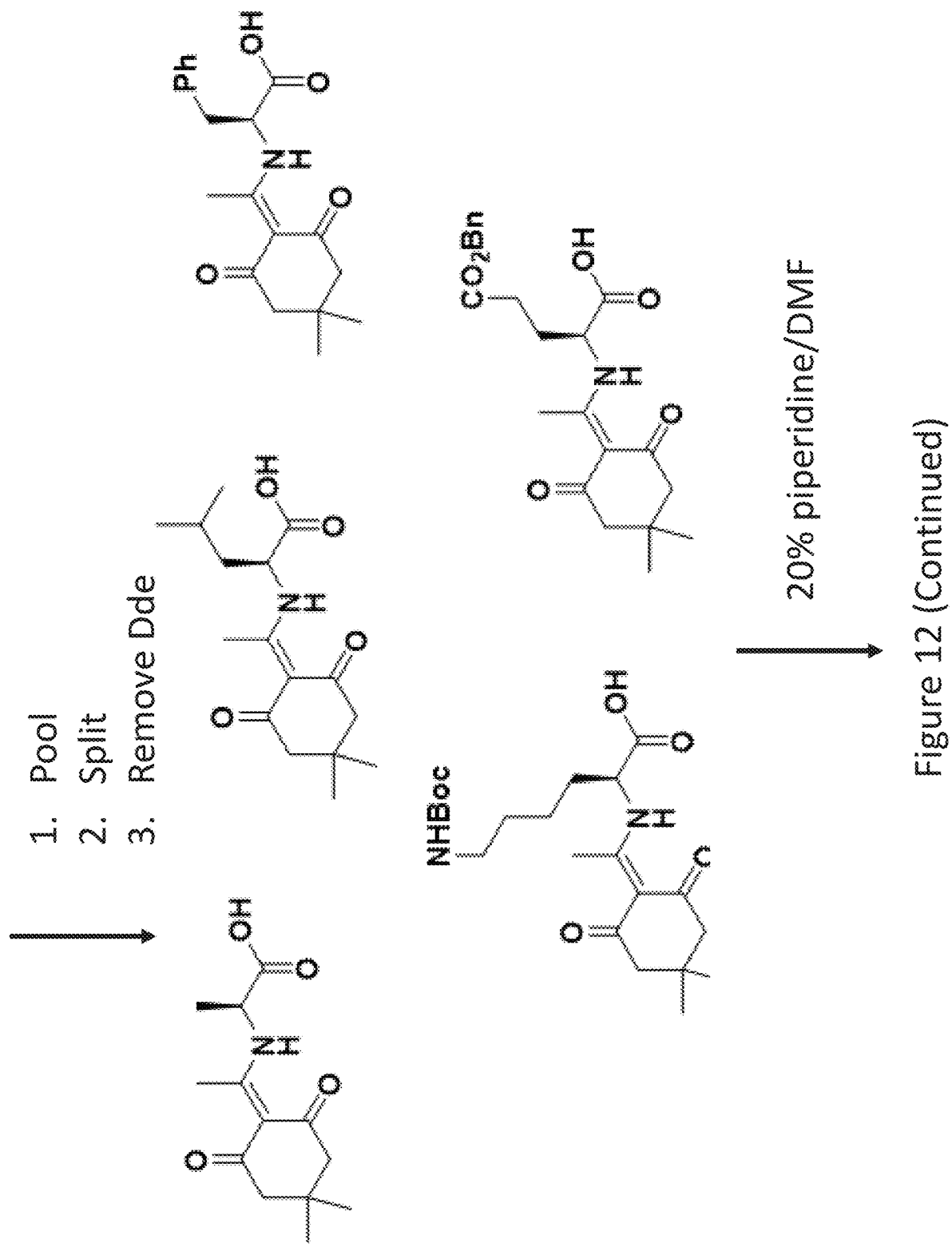
Figure 12:
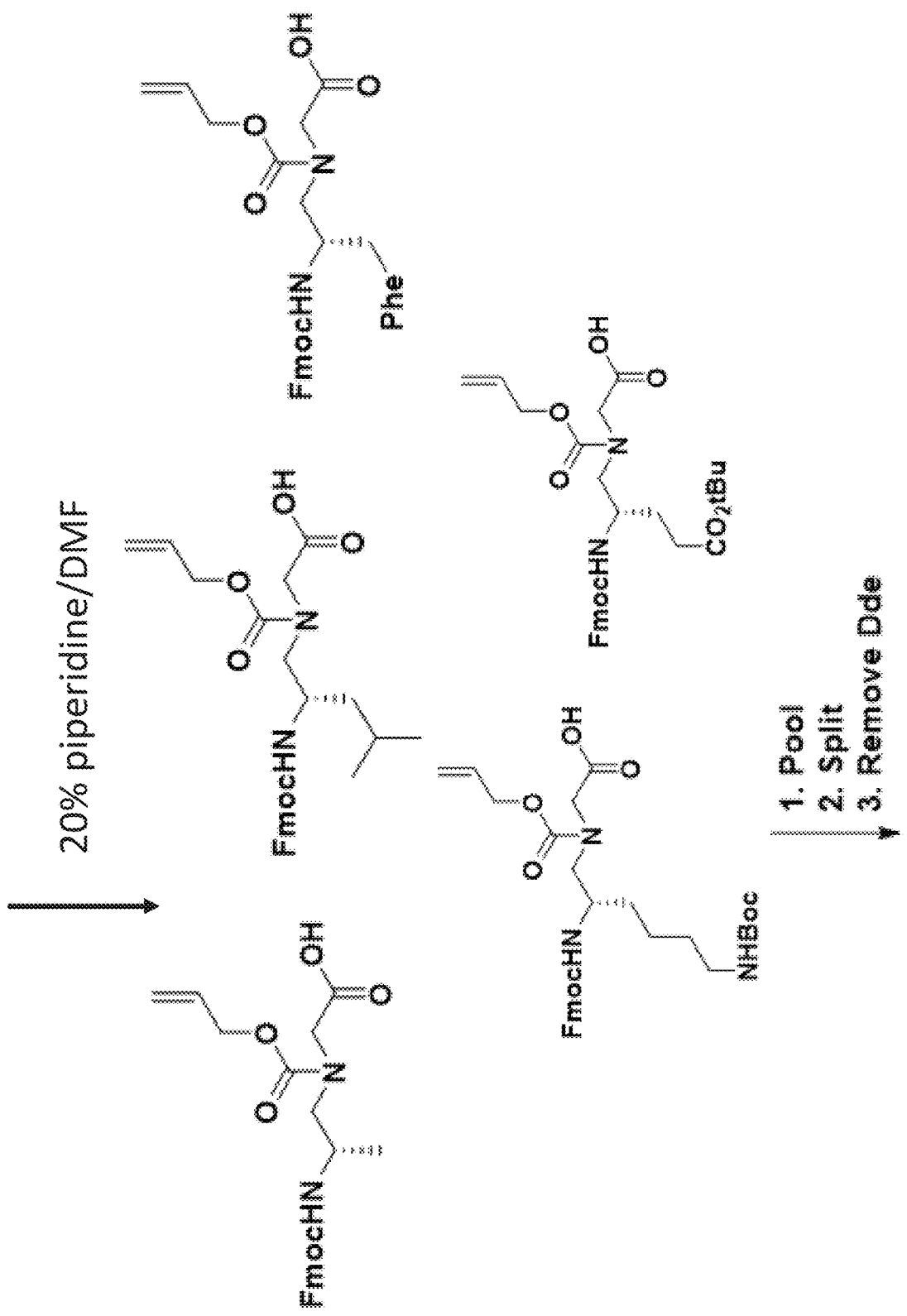
Figure 12:
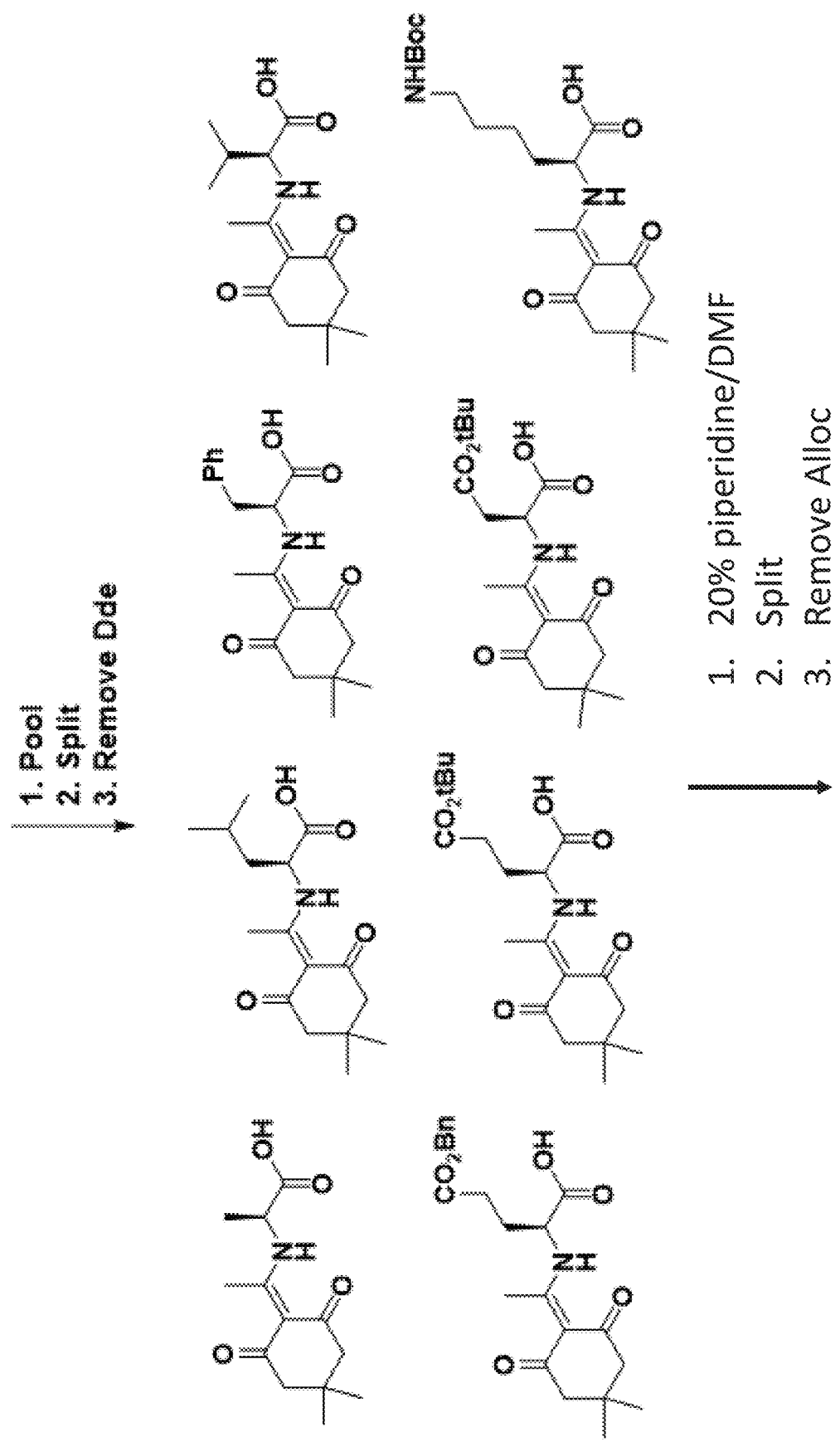
Figure 12:
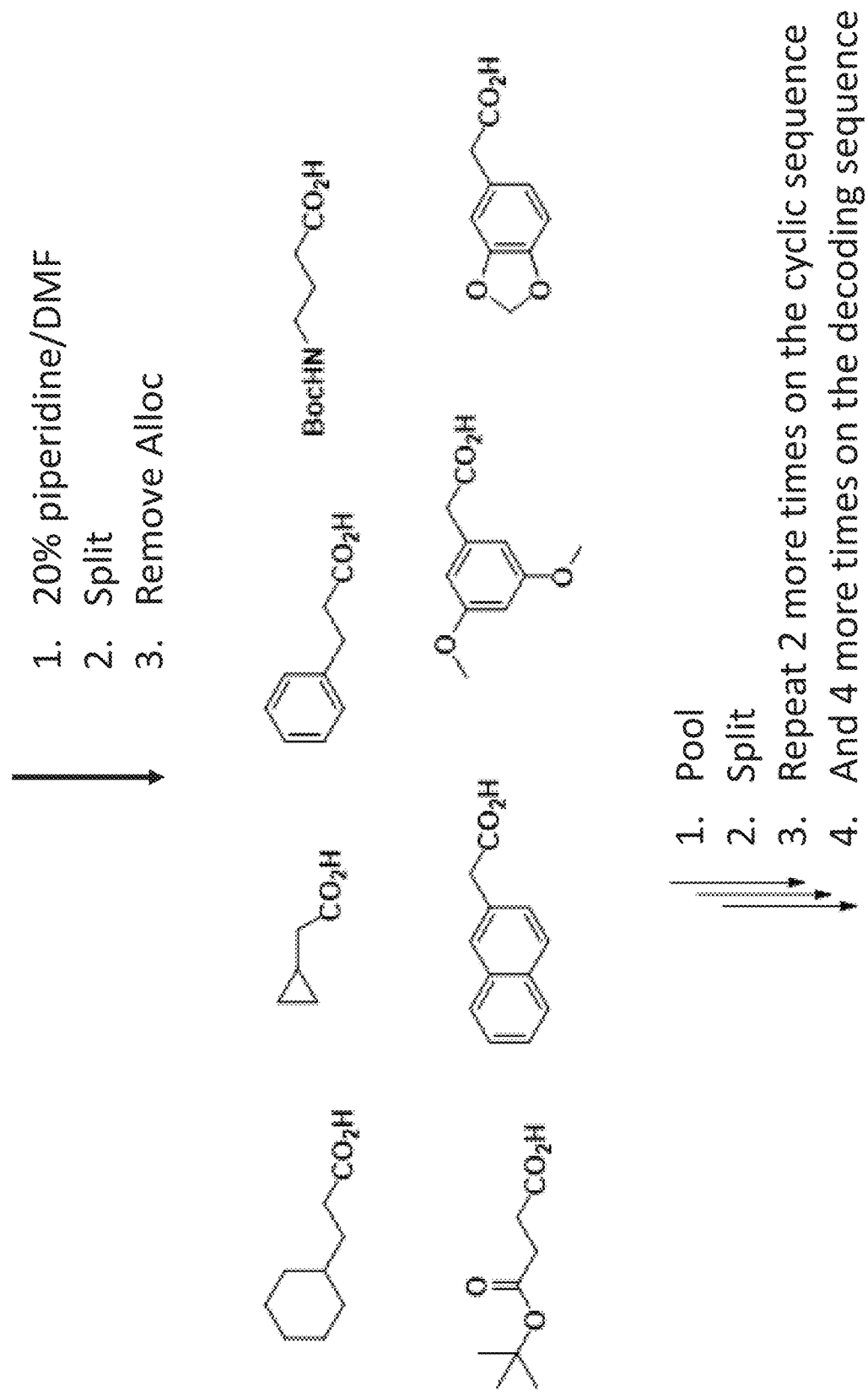
Figure 12:
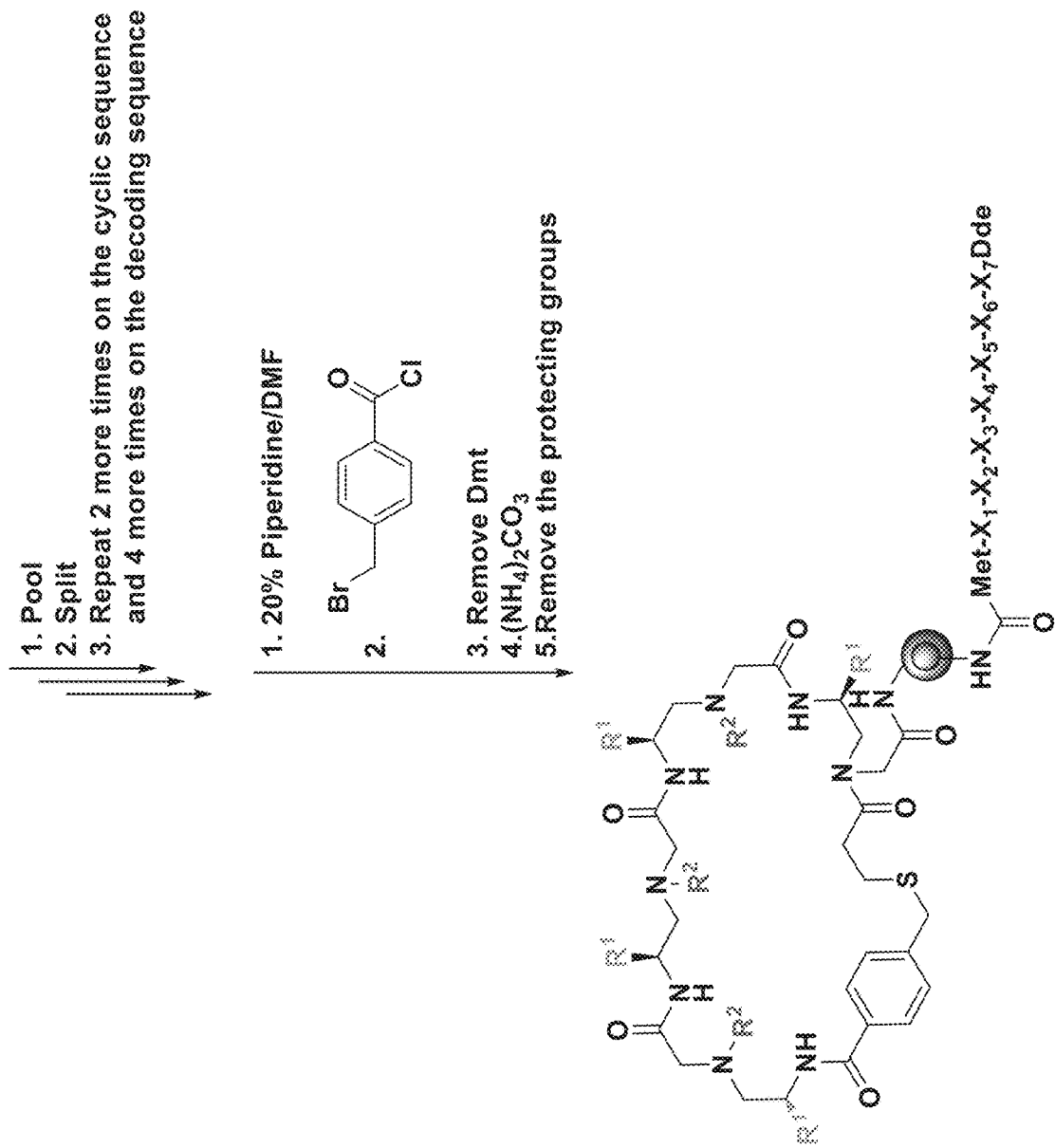
Figure 13:
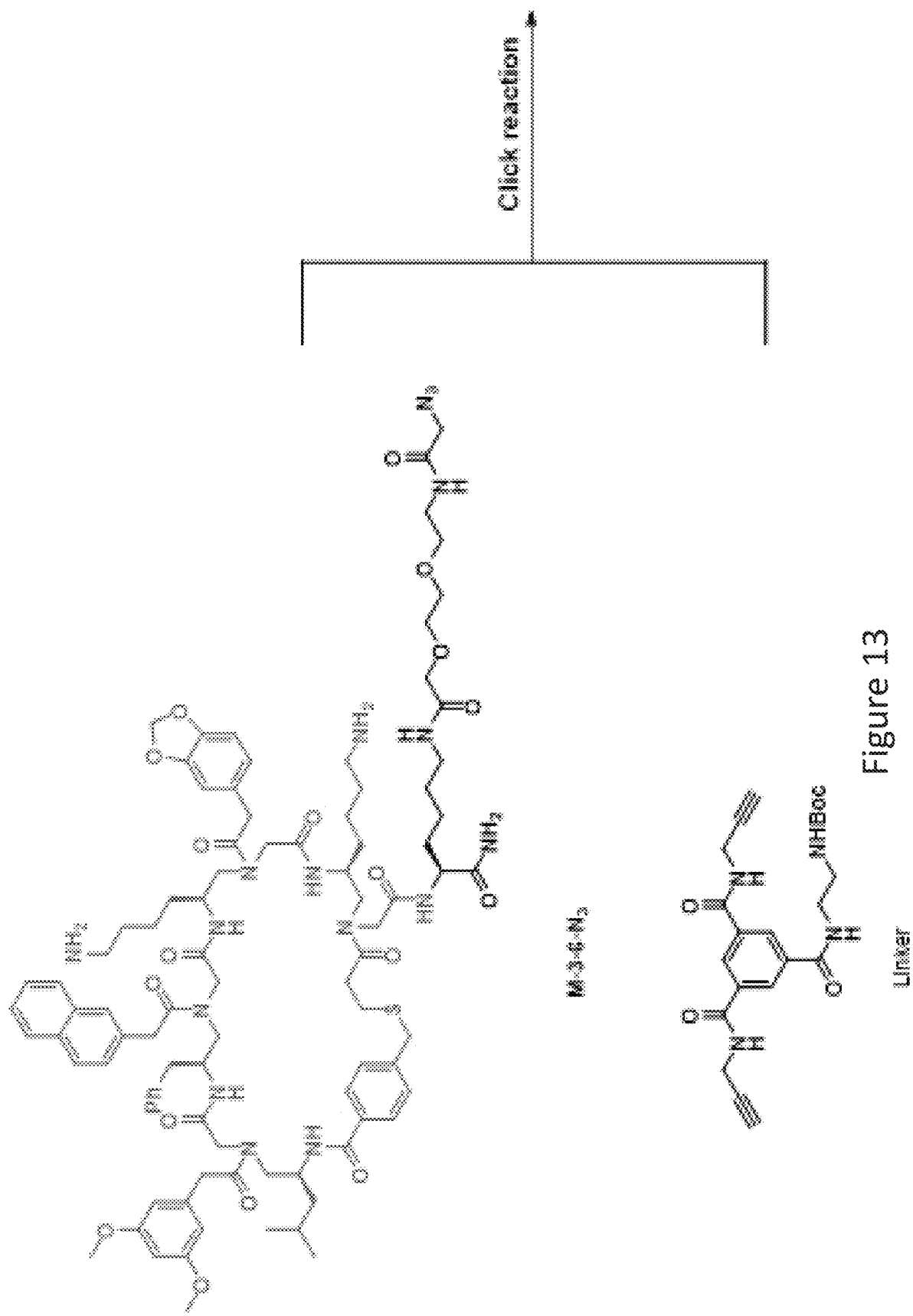
FIG. 13. The synthesis of M-3-6-D.
Figure 13:
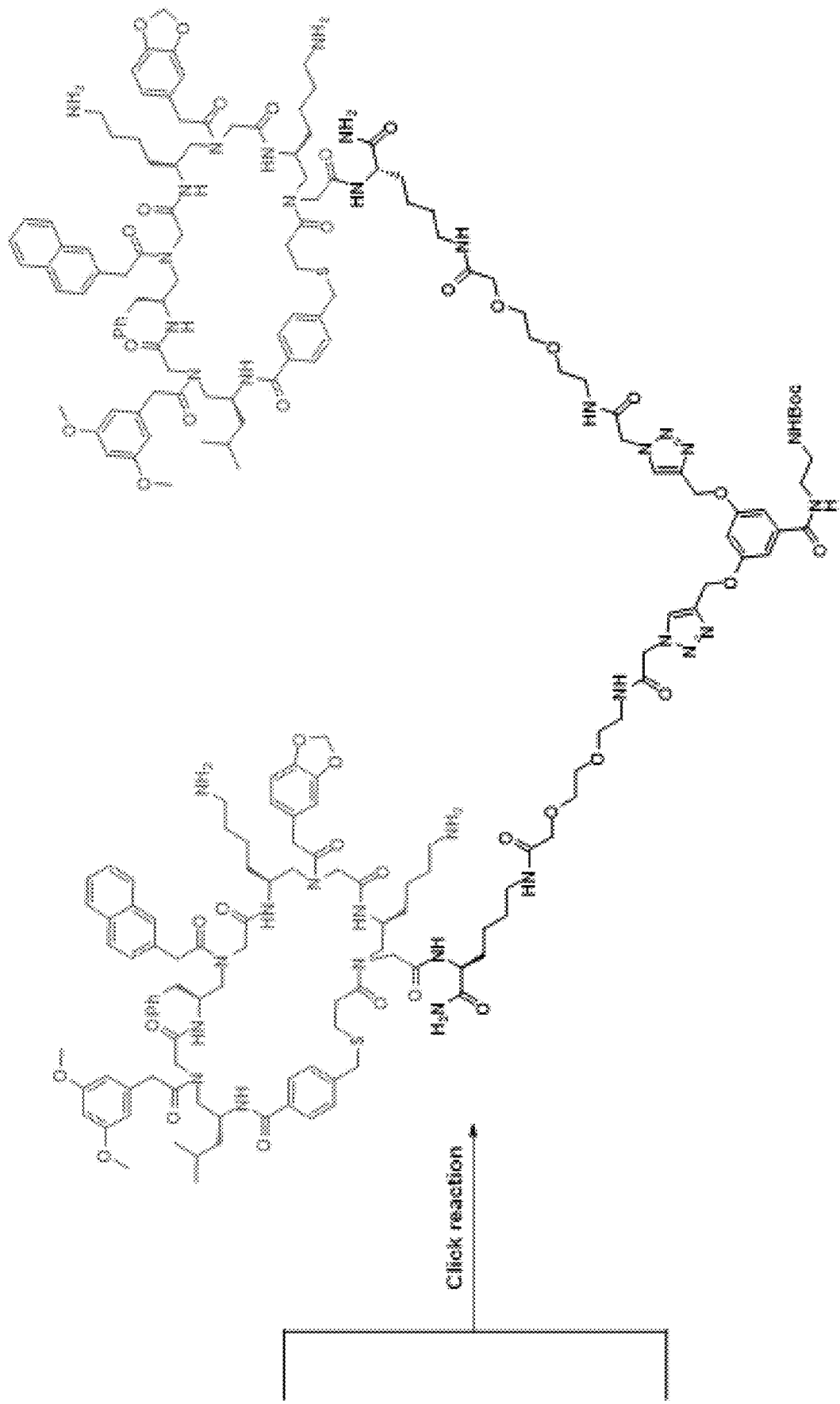
Figure 14:
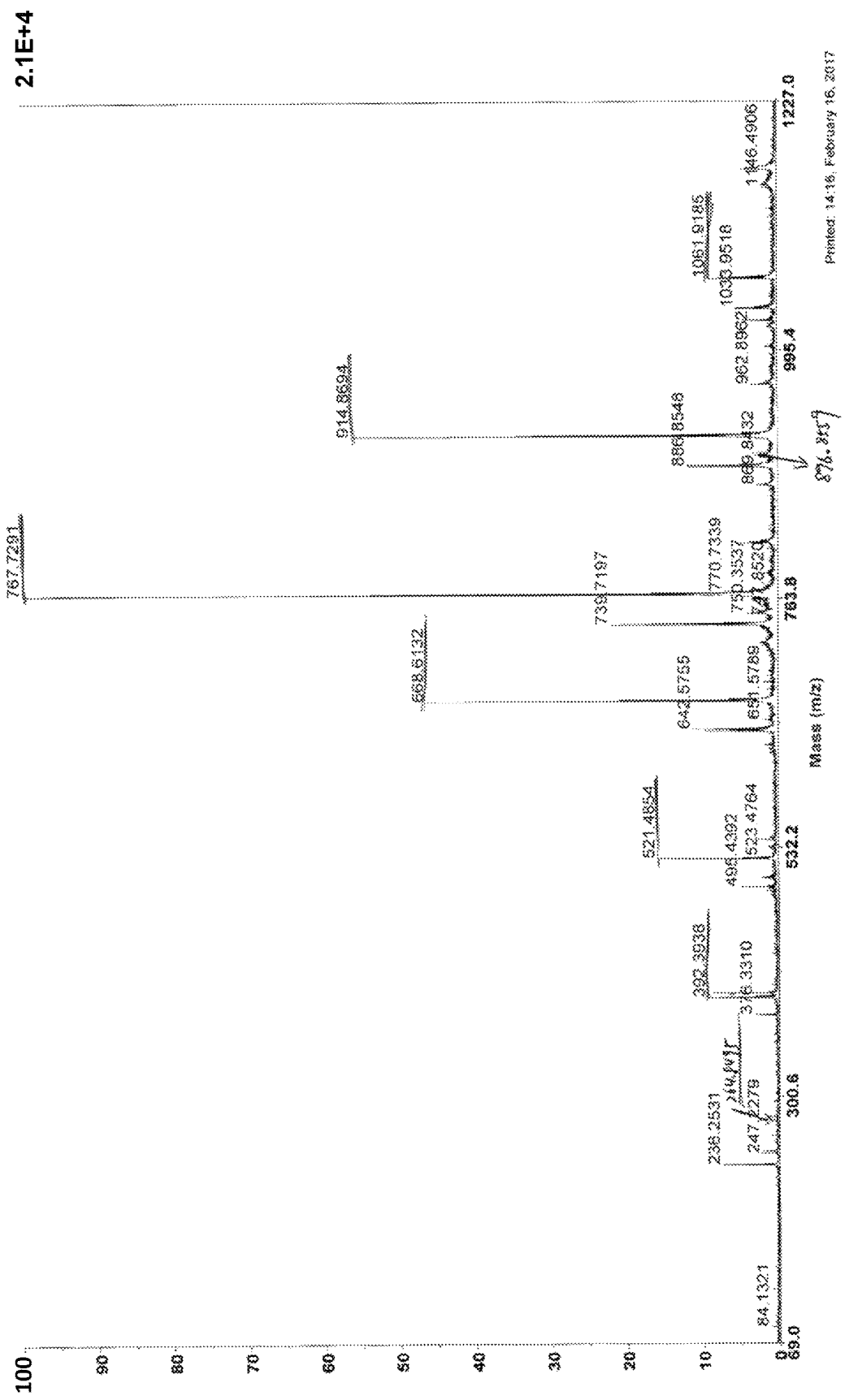
FIG. 14. Mass spectrometry analysis of disclosed compounds.
Figure 14:
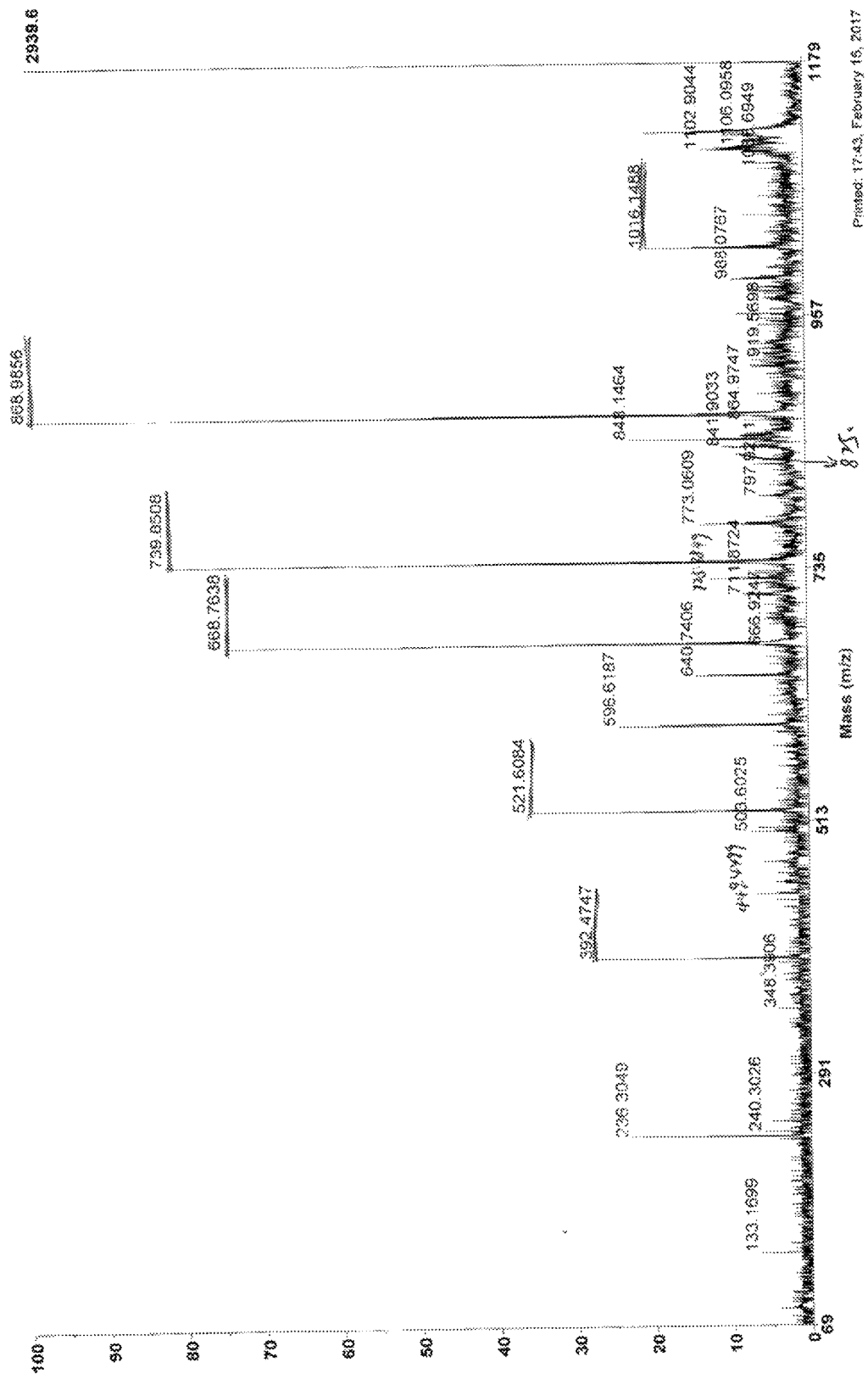
Figure 14:
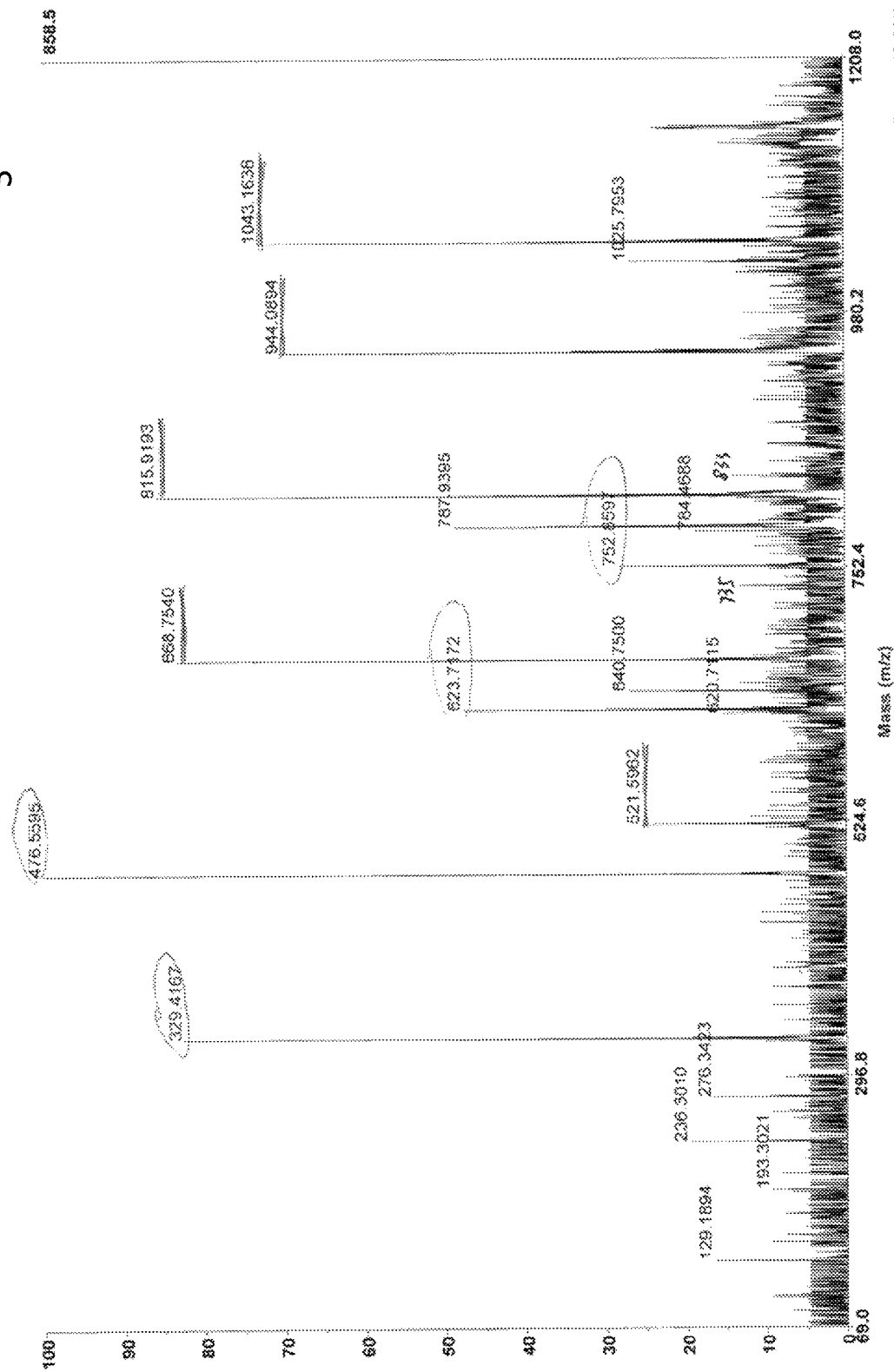
Figure 14:
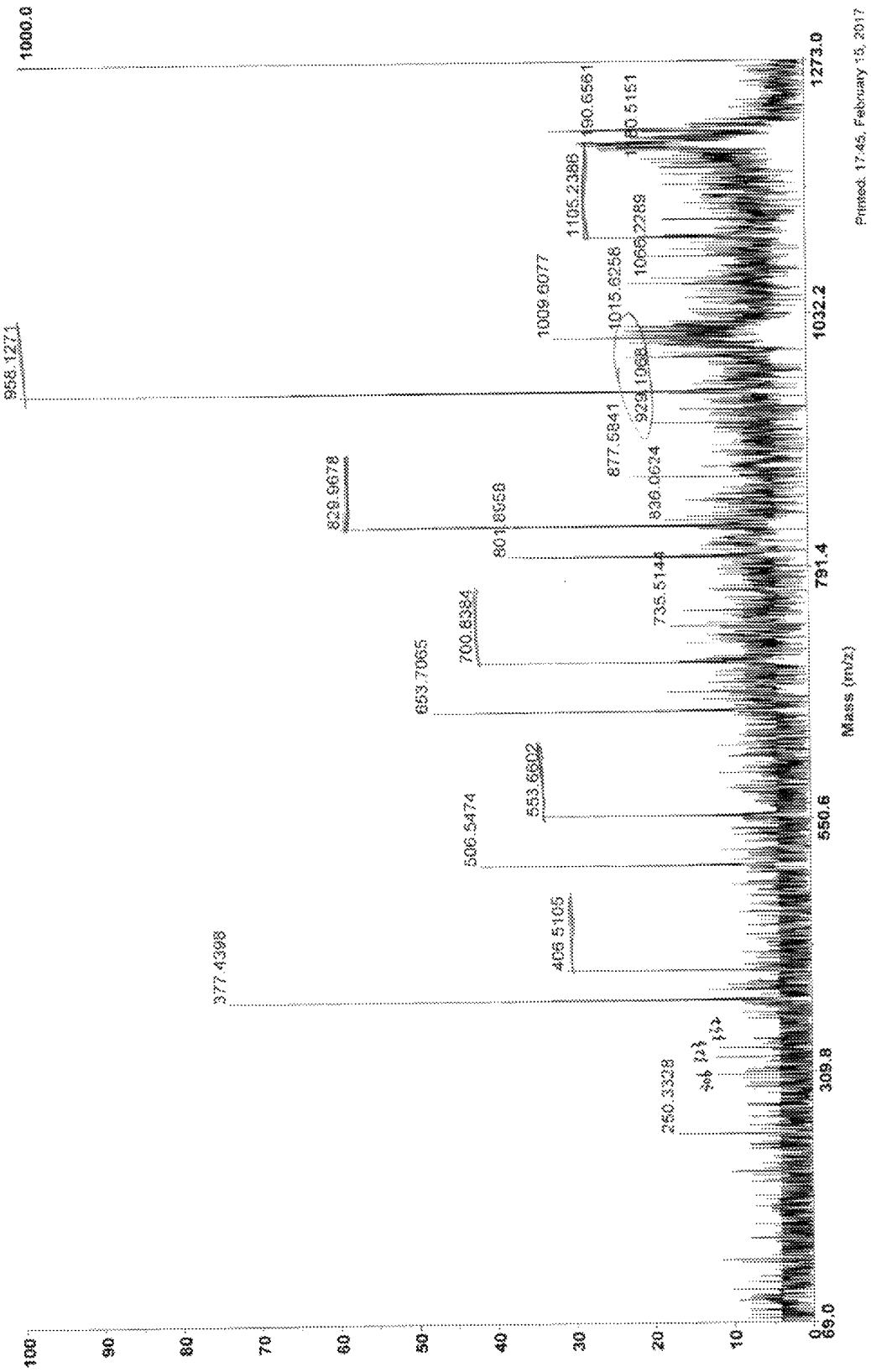
Figure 14:
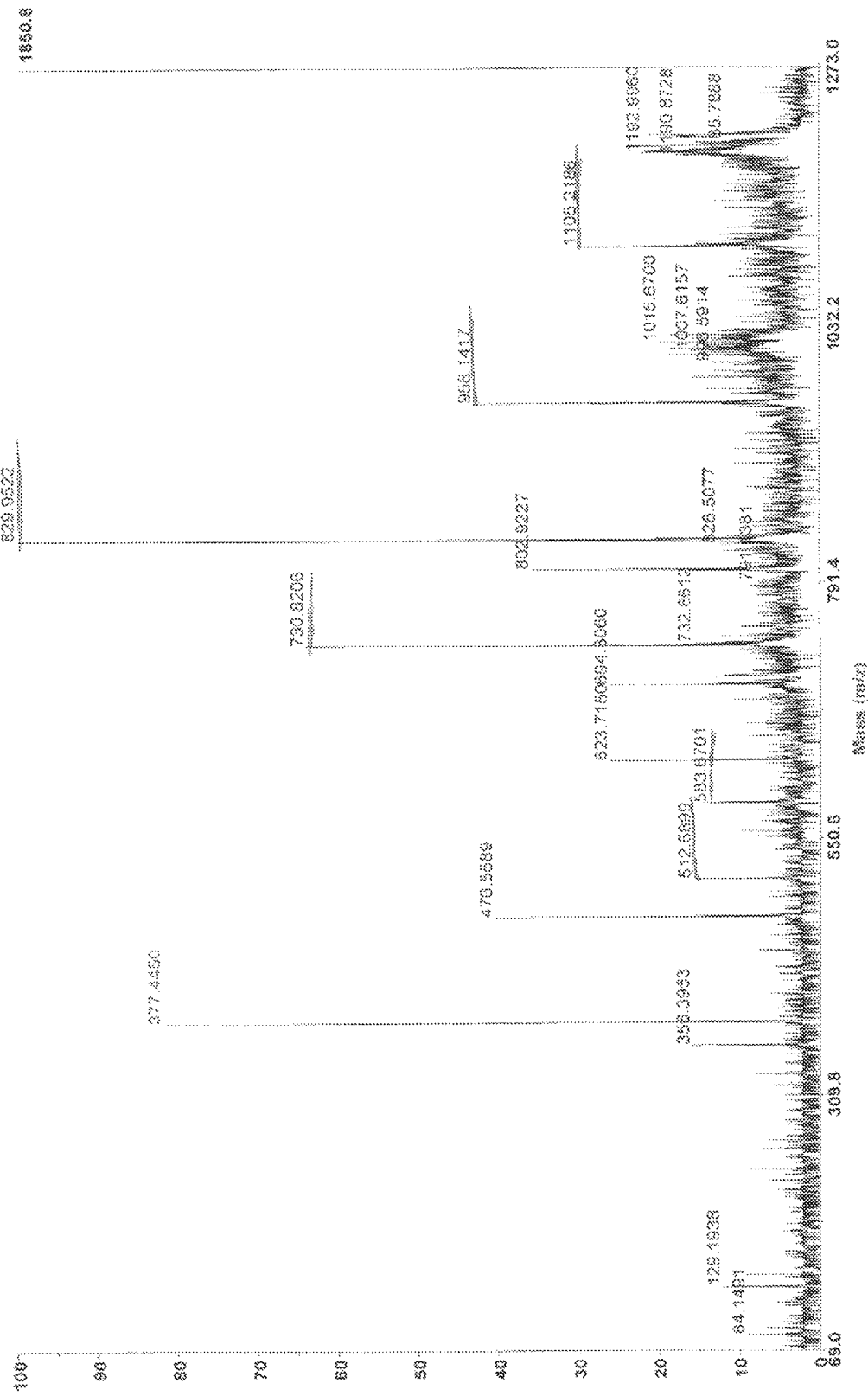
Figure 14:
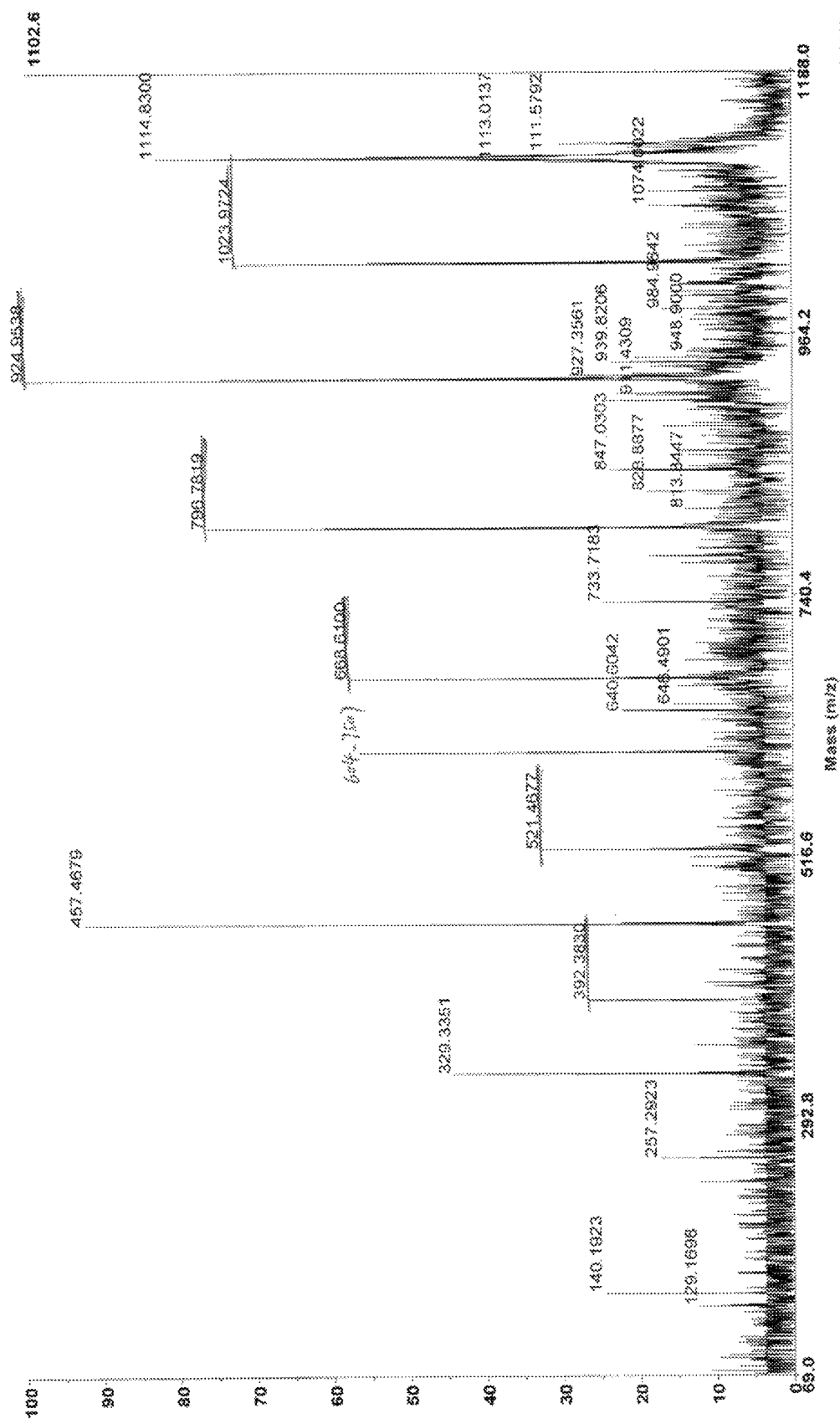
Figure 15:
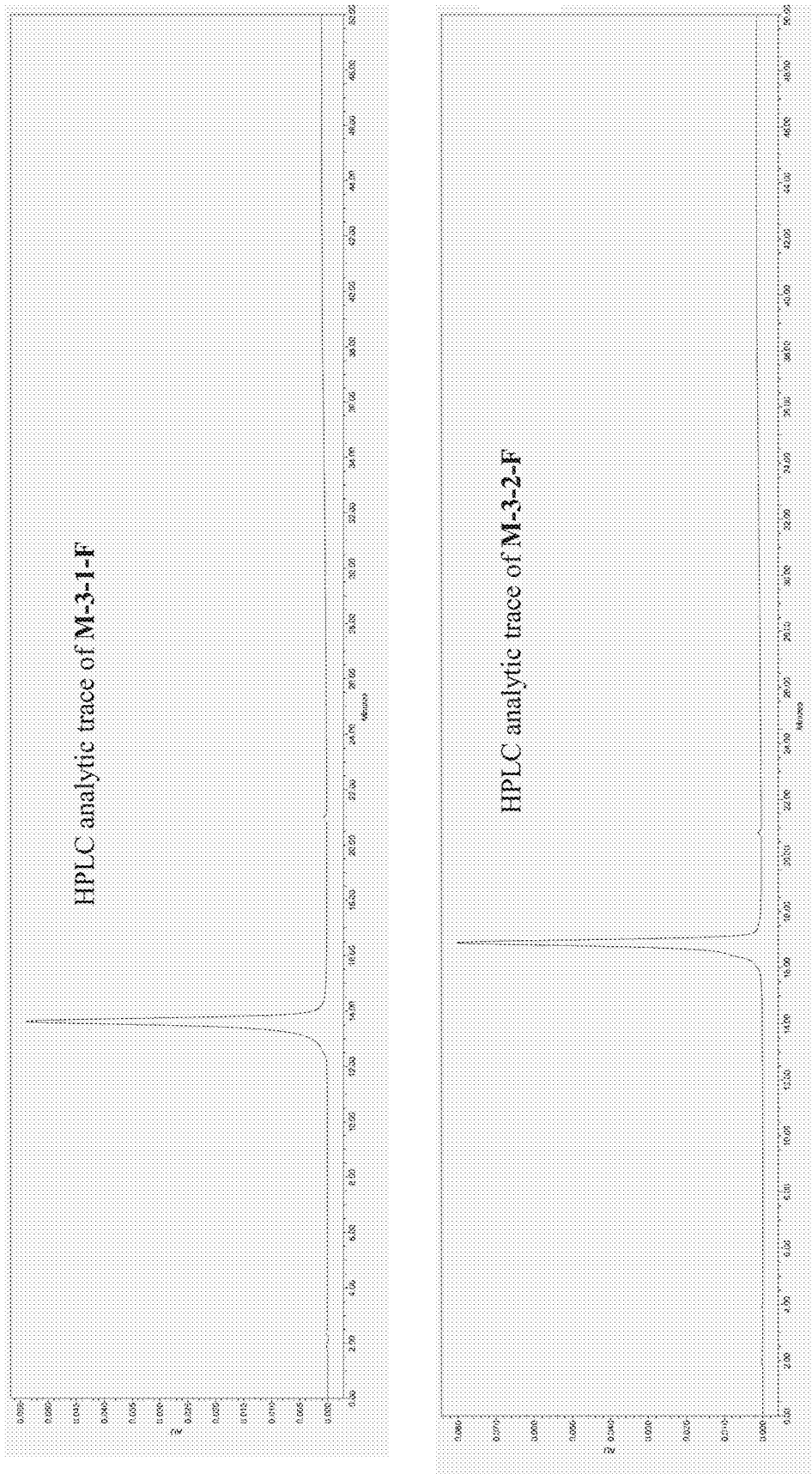
FIG. 15. HPLC trace of disclosed compounds.
Figure 15:
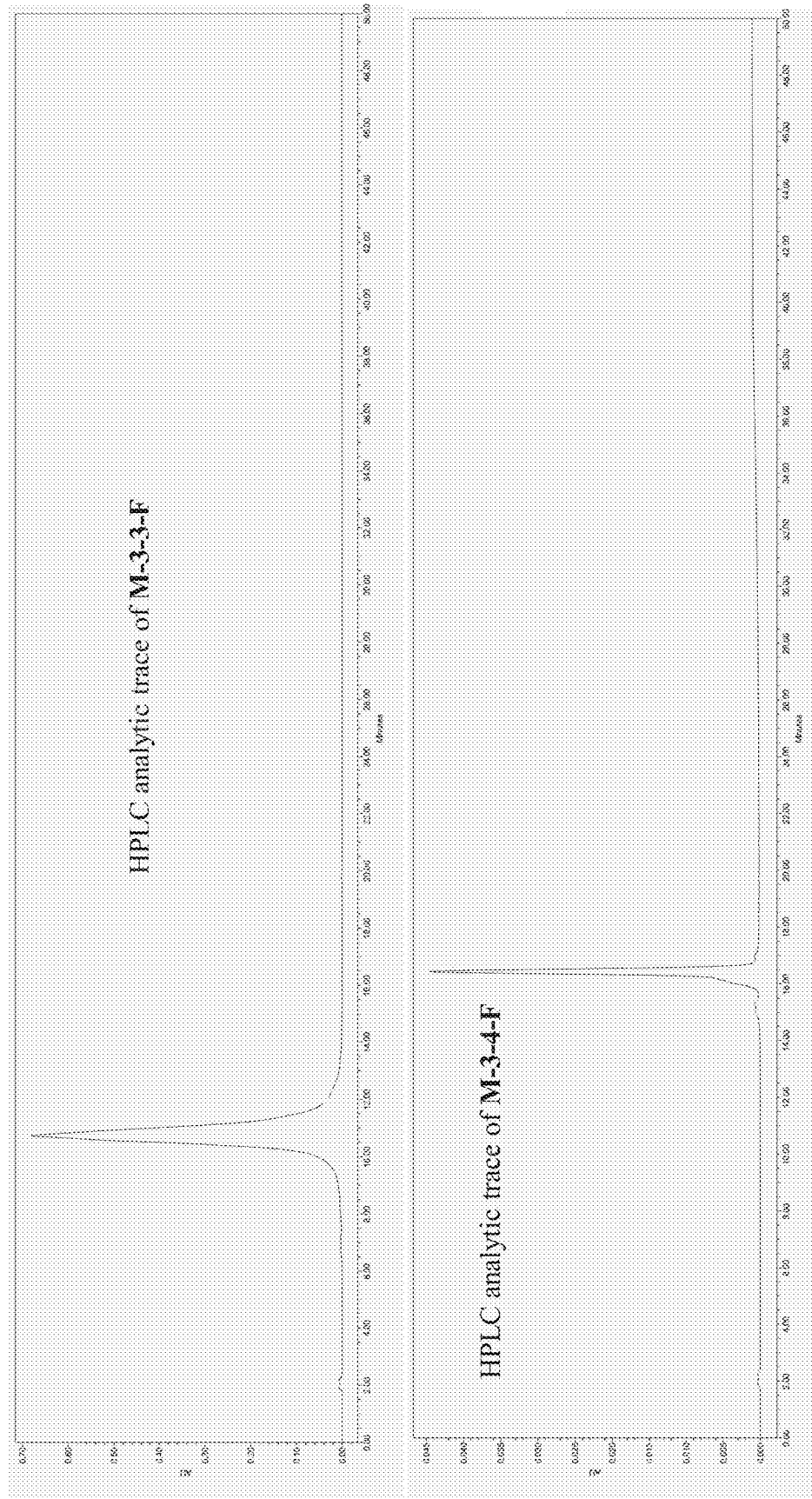
Figure 15:
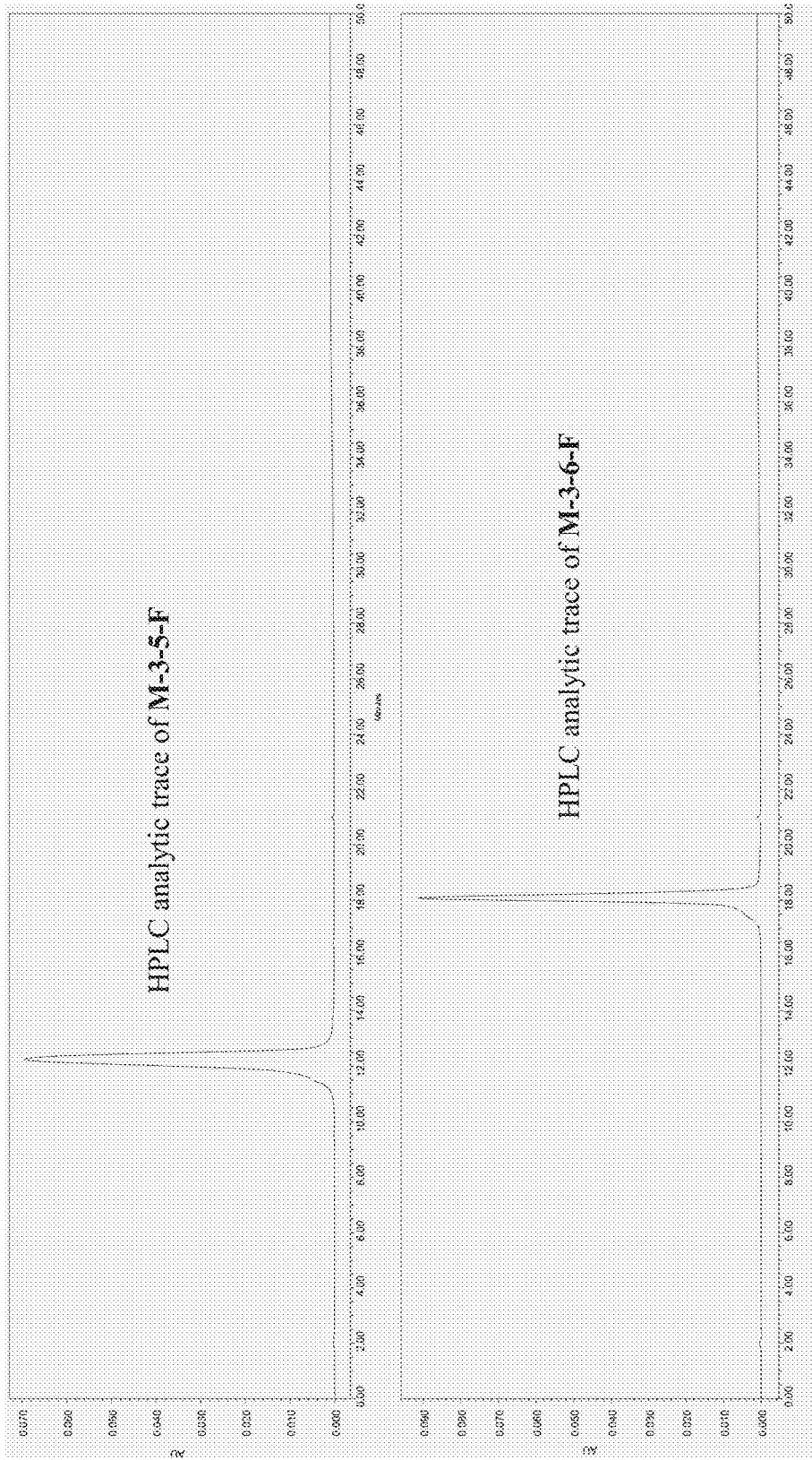
Figure 15:
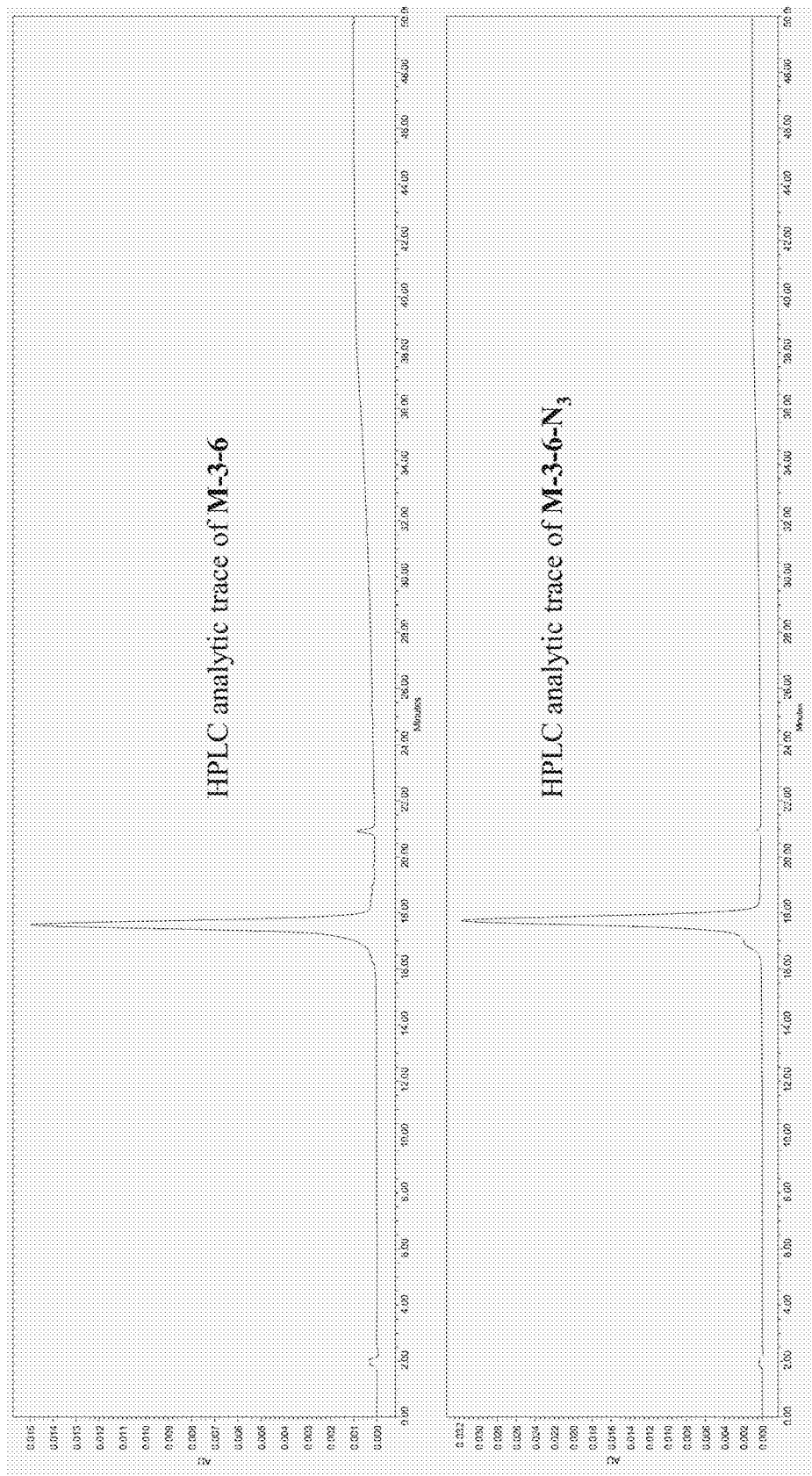
Figure 15:
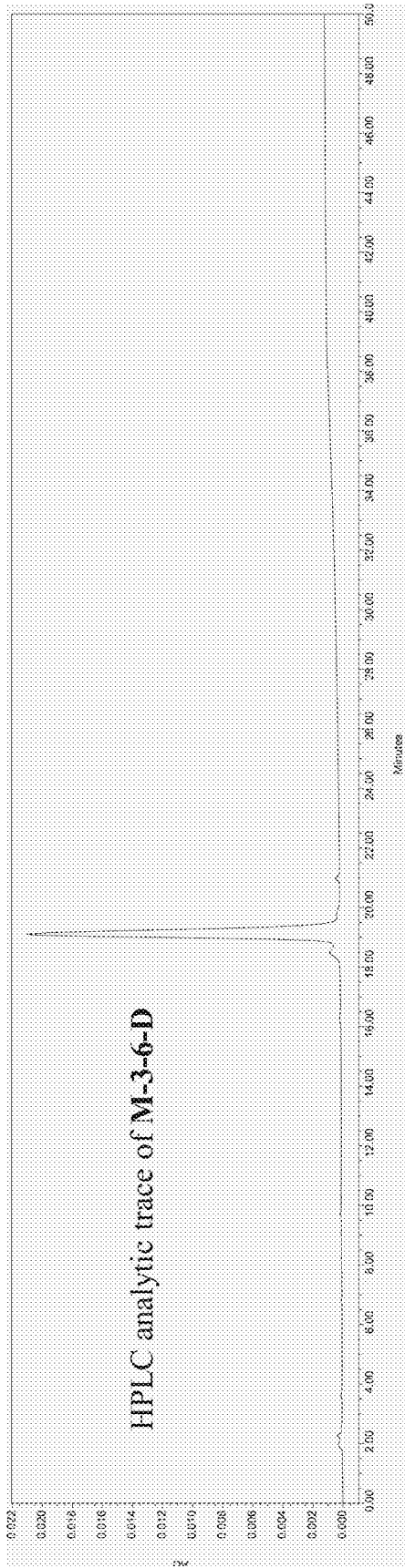

In one aspect of the current disclosure, cyclic γ-amino acid peptide compounds (cyclic γ-AAs) are provided. In some embodiments, the cyclic γ-AAs comprise a compound with the structure of formula (i):

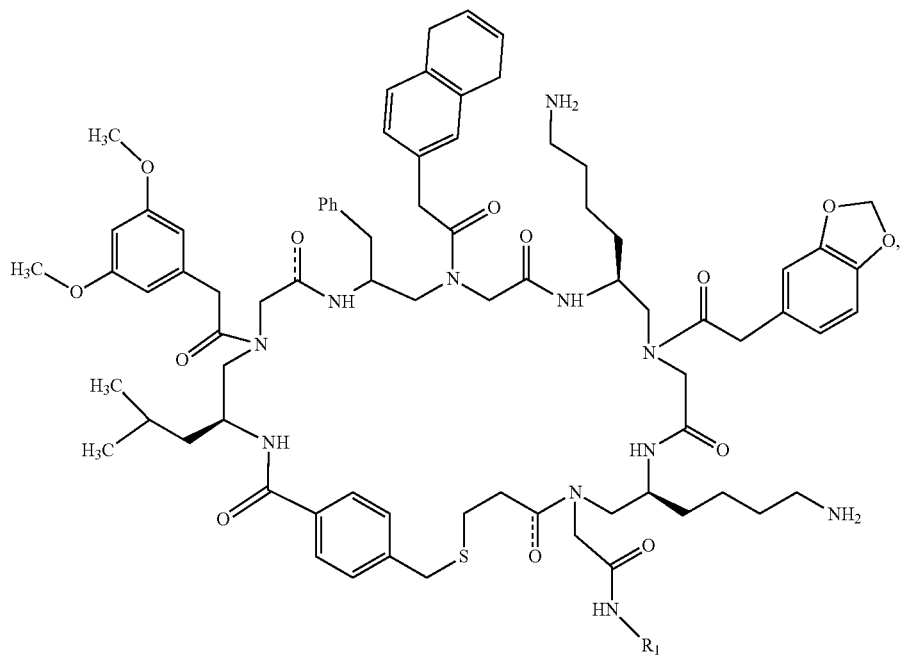

wherein R1 is H, a tag, a linker, a linker-tag complex, or a therapeutic moiety. In some embodiments, R1 comprises a tag. In other embodiments, R1 comprises a linker. In further embodiments, R1 comprises a linker-tag complex, including, but not limited to, multiple linkers, multiple tags, or combinations thereof. The inventors discovered that the cyclic γ-AA compound of formula (i), wherein R is H, had a dissociation constant ($K_d$) with HER2 of about 228 nM (FIG. 10). Accordingly, in some embodiments, the cyclic γ-AA compounds bind to HER2 with a dissociation constant ($K_d$) of less than about 250 nM, alternatively less than about 245 nM, alternatively less than about 240 nM, alternatively less than about 235 nM, or alternatively less than about 230 nM. In some embodiments, the cyclic γ-AA compounds bind to HER2 with a dissociation constant ($K_d$) of about 230 nM to about 30 nM. Suitably, a tag may comprise any chemical moiety which is readably detectable using conventional methods is further attached to the compound that allows for its purification, detection or use.

As used herein, a "tag" includes an atom, molecule, or compound that is useful in diagnosing, detecting or visualizing a location and/or quantity of a target molecule, cell, tissue, organ and the like. Tags that can be used in accordance with the embodiments herein include, but are not limited to, radioactive substances (e.g., radioisotopes, radionuclides, radiolabels or radiotracers), dyes, contrast agents, fluorescent compounds or molecules, bioluminescent compounds or molecules, enzymes and enhancing agents (e.g., paramagnetic ions). In addition, some nanoparticles, for example quantum dots and metal nanoparticles (described below) can be suitable for use as tags.

Exemplary radioactive substances that can be used as tags in accordance with the embodiments herein include, but are not limited to, $^{18}F$, $^{18}F$-FAC, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{75}Sc$, $^{77}As$, $^{86}Y$, $^{90}Y$, $^{89}Sr$, $^{89}Zr$, $^{94}Tx$, $^{94}TC$, $^{99}mTC$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-158}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$ and $^{225}Ac$. Exemplary Paramagnetic ions substances that can be used as tags include, but are not limited to ions of transition and lanthanide metals (e.g. metals having atomic numbers of 6 to 9, 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the tag is a radioactive metal or paramagnetic ion, in some embodiments, the marker can be reacted with a reagent having a long tail with one or more chelating groups attached to the long tail for binding these ions. The long tail can be a polymer such as a polylysine, polysaccharide, or other derivatized or derivatizable chain having pendant groups to which may be bound to a chelating group for binding the ions. Examples of chelating groups that may be used according to the embodiments herein include, but are not limited to, ethylenediaminetetraacetic acid (EDTA), diethylenetriaminepentaacetic acid (DTPA), DOTA, NOTA, NOGADA, NETA, deferoxamine (DfO), porphyrins, polyamines, crown ethers, bis-thiosemicarbazones, polyoximes, and like groups. The chelate can be linked to the antigen binding construct by a group which allows formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antigen binding constructs and carriers described herein. Macrocyclic chelates such as NOTA, NOGADA, DOTA, and TETA are of use with a variety of metals and radiometals including, but not limited to, radionuclides of gallium, yttrium and copper, respectively. Other ring-type chelates such as macrocyclic polyethers, which are of interest for stably binding radionuclides, such as Radium-223 for RAIT may be used. In certain embodiments, chelating moieties may be used to attach a PET imaging agent, such as an Aluminum-$^{18}F$ complex, to a targeting molecule for use in PET analysis.

Exemplary contrast agents that can be used as tags in accordance with the embodiments of the disclosure include, but are not limited to, barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

Bioluminescent and fluorescent compounds or molecules and dyes that can be used as tags in accordance with the embodiments of the disclosure include, but are not limited to, fluorescein, fluorescein isothiocyanate (FITC), OREGON GREEN™, rhodamine, Texas red, tetrarhodimine isothiocynate (TRITC), Cy3, Cy5, and the like), fluorescent markers (e.g., green fluorescent protein (GFP), phycoerythrin, and the like), autoquenched fluorescent compounds that are activated by tumor-associated proteases, enzymes (e.g., luciferase, horseradish peroxidase, alkaline phosphatase, and the like), nanoparticles, biotin, digoxigenin or combination thereof.

Enzymes that can be used as tags in accordance with the embodiments of the disclosure include, but are not limited to, horseradish peroxidase, alkaline phosphatase, acid phosphatase, glucose oxidase, β-galactosidase, β-glucoronidase or β-lactamase. Such enzymes may be used in combination with a chromogen, a fluorogenic compound or a luminogenic compound to generate a detectable signal.

In some embodiments, the compound is conjugated to a nanoparticle. The term "nanoparticle" refers to a microscopic particle whose size is measured in nanometers, e.g., a particle with at least one dimension less than about 100 nm. Nanoparticles can be used as detectable substances because they are small enough to scatter visible light rather than absorb it. For example, gold nanoparticles possess significant visible light extinction properties and appear deep red to black in solution. As a result, compositions comprising antigen binding constructs conjugated to nanoparticles can be used for the imaging of HER2 in a subject. At the small end of the size range, nanoparticles are often referred to as clusters. Metal, dielectric, and semiconductor nanoparticles have been formed, as well as hybrid structures (e.g. core-shell nanoparticles). Nanospheres, nanorods, and nanocups are just a few of the shapes that have been grown. Semiconductor quantum dots and nanocrystals are examples of additional types of nanoparticles. Such nanoscale particles, when conjugated to an antigen binding construct, can be used as imaging agents for the detection of HER2 as described herein.

In some embodiments, the cyclic γ-AAs comprise formula (i) wherein R1 comprises the fluorescent molecule FITC attached by a linker, e.g., the compound having the structure of formula (ii):

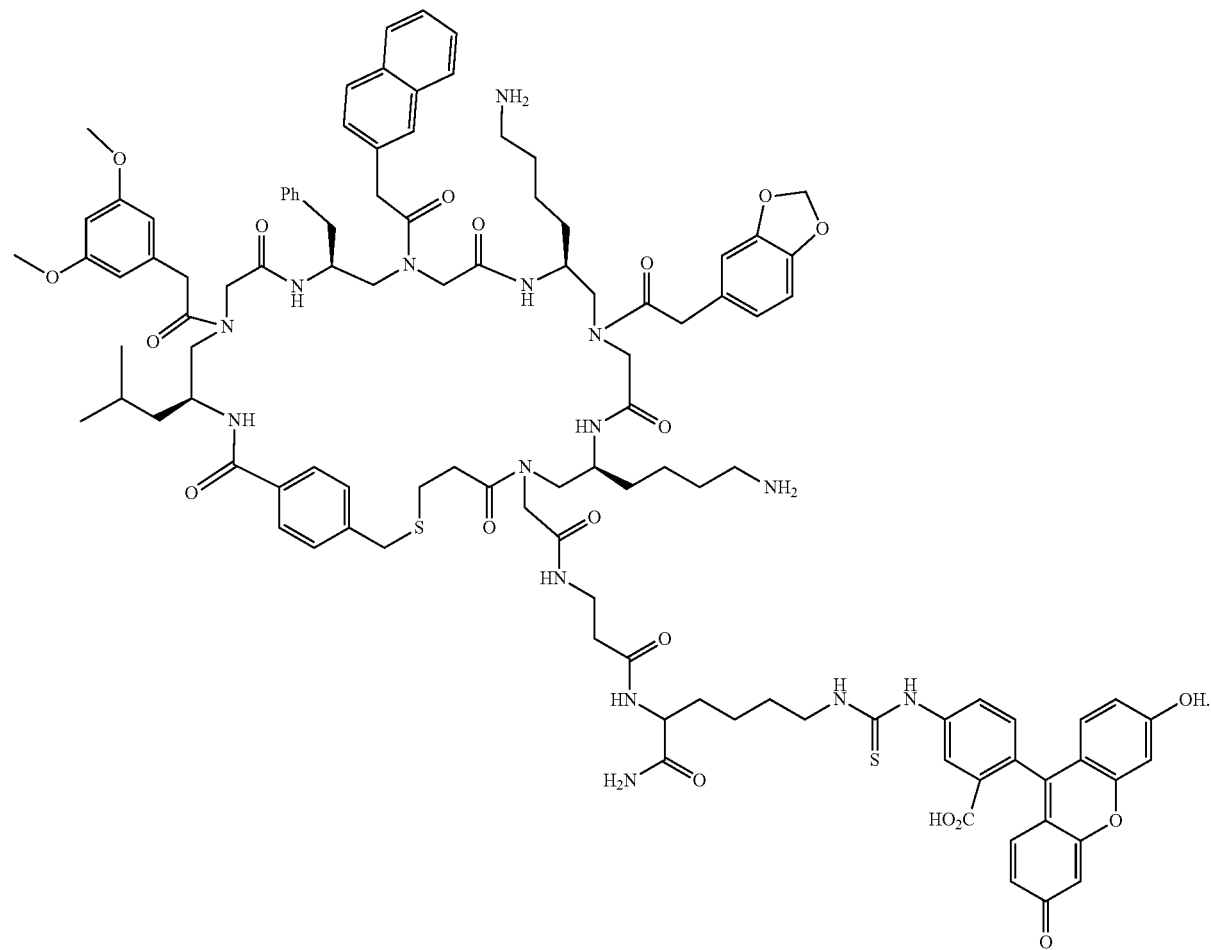

In some embodiments, R1 comprises a linker. As used herein, "linker" refers to a chemical moiety which serves a structural purpose, for example, to properly position the molecule in proximity to another molecule or moiety, or to attach the compound of formula (i) to another compound or moiety, or attach the compound of formula (i) to another molecule of the compound of formula (i). Exemplary linkers include an unsubstituted $C_1$-$C_{20}$ alkyl, substituted $C_1$-$C_{20}$ alkyl, $C_2$-$C_{20}$ alkenyl, phenyl, phenyl substituted $C_1$-$C_{20}$ alkyl, cycloalkyl substituted $C_1$-$C_{20}$ alkyl, an amino acid, and polyethylene glycol (PEG).

In some embodiments, R1 is a linker comprising azide, e.g., the compound of formula (iii):

the current disclosure, dimeric compounds are provided. In some embodiments, the dimeric compounds comprise two molecules of formula (i). In some embodiments, the structure of the dimeric compound is formula (i)-linker-formula (i), wherein the first and second formula (i) compounds are linked via a linker through R1. The linker may contain one or more linkers and/or molecules.

In some embodiments, the molecule of formula (i), wherein R1 comprises azide, e.g., the molecule of formula (iii), is reacted with a bidentate alkyne to generate a dimeric compound. In some embodiments, the bidentate alkyne comprises the molecule with the structure of formula (v)

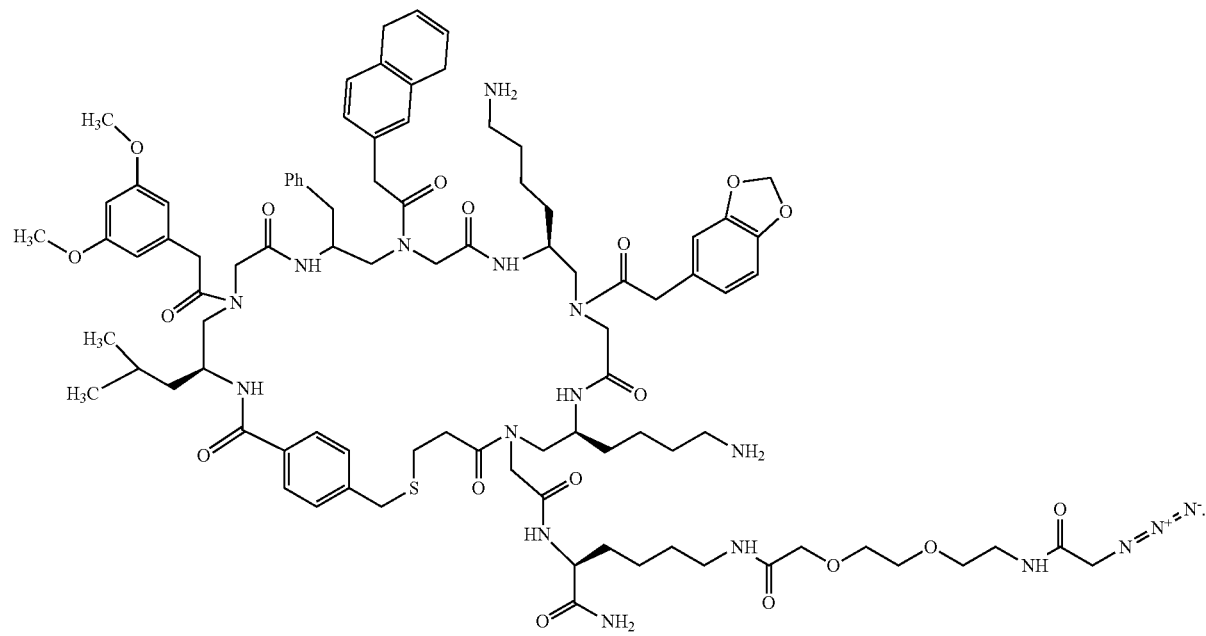

In some further embodiments, the compound of formula (i) may further comprise R1 being a linker and a pharmaceutical agent.

In another embodiment, the compound comprises two compounds of formula (i) linked by one or more linkers and/or molecules. Without being limited by any theory or mechanism, the inventors hypothesized that the compound of formula (i) may have increased binding to HER2 when dimerized by an appropriate linker, generating a structure similar to an antibody with two "antigen recoginition domains", i.e., the cyclic γ-AAs specific for HER2 of the instant disclosure, linked together. Thus, in another aspect of

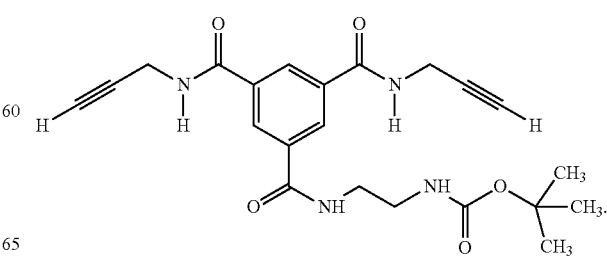

In some embodiments, the dimeric compound has the structure of formula (iv):

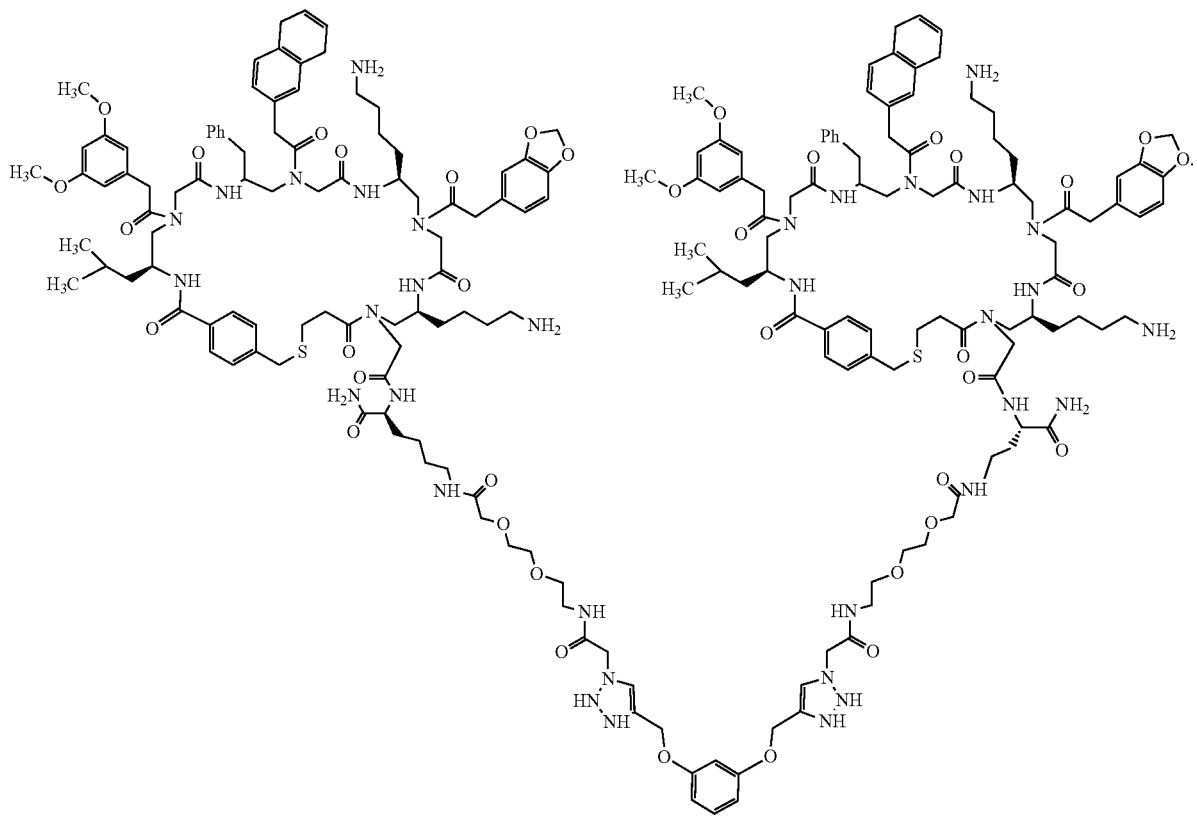 [SMILES: COc1cc(CC(=O)N2CC(=O)NC(Cc3ccccc3)CN(C(=O)Cc3ccc4c(c3)CC=CC4)CC(=O)N[C@@H](CCCCN)CN(C(=O)Cc3ccc4c(c3)OCO4)CC(=O)N[C@@H](CCCCN)CN(CC(=O)N[C@@H](CCCCNC(=O)COCCOCCNC(=O)CN3C=C(COc4cccc(OCC5=CN(CC(=O)NCCOCCOCC(=O)NCC[C@H](NC(=O)CN6C[C@H](CCCCN)NC(=O)CN(C(=O)Cc7ccc8c(c7)OCO8)C[C@H](CCCCN)NC(=O)CN(C(=O)Cc7ccc8c(c7)CC=CC8)CC(Cc7ccccc7)NC(=O)CN(C(=O)Cc7cc(OC)cc(OC)c7)C[C@H](CC(C)C)NC(=O)c7ccc(cc7)CSCCC6=O)C(N)=O)NN5)c4)NN3)C(N)=O)C(=O)CCSCc3ccc(cc3)C(=O)N[C@@H](CC(C)C)C2)cc(OC)c1]

Figure 5:
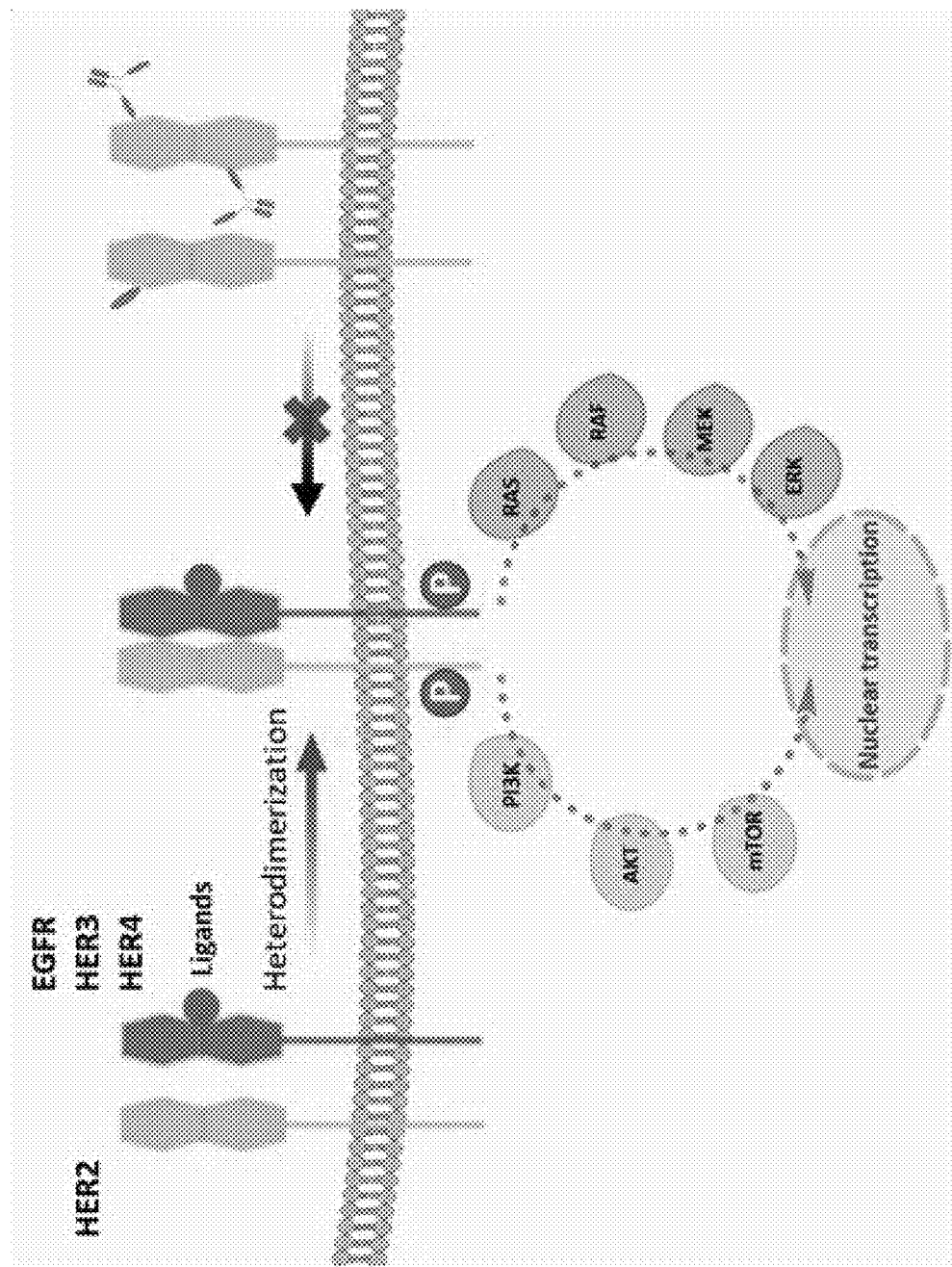
FIG. 5. (A) Signal transduction pathway mediated by HER2 and proposed inhibition by cyclic peptides monomer and dimer. (B) Western blot analyses of SKBR3 cell lysates following M-3-6 incubation in vitro. M-3-6 treatment resulted in a dose-dependent inhibition of HER2 receptor phosphorylation and a reduction in the phosphorylation of AKT and ERK, downstream signaling of HER2. (C) Western blot analyses of SKBR3 cell lysates following M-3-6-D incubation in vitro. M-3-6-D treatment resulted in a much more effective phosphorylation inhibition compared with M-3-6. (D) M-3-6 and M-3-6-D inhibit cell proliferation in vitro. EGF-driven proliferation of SKBR3 cells was analyzed by CCK-8 proliferation assay. EGF (100 ng/mL) induced the proliferation of cells under serum-starved conditions (###, $P<0.001$ vs. non-stimulated cells), and both M-3-6 and M-3-6-D inhibited EGF-induced proliferation significantly in a dose-dependent manner (*, $P<0.05$ vs. EGF-stimulated cells, ***, $P<0.001$ vs. EGF-stimulated cells).
Figure 5:
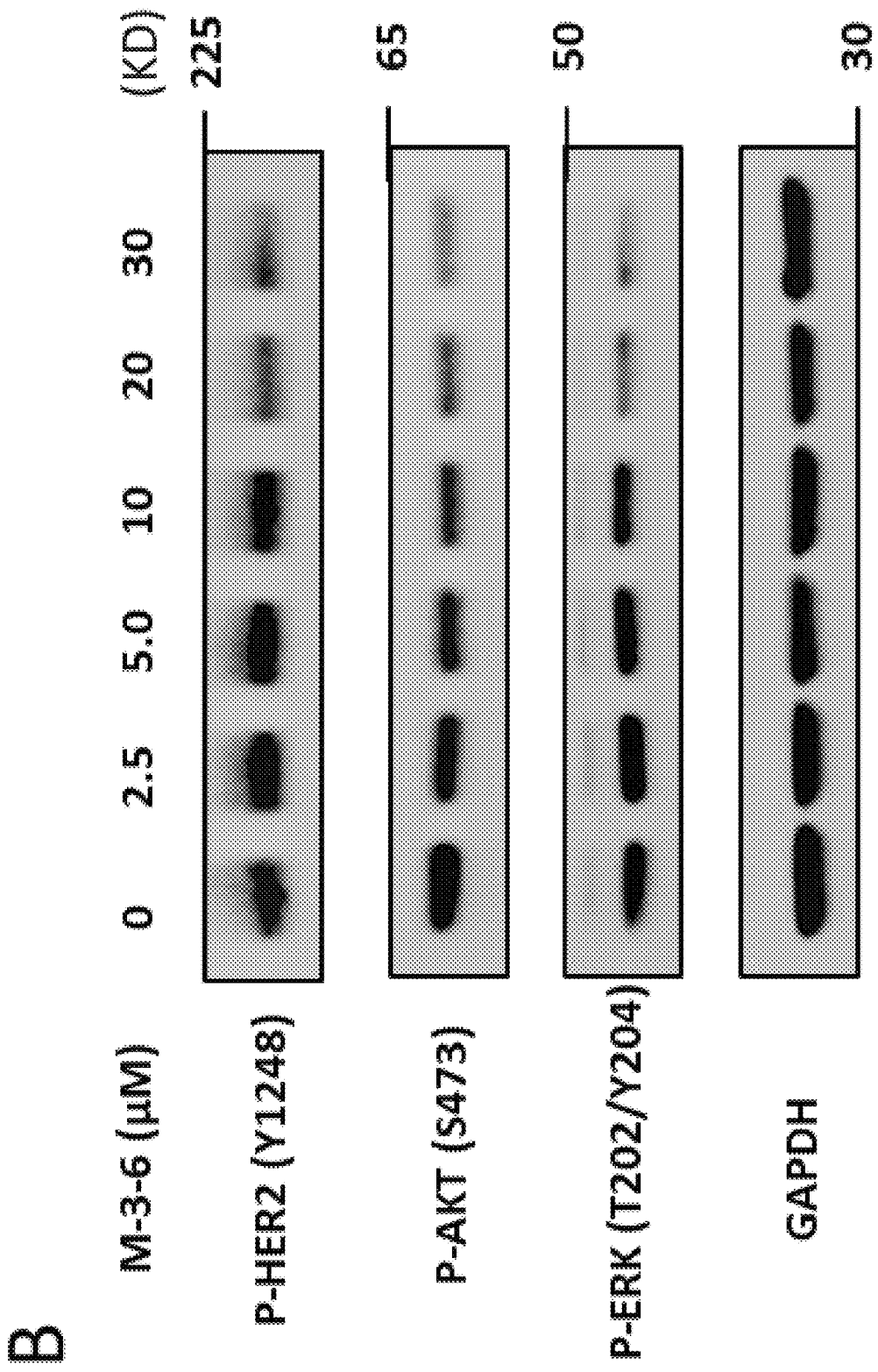
Figure 5:
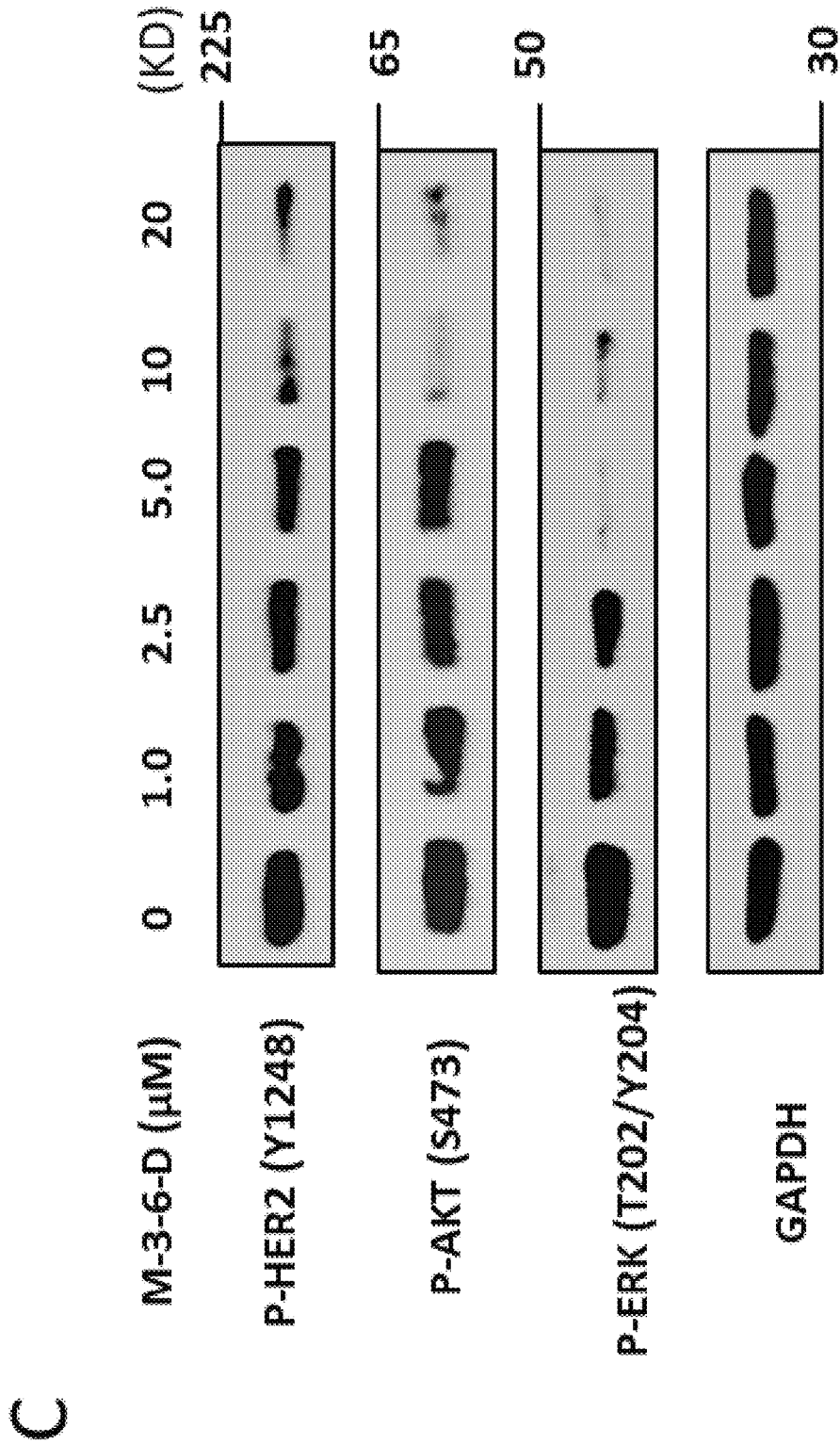
Figure 5:
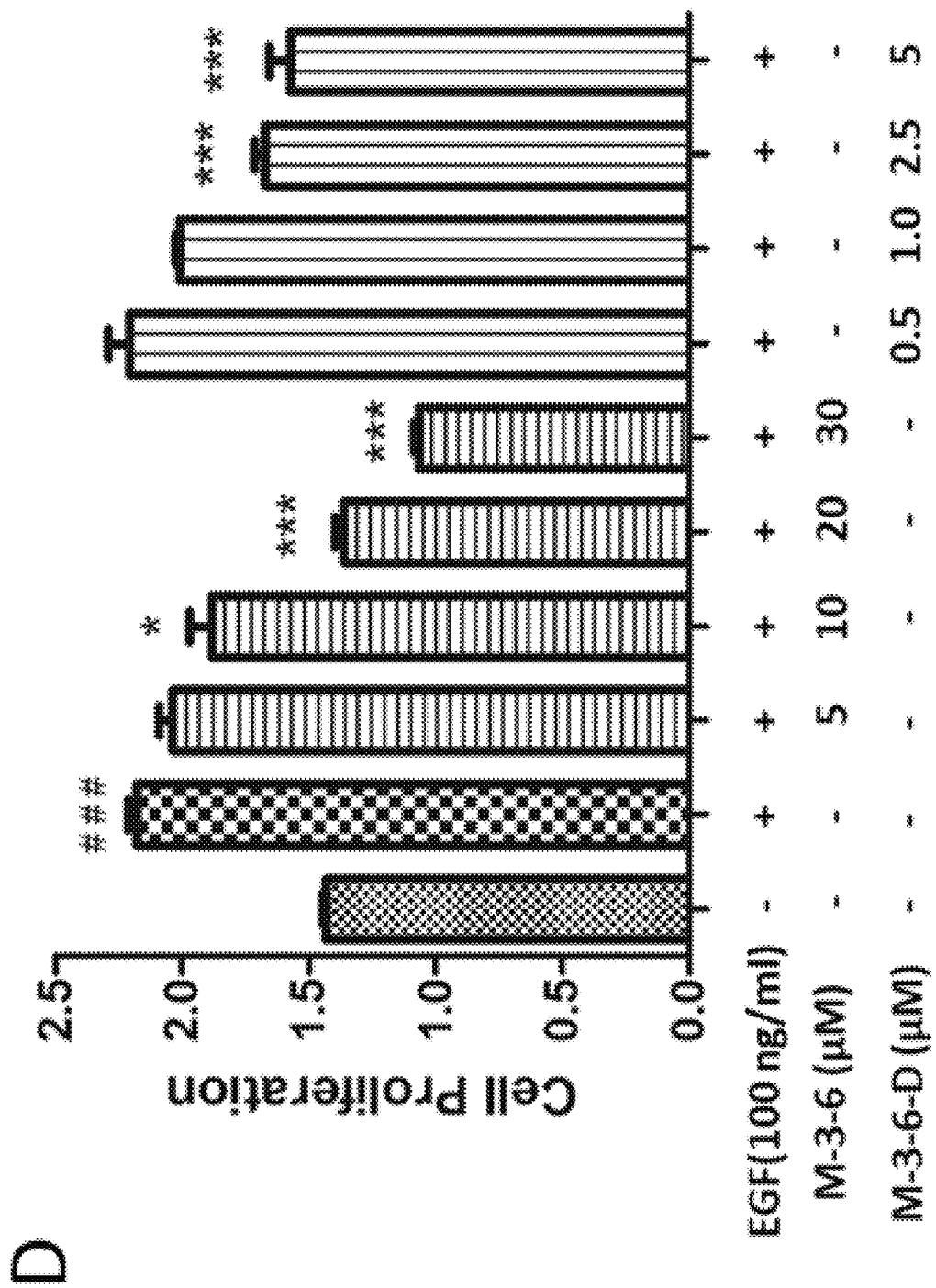
Figure 6:
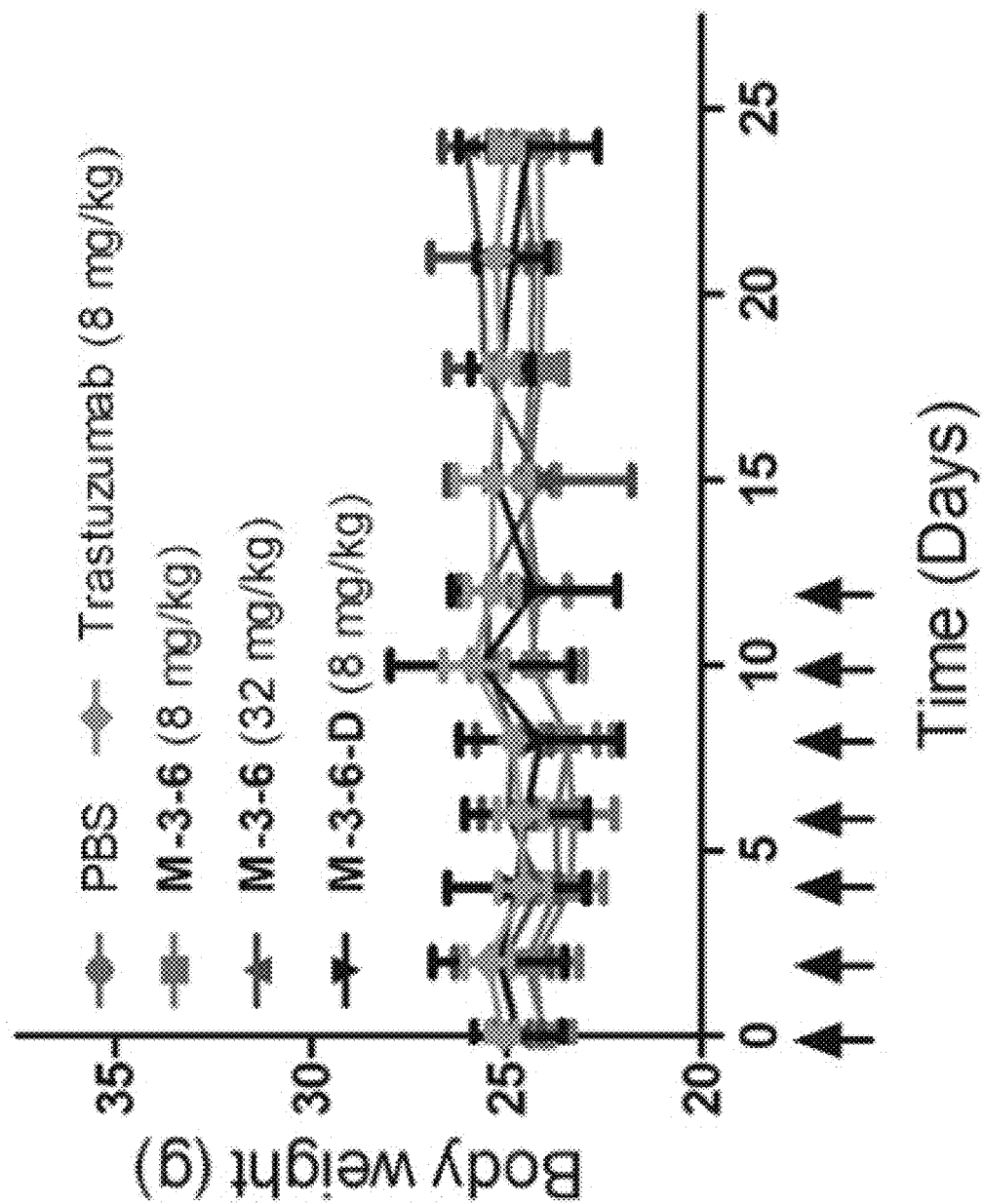
FIG. 6. Therapeutic efficacy of M-3-6 and M-3-6-D in SKBR3 xenograft models. (A) Mice body weight shift curve of the mice during the experiment. Arrows indicate the time of compounds treatment. (B) Time course assessment of total tumor volume. The day when treatment started was recorded as day 0 and arrows indicate the time of injection. After 2 weeks injection, tumor volume was measured once every 3 days until day 24. (C) Immunohistochemical staining for P-HER2, P-AKT and P-ERK. Representative staining of section from SKBR3 tumors with antibodies against the indicated proteins. Scale bar: 100 nm.
Figure 6:
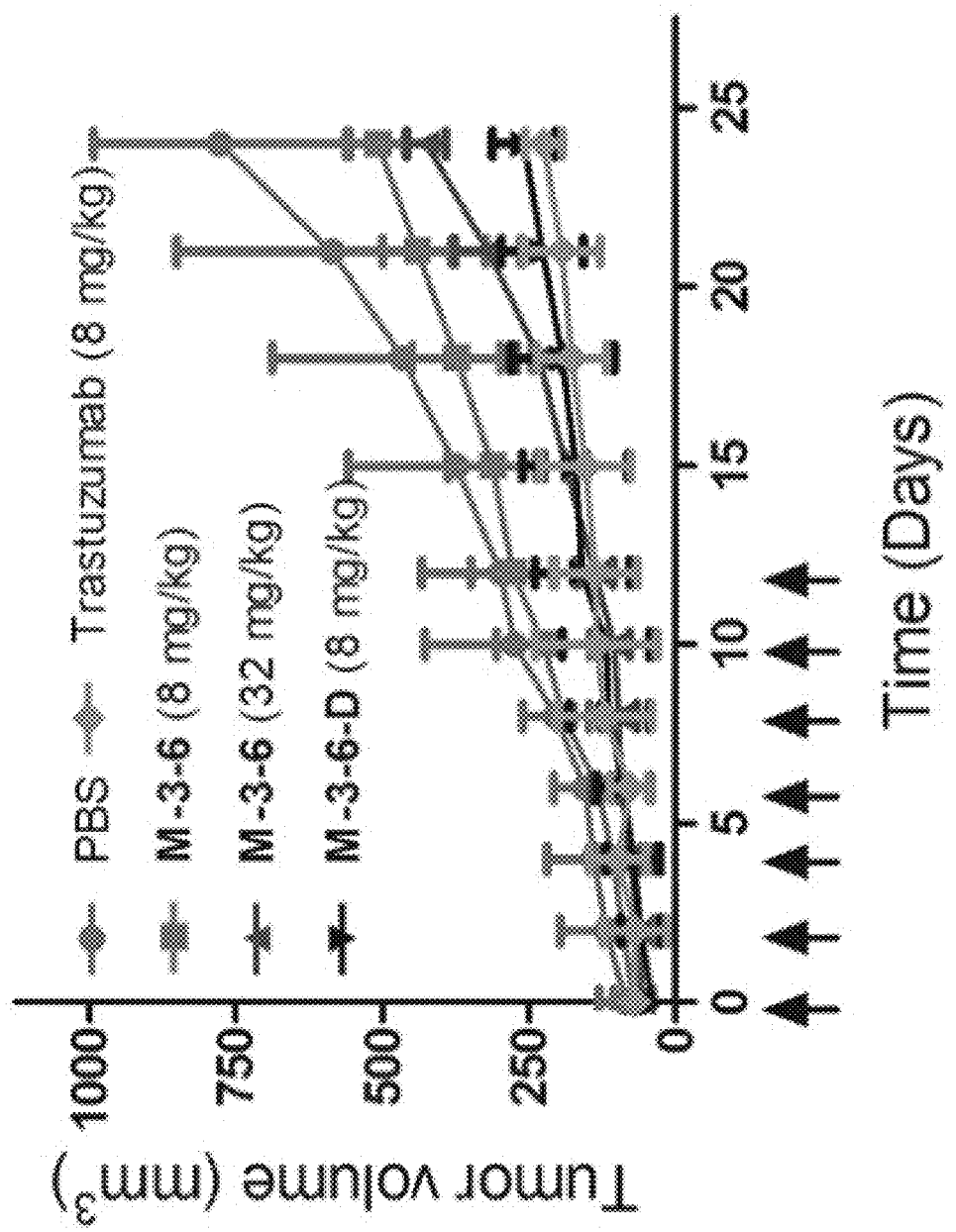
Figure 6:
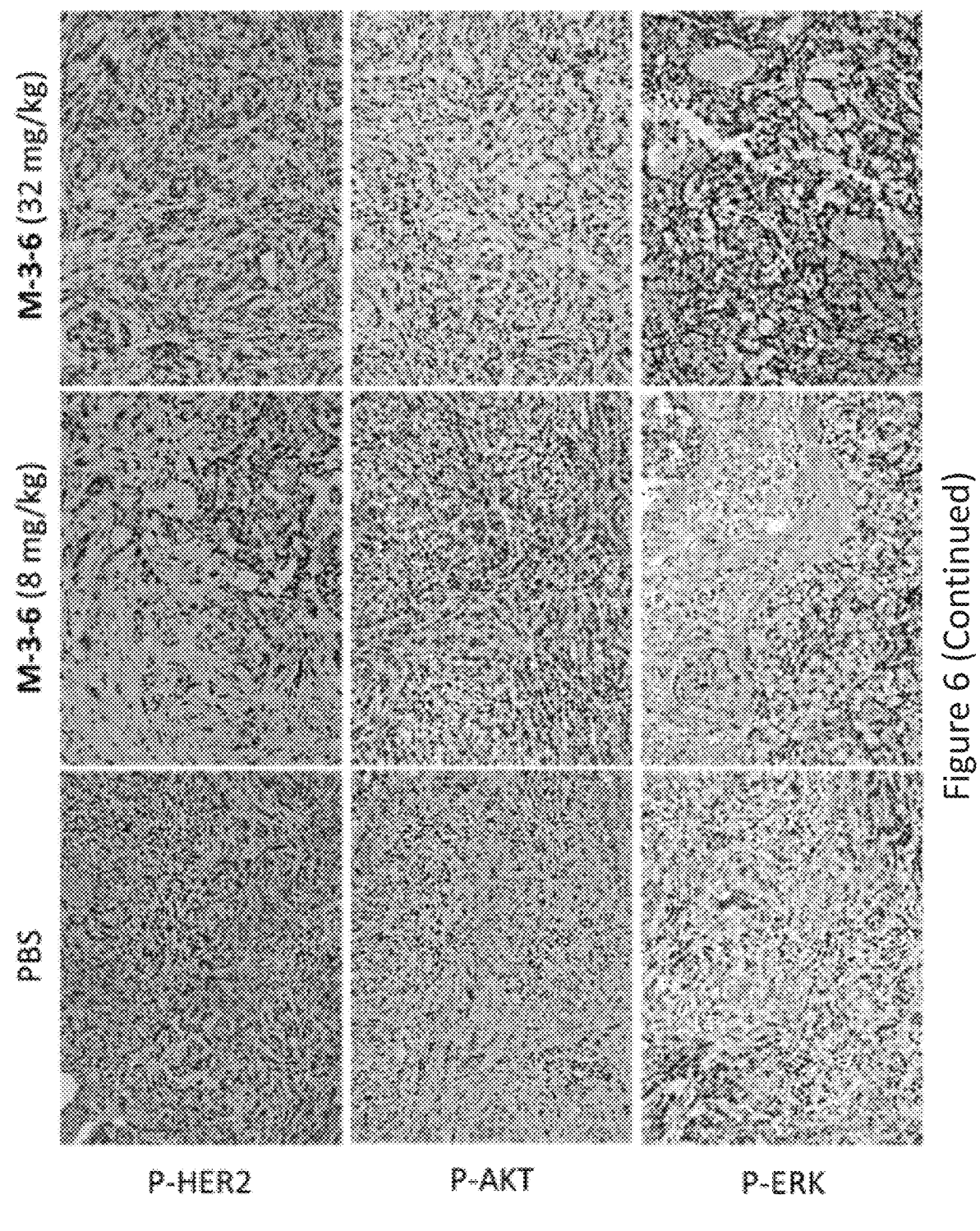
Figure 6:
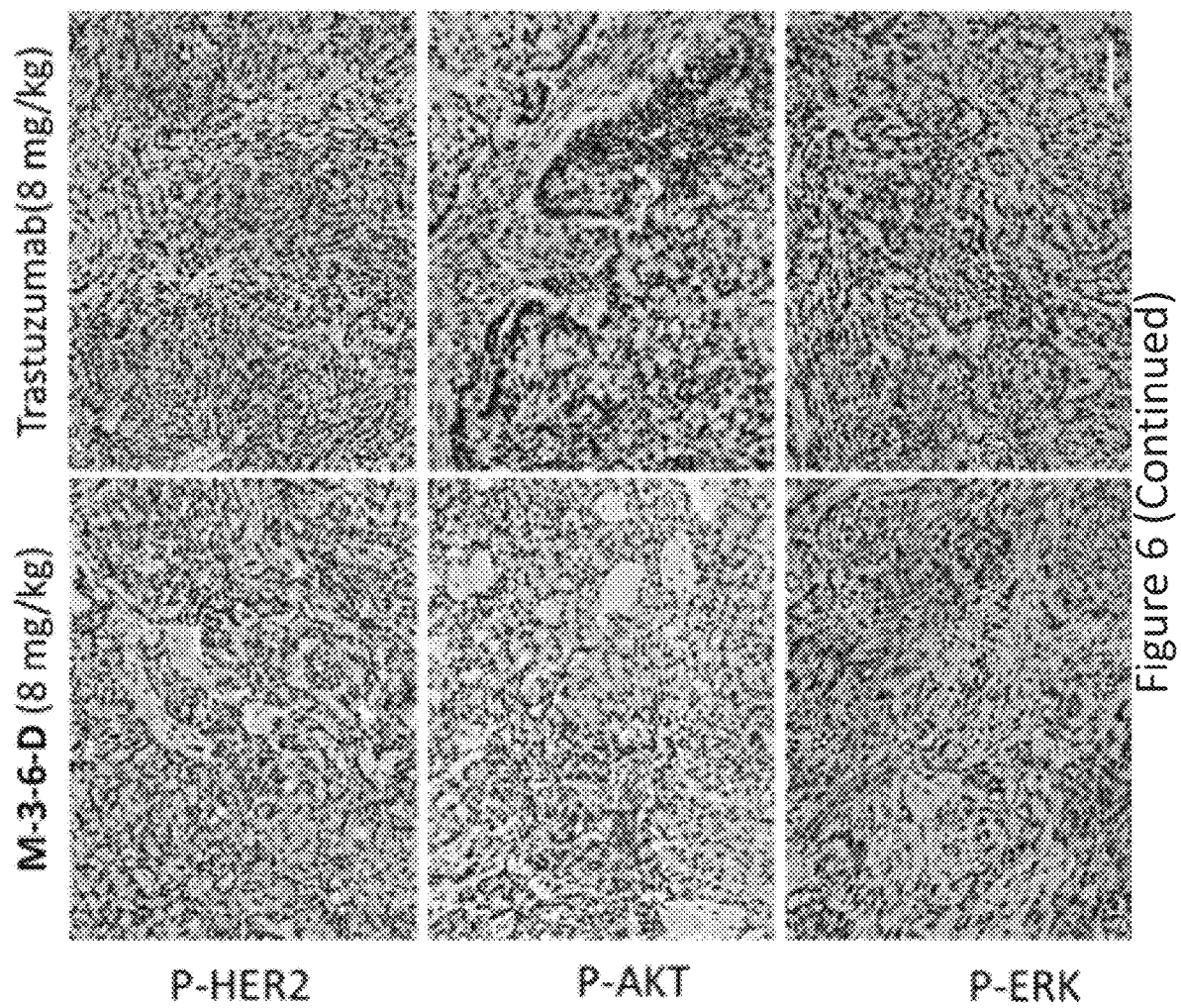

The inventors discovered that the dimeric compound of formula (iv) has dissociation constant ($K_d$) with HER2 of about 30.1 nM (FIG. 10). Thus, in some embodiments, the dimeric compounds bind to Her2 with a dissociation constant ($K_d$) of less than about 100 nm, preferably less than about 50 nM, less than about 45 nM, less than about 40 nM, or less than about 35 nM. Without being limited by any theory or mechanism, the inventors believe that the disclosed compounds bind to HER2 and prevent heterodimerization, thereby reducing the activity of HER2 (FIGS. 5B-C). Accordingly, in some embodiments, the cyclic γ-AAs prevent heterodimerization of HER2. The inventors also discovered that the disclosed compounds reduce the proliferation of tumor cells, e.g., breast cancer cells (FIG. 5D). Furthermore, the inventors demonstrated that the disclosed compound reduce the growth of tumors in a mouse model of breast cancer (FIG. 6B).

Thus, the compounds described herein can be used for treating HER2 positive cancers, as detailed more below.

Pharmaceutical Compositions

In another aspect of the current disclosure, pharmaceutical compositions are provided. In some embodiments, the pharmaceutical compositions comprise a cyclic γ-amino acid peptide (cyclic γ-AA) selected from the compounds having the formula:

formula (i)
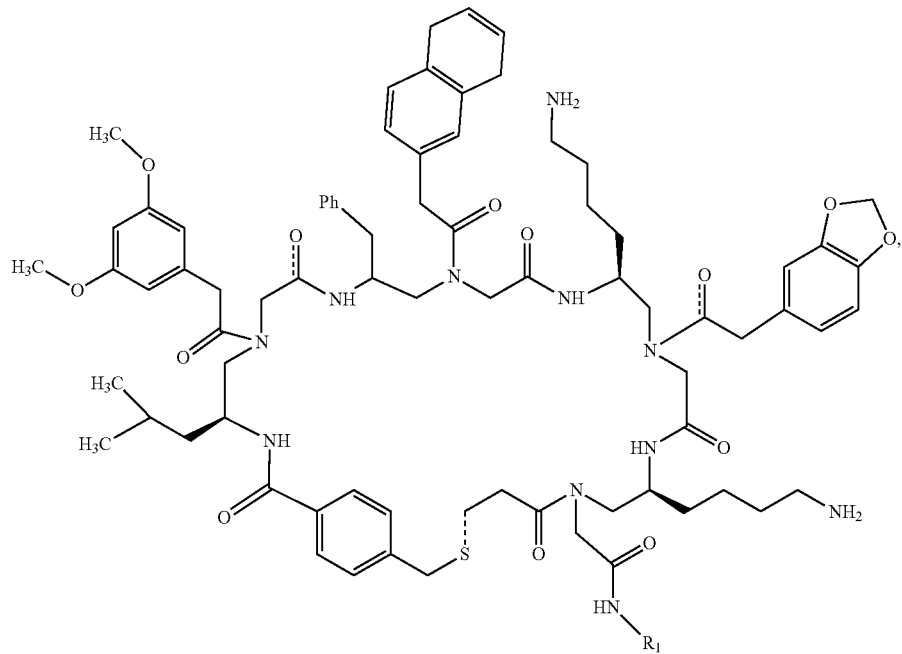
wherein R1 comprises H, a tag, a linker or a linker-tag complex, formula (iii):
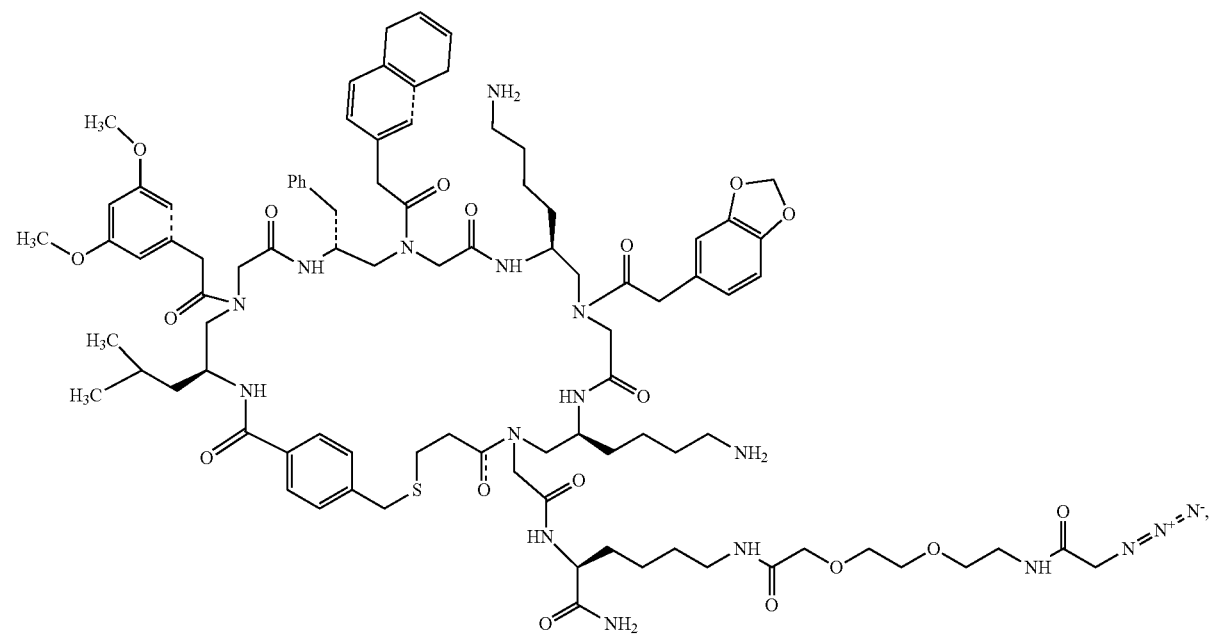

or formula (iv)

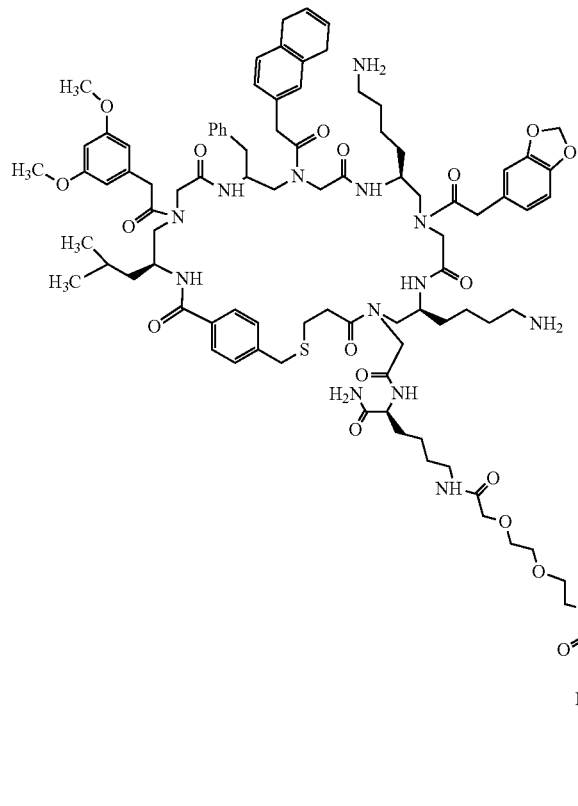 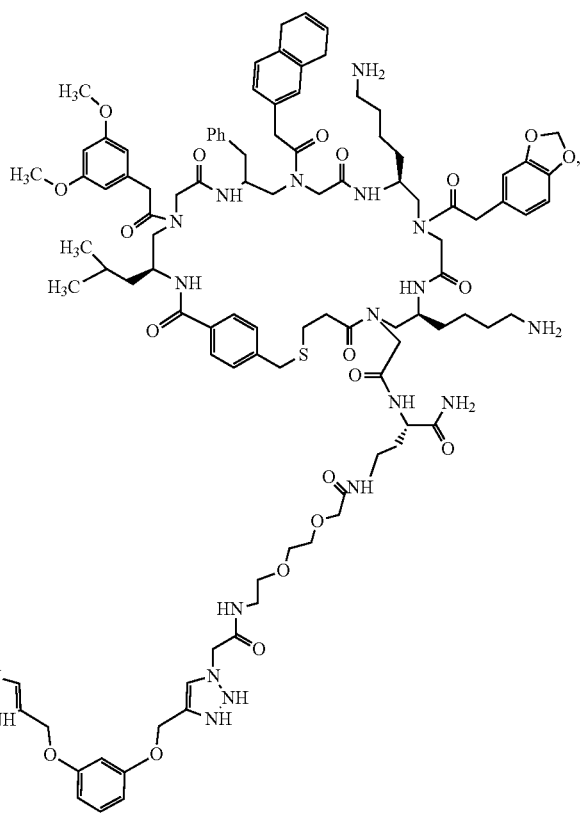

and a pharmaceutically acceptable carrier.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally, intravenously or intratumorally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The term "pharmaceutically acceptable carrier" refers to any carrier, diluent or excipient that is compatible with the other ingredients of the formulation and not deleterious to the recipient. The compounds can be administered with a pharmaceutically acceptable carrier selected on the basis of the selected route of administration and standard pharmaceutical practice for each component. The active agent may be formulated into dosage forms according to standard practices in the field of pharmaceutical preparations. See: Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, injectable solutions, troches, suppositories, or suspensions.

For oral administration, the active ingredient may be combined with at least one solid inactive ingredient for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents. or lubricating agents. Liquid and gel oral administration and formulations are also contemplated.

For parenteral administration, the active agent may be mixed with a suitable carrier or diluent such as an oil (e.g., a vegetable oil), ethanol, saline solution (e, g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension, or emulsion.

The pharmaceutical composition is preferably in unit dosage form. In such form, the preparation is divided into unit doses containing appropriate quantities of the active component.

The compounds for use according to the methods of disclosed herein may be administered as a single compound or a combination of compounds. For example, a compound that inhibits the biological activity of HER2 may be administered as a single compound or in combination with another compound inhibits the biological activity of HER2 or that has a different pharmacological activity.

The pharmaceutical compositions may be utilized in methods of treating a disease or disorder associated with the biological activity of HER2. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration. By way of example, a treated subject may be at reduced risk for cancer, or treatment may lessen the severity of a cancer or potential metastasis.

As used herein the term "effective amount" or "therapeutically effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with biological activity of HER2. By way of example but not by way of limitation, in some embodiments an effective amount is sufficient to result in one or more of reduced tumor volume, reduced tumor appearance on imaging, reduced tumor antigen in the blood or other suitable fluid, increased appetite or healthy weight gain in the subject after treatment, as compared to the subject before treatment, or compared to an appropriately matched, untreated control. Further, the result can be reducing, inhibiting or preventing the growth of cancer cells, reducing, inhibiting or preventing metastasis of the cancer cells or invasiveness of the cancer cells or metastasis, or reducing, alleviating, inhibiting or preventing at least one symptoms of the cancer or metastasis thereof, or any other desired alteration of a biological system. An "effective treatment" refers to treatment producing a beneficial effect, e.g., amelioration of at least one symptom of a cancer. A beneficial effect can take the form of an improvement over baseline, i.e., an improvement over a measurement or observation made prior to initiation of therapy according to the method. A beneficial effect can also take the form of reducing, inhibiting or preventing further growth of cancer cells, reducing, inhibiting or preventing metastasis of the cancer cells or invasiveness of the cancer cells or metastasis or reducing, alleviating, inhibiting or preventing at least one symptoms of the cancer or metastasis thereof. Such effective treatment may, e.g., reduce patient pain, reduce the size or number of cancer cells, may reduce or prevent metastasis of a cancer cell, or may slow cancer or metastatic cell growth.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition, and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Methods of Treatment

In another aspect of the current disclosure, methods of treating a cell proliferative disease or disorder in a subject in need thereof are provided. In some embodiments, the methods comprise administering a therapeutically effective amount of a cyclic γ-amino acid peptide compound (cyclic γ-AA) or composition comprising the compound to the subject to treat the cell proliferative disease or disorder. In some embodiments, the cyclic γ-amino acid peptides comprise the molecule of formula (i):

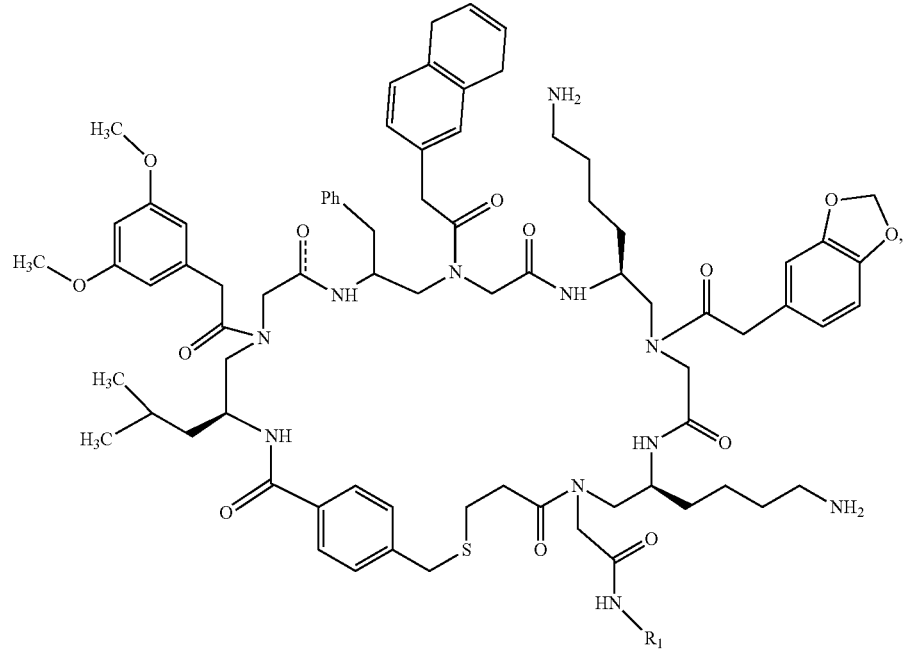

wherein R1 comprises H, a tag, a linker, a linker-tag complex, or a pharmaceutical agent. In some embodiments, R1 is a linker and is selected from an unsubstituted $C_1$-$C_{20}$ alkyl, substituted $C_1$-$C_{20}$ alkyl, $C_2$-$C_{20}$ alkenyl, phenyl, phenyl substituted $C_1$-$C_{20}$ alkyl, cycloalkyl substituted $C_1$-$C_{20}$ alkyl, an amino acid, and polyethylene glycol (PEG). In some embodiments, the cyclic γ-amino acid peptide comprises a dimeric compound comprising two cyclic γ-amino acid peptides. In some embodiments, the structure of the dimeric compound is formula (i)-linker-formula (i), wherein the first and second formula (i) compounds are linked via a linker through R1. In some embodiments, the linker between the two formula (i) compounds comprises one or more linkers and/or one or more additional molecules. In some embodiments, the dimeric compound is a compound of formula (iv):

formula (iv)

treatment includes the alleviation or prevention of symptoms, slowing or stopping the progression or worsening of a disease, disorder, or condition and/or the remission of the disease, disorder or condition. In certain embodiments, the treatment comprises anti-cancer therapy and/or treatments. The term "treatment" can be characterized by at least one of the following: (a) the reducing, slowing or inhibiting the growth of cancer and cancer cells, including slowing or inhibiting the growth of metastatic cancer cells; (b) preventing the further growth of tumors; (c) reducing or preventing the metastasis of cancer cells within a subject; (d) reducing or ameliorating at least one symptom of cancer. In some

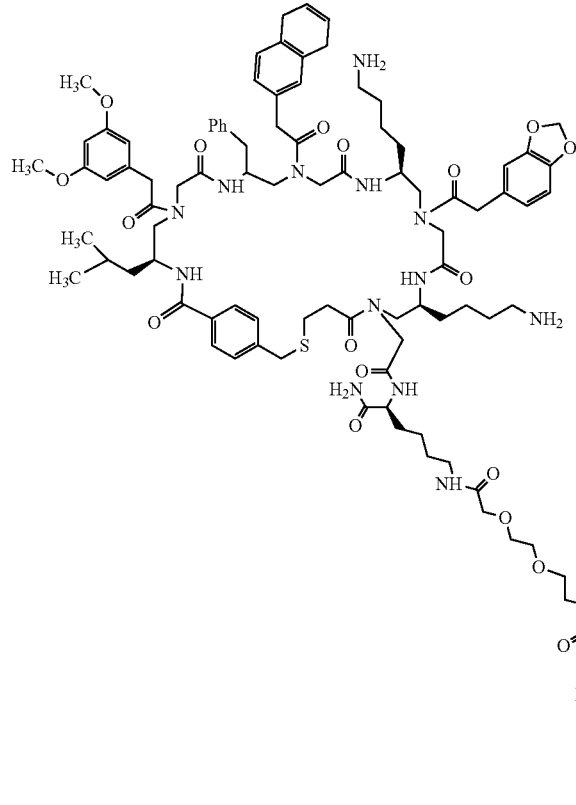
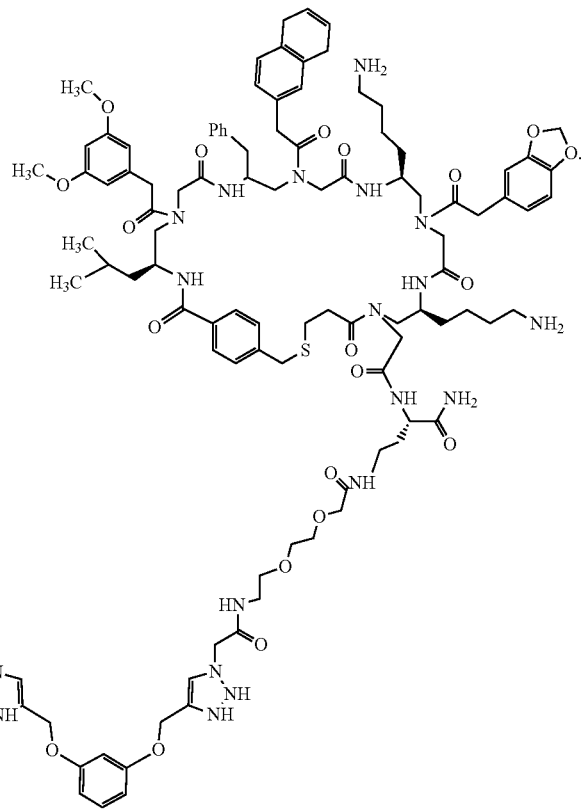

In some embodiments, the cyclic γ-amino acid peptide compound further comprises a pharmaceutically acceptable carrier. In some embodiments, the cell proliferative disease or disorder is cancer. In some embodiments, the cancer is characterized by expression of Her2. In some embodiments, the cancer is selected from breast cancer, gastric cancer, and gastroesophageal cancer. In some embodiments, the method reduces the growth of the tumor in the subject. In some embodiments, the method reduces phosphorylation of Her2, Erk, or Akt in the subject. In some embodiments, the method reduces proliferation of tumor cells in the subject. In some embodiments, the method reduces the volume of a tumor in the subject.

For purposes of the present invention, "treating" or "treatment" describes the management and care of a subject for the purpose of combating the disease, condition, or disorder. Treating includes the administration of a compositions of present invention to prevent the onset of the symptoms or complications, alleviating the symptoms or complications, or eliminating the disease, condition, or disorder. The aim of embodiments, the optimum effective amount can be readily determined by one skilled in the art using routine experimentation.

In some embodiments, the method further comprises administering a therapeutically effective amount of an additional chemotherapeutic or immunotherapeutic agent to the subject. Exemplary chemotherapeutic drugs comprise: taxanes, e.g., paclitaxel, docetaxel, and albumin-bound paclitaxel, ixabepilone, eribulin, anthracyclines, e.g., doxorubicin, liposomal doxorubicin, and epirubicin, platinum-based agents, e.g., cisplatin and carboplatin, vinorelbine, capecitabine, gemcitabine, antibody drug conjugates, e.g., ado-trastuzumab emtansine, fam-trastuzumab deruxtecan, sacituzumab govitecan. Exemplary immunotherapies comprise: Margetuximab-cmkb: a monoclonal antibody that targets the HER2 pathway; approved in combination with chemotherapy for subsets of patients with advanced breast cancer. Pertuzumab: a monoclonal antibody that targets the HER2 pathway; approved for subsets of patients with HER2-positive breast cancer. Sacituzumab govitecan: an antibody-drug conjugate that targets the TROP-2 pathway; approved for subsets of patients with triple-negative breast cancer (TNBC). Trastuzumab: a monoclonal antibody that targets the HER2 pathway; approved for subsets of patients with HER2-positive breast cancer. Trastuzumab deruxtecan: an antibody-drug conjugate that targets the HER2 pathway and delivers toxic drugs to tumors; approved for subsets of patients with advanced, HER2-positive breast cancer. Trastuzumab emtansine: an antibody-drug conjugate that targets the HER2 pathway and delivers toxic drugs to tumors; approved for subsets of patients with HER2-positive breast cancer. Dostarlimab: a checkpoint inhibitor that targets the PD-1/PD-L1 pathway; approved for subsets of patients with advanced breast cancer that has DNA mismatch repair deficiency (dMMR). Pembrolizumab: a checkpoint inhibitor that targets the PD-1/PD-L1 pathway; approved in combination with chemotherapy for patients with metastatic, PD-L1-positive triple-negative breast cancer (TNBC), including for treatment prior to and after surgery; also approved for subsets of patients with advanced breast cancer that has high microsatellite instability (MSI-H), DNA mismatch repair deficiency (dMMR), or high tumor mutational burden (TMB-H).

In some embodiments, the compounds described herein can be linked to an additional therapeutic agent, for example, an additional anti-cancer agent.

Methods of Detecting HER2

In another aspect of the current disclosure, methods of detecting HER2 in a sample from a subject suffering from a cancer suspected of expressing HER2 are provided. In some embodiments, the methods comprise: i) contacting the sample with a cyclic γ-amino acid compound comprising the molecule of formula (i):

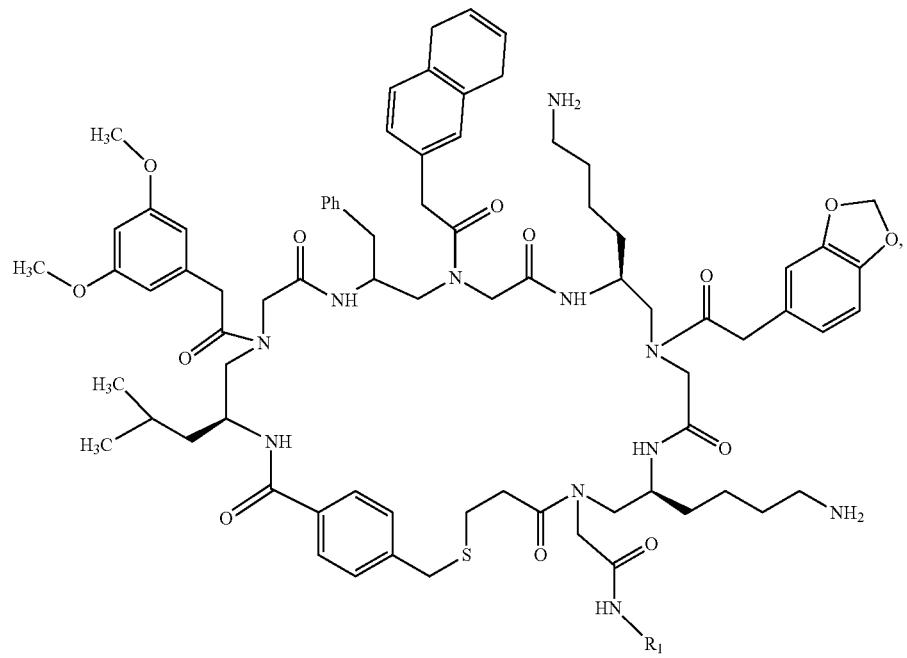

wherein R1 comprises H, a tag, a linker, or a linker-tag complex to generate cyclic γ-amino acid-Her2 complex (complex), and ii) detecting the presence of the complex wherein the presence of the complex indicates the presence of Her2 in a sample from the subject. In some embodiments, the methods further comprise iii) administering a therapeutically effective amount of an anti-Her2 therapy. In some embodiments, the anti-Her2 therapy comprises a pharmaceutical composition comprising a cyclic γ-amino acid peptide selected from the compounds having the structure of formula (i):

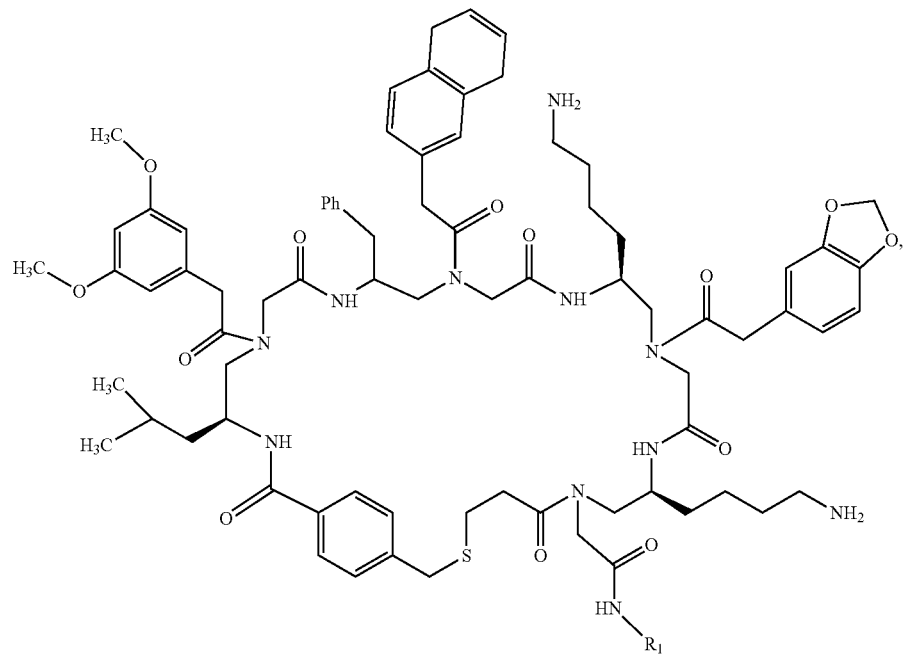

wherein R1 comprises H, a tag, a linker or a linker-tag complex, formula (iii):

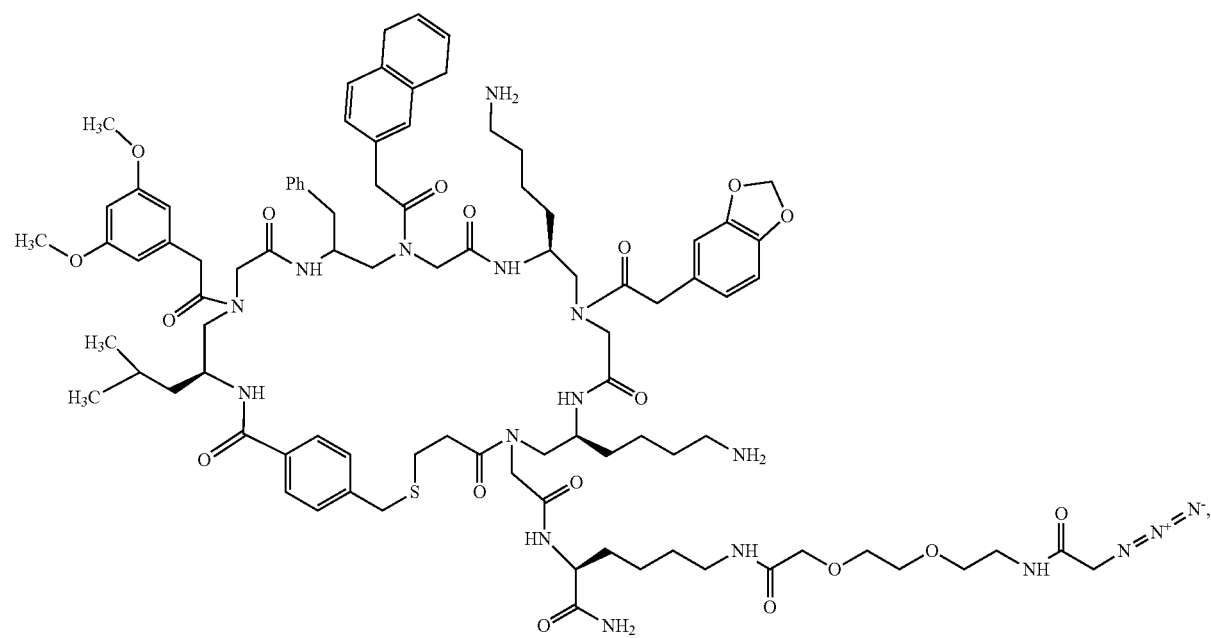

or formula (iv):

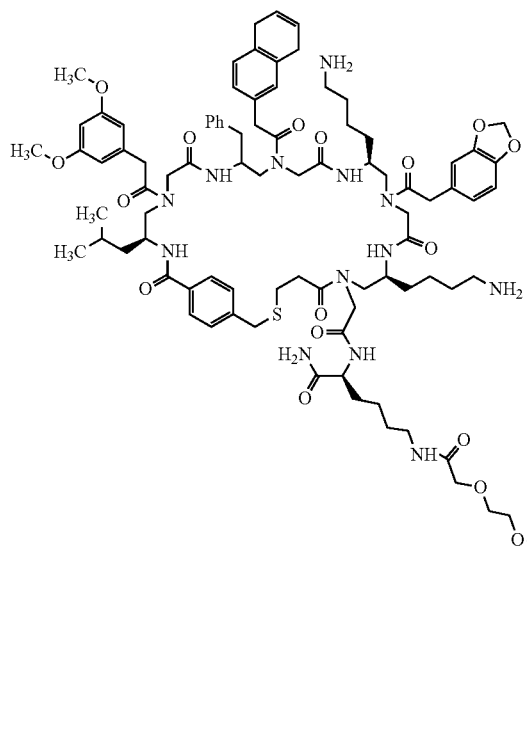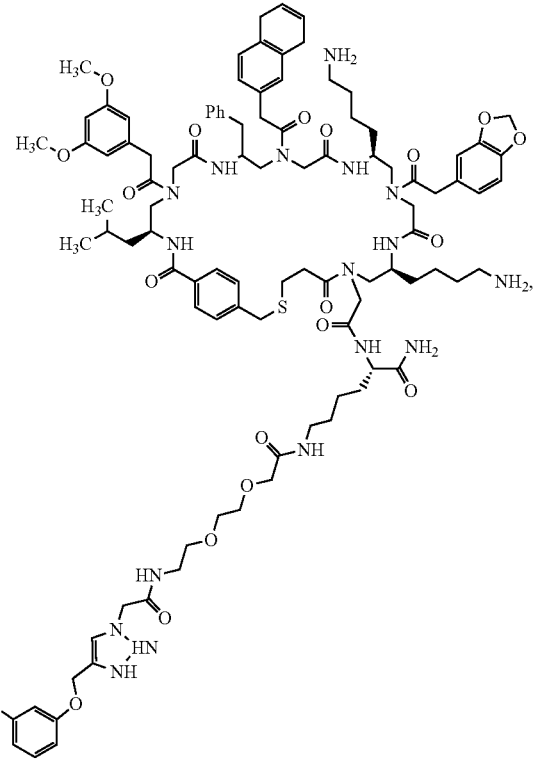

and a pharmaceutically acceptable carrier.

In another aspect of the current disclosure, methods of detecting HER2 in a sample are provided. In some embodiments, the methods of detecting HER2 in a sample from a subject comprise i) contacting the sample with a cyclic γ-amino acid compound with the structure of formula (i):

wherein R1 comprises H, a tag, a linker, or a linker-tag complex, to generate cyclic γ-amino acid-Her2 complex (complex), and ii) detecting the presence of the complex wherein the presence of the complex indicates the presence of Her2 in a sample from the subject. In some embodiments, the methods further comprise iii) wherein HER2 is present

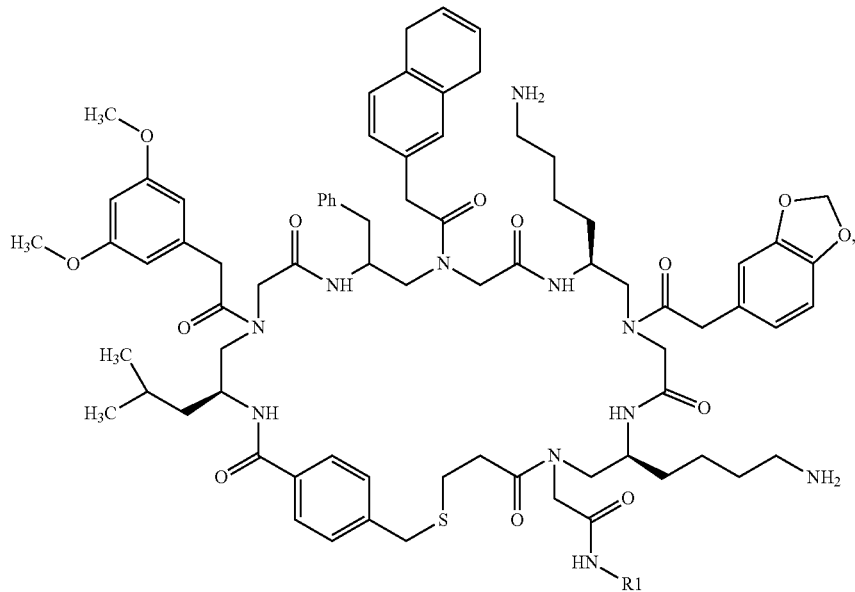

in the sample, administering a therapeutically effective amount of an anti-Her2 therapy to the subject and wherein HER2 is not present in the sample, administering a therapeutically effective amount of an additional chemotherapeutic or immunotherapeutic agent to the subject. In some embodiments, the anti-Her2 therapy comprises a pharmaceutical composition comprising a cyclic γ-amino acid peptide selected from the compounds having the structure of formula (i):

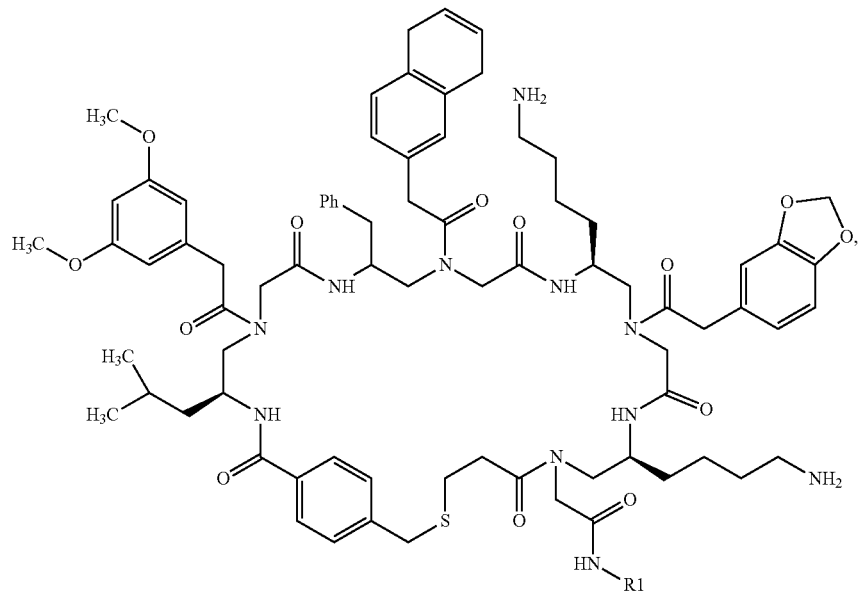

wherein R1 comprises H, a tag, a linker, or a linker-tag complex,
formula (iii)

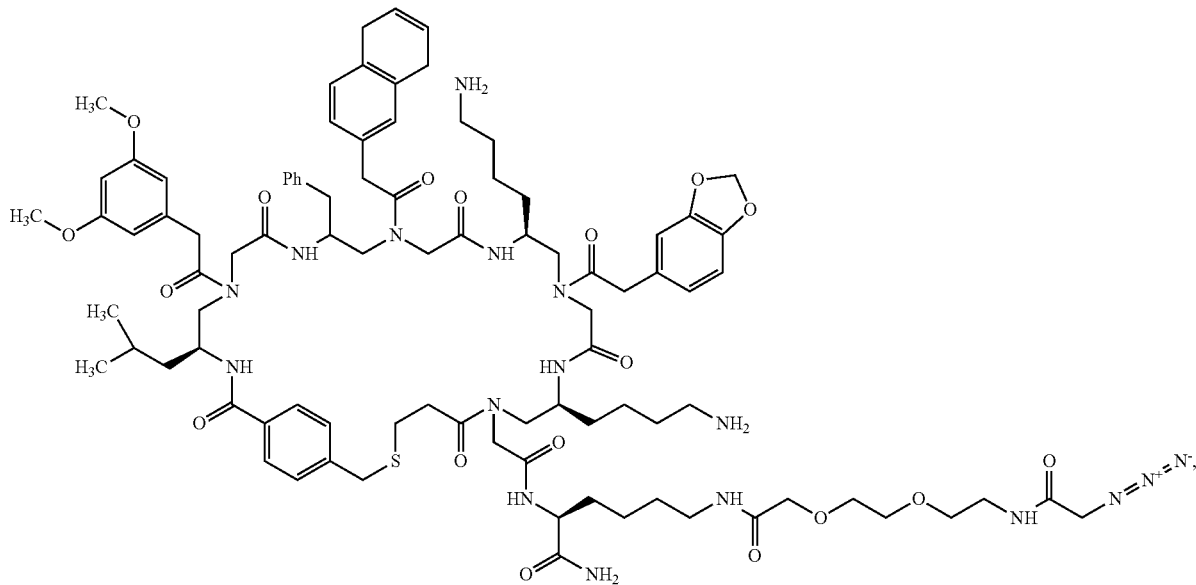

or formula (iv)

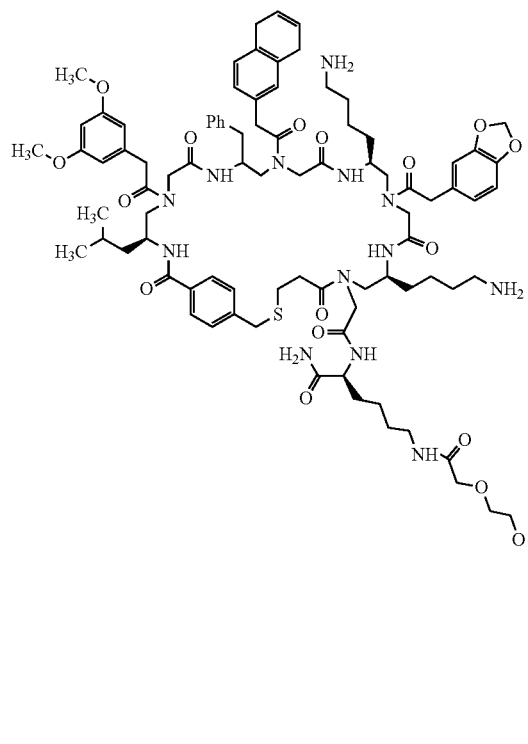 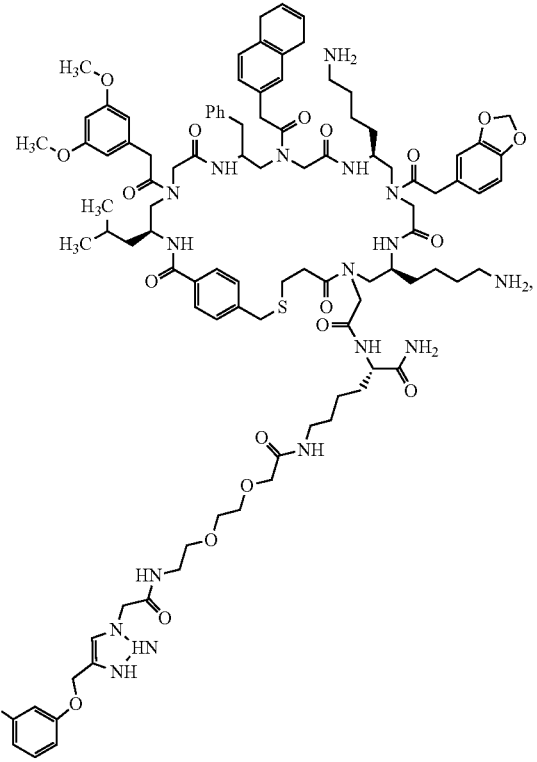

pharmaceutically acceptable carrier.

Kits

In another aspect of the current disclosure, kits are provided. In some embodiments, the kits comprise: i) a cyclic γ-amino acid peptide compound comprising a compound with the structure of formula (i):

wherein R1 is H, a tag, a linker, or a linker-tag complex, and ii) a detection reagent. In some embodiments, the kits further comprise iii) a solid support.

As used herein, "solid support" refers to any substrate having a surface to which molecules can be attached, directly or indirectly, through either covalent or non-cova-

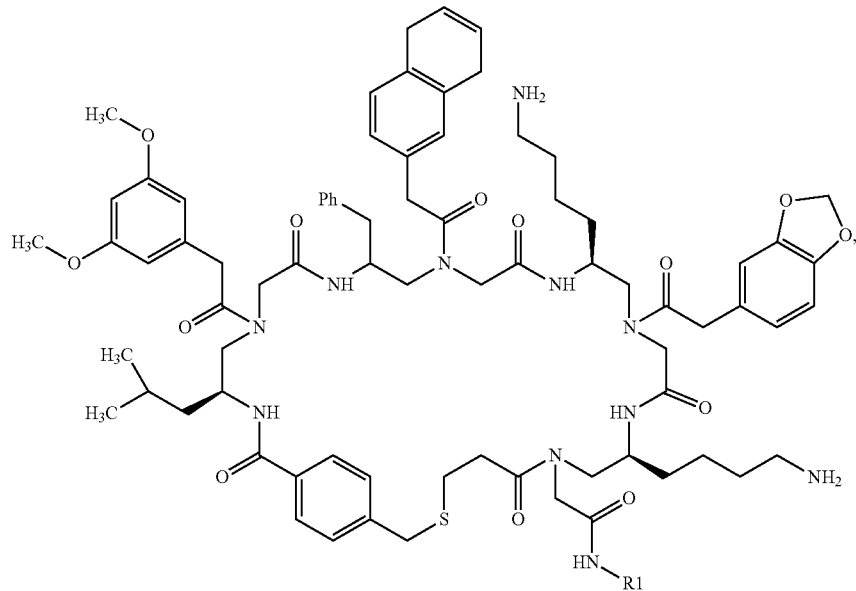

lent bonds. The substrate materials can be naturally occurring, synthetic, or a modification of a naturally occurring material. Solid support materials include filters, paper, silicon, graphite, mirrored surfaces, laminates, ceramics, plastics (including polymers such as, e.g., poly(vinyl chloride), cyclo-olefin copolymers, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), germanium, gallium arsenide, gold, silver, etc., either used by themselves or in conjunction with other materials. Additional rigid materials can be considered, such as glass, which includes silica and further includes, for example, glass that is available as Bioglass. Other materials that can be employed include porous materials, such as, for example, controlled pore glass beads, filters, nitrocellulose, membranes, etc. Any other materials known in the art that are capable of having one or more functional groups, such as any of an amino, carboxyl, thiol, or hydroxyl functional group, for example, incorporated on its surface, are also contemplated.

The solid support can take any of a variety of configurations ranging from simple to complex and can have any one of a number of shapes, including a strip, plate, disk, rod, particle, including bead, tube, well, and the like. The surface can be relatively planar (e.g., a slide), spherical (e.g., a bead), cylindrical (e.g., a column), or grooved. Exemplary solid supports include microtiter wells, microscope slides, membranes, paramagnetic beads, charged paper, Langmuir-Blodgett films, silicon wafer chips, flow through chips, and microbeads.

In some embodiments, the solid support comprises a microplate, a lateral flow device, or a microfluidic device.

In some embodiments, the cyclic γ-amino acid compound comprises a compound with the structure of formula (ii):

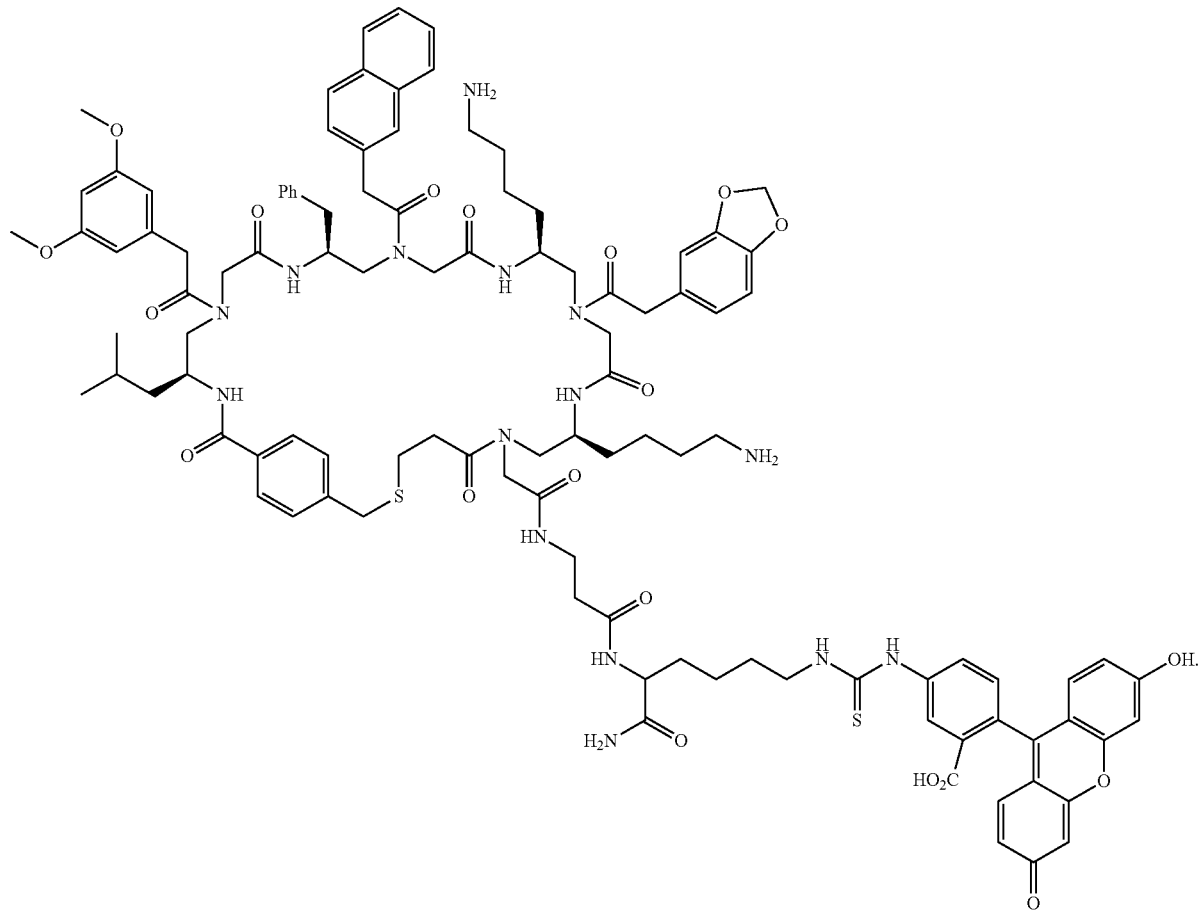 [SMILES: COc1cc(CC(=O)N2CC(=O)N[C@@H](Cc3ccccc3)CN(C(=O)Cc3ccc4ccccc4c3)CC(=O)N[C@@H](CCCCN)CN(C(=O)Cc3ccc4c(c3)OCO4)CC(=O)N[C@@H](CCCCN)CN(CC(=O)NCCC(=O)NC(CCCCNC(=S)Nc3ccc(-c4c5ccc(=O)cc-5oc5cc(O)ccc45)c(C(=O)O)c3)C(N)=O)C(=O)CCSCc3ccc(cc3)C(=O)N[C@@H](CC(C)C)C2)cc(OC)c1]

In some embodiments, the detection reagent comprises a secondary antibody specific for the cyclic γ-amino acid compound.

In a further embodiment, the present disclosure provides a method of reducing or inhibiting cancer cell growth in a subject having cancer, the method comprising administering an effective amount of the compounds or compositions described herein. The administering may be intravenous, intratumorally or oral. In one or more embodiments, the method further comprises detecting HER2 positive cancer in the subject after treatment, and/or monitoring tumor size after treatment.

Definitions

The disclosed subject matter may be further described using definitions and terminology as follows. The definitions and terminology used herein are for the purpose of describing particular embodiments only and are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover, the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

A "subject in need thereof" as utilized herein may refer to a subject in need of treatment for a disease or disorder associated with HER2 activity and/or expression. A subject in need thereof may include a subject suffering from, for example, a cell proliferative diseases or disorder, e.g., cancer. In some embodiments, a subject in need thereof is suffering from breast cancer, gastric, or gastroesophageal cancer. In some embodiments, the breast, gastric, or gastroesophageal cancers are characterized by increased expression of HER2.

The term "subject" may be used interchangeably with the terms "individual" and "patient" and includes human and non-human mammalian subjects.

The disclosed compounds, pharmaceutical compositions, and methods may be utilized to treat diseases and disorders associated with HER2 activity and/or expression which may include, but are not limited to cell proliferative diseases or disorders, e.g., cancer. In some embodiments, the disclosed compounds, pharmaceutical compositions, and methods may be utilized to reduce the volume or progression of a tumor, in a subject diagnosed with or suffering from a cell proliferative disease or disorder, e.g., cancer.

The disclosed compounds may be utilized to modulate the biological activity of HER2. The term "modulate" should be interpreted broadly to include "inhibiting" HER2 biological activity, including the heterodimerization of HER2 and/or the receptor tyrosine kinase activity of HER2.

The phrases "% sequence identity," "percent identity," or "% identity" refer to the percentage of amino acid residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain.

Nucleic acids, proteins, and/or other compositions described herein may be purified. As used herein, "purified" means separate from the majority of other compounds or entities, and encompasses partially purified or substantially purified. Purity may be denoted by a weight by weight measure and may be determined using a variety of analytical techniques such as but not limited to mass spectrometry, HPLC, etc.

Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

The terms "nucleic acid" and "nucleic acid molecule," as used herein, refer to a compound comprising a nucleobase and an acidic moiety, e.g., a nucleoside, a nucleotide, or a polymer of nucleotides. Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides, (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Chemical Entities

Chemical entities and the use thereof may be disclosed herein and may be described using terms known in the art and defined herein.

The term "alkyl" as used herein refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$-alkyl, and $C_1$-$C_6$-alkyl, respectively.

The term "alkylene" refers to a diradical of an alkyl group. An exemplary alkylene group is —$CH_2CH_2$—.

The term "haloalkyl" refers to an alkyl group that is substituted with at least one halogen, for example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxyl" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$-alkenyl, $C_2$-$C_{10}$-alkenyl, and $C_2$-$C_6$-alkenyl, respectively. A "cycloalkene" is a compound having a ring structure (e.g., of 3 or more carbon atoms) and comprising at least one double bond.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as $C_2$-$C_{12}$-alkynyl, $C_2$-$C_{10}$-alkynyl, and $C_2$-$C_6$-alkynyl, respectively.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "carboxy" or "carboxyl" as used herein refers to the radical —COOH or its corresponding salts, e.g. —COONa, etc.

The term "amide" or "amido" or "carboxamido" as used herein refers to a radical of the form —$R^1C(O)N(R^2)$—, —$R^1C(O)N(R^2)$ $R^3$—, —$C(O)NR^2R^3$, or —$C(O)NH_2$, wherein $R^1$, $R^2$ and $R^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

Aspects of the present disclosure that are described with respect to methods can be utilized in the context of the pharmaceutical compositions or kits discussed in this disclosure. Similarly, aspects of the present disclosure that are described with respect to the pharmaceutical compositions can be utilized in the context of the methods and kits, and aspects of the present disclosure that are described with respect to kits can be utilized in the context of the methods and compositions.

Suitable kits include kits for inhibiting or reducing cancer cell number or cancel tumor volume. The kit comprises at least one compound or composition as described herein. In another embodiment, the kit comprises a compound or composition for detecting HER2 positive cancers. The kit comprises one or more compounds of the present invention linked to a tag or detection agent.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim.

The following non-limiting examples are included for purposes of illustration only, and are not intended to limit the scope of the range of techniques and protocols in which the compositions and methods of the present invention may find utility, as will be appreciated by one of skill in the art and can be readily implemented.

EXAMPLES

The following Examples are illustrative and should not be interpreted to limit the scope of the claimed subject matter.

Example 1—Peptidomimetic-Based Antibody Surrogate for HER2

Significant efforts have been extended to develop HER2-targeting drugs for treating HER2-positive breast cancer, including monoclonal antibodies (mAbs) trastuzumab[6] and pertuzumab[7] that bind to the extracellular domain of HER2 and small molecules tyrosine kinase inhibitors lapatinib[8] and neratinib[9] targeting intracellular kinase site. While these agents have significantly improved patient outcomes, there are still drawbacks associated with the treatment. For instance, the ultimate development of drugs resistance is common that presents a major challenge to the treatment of breast cancer in clinical therapy, particularly due to the use of tyrosine kinase inhibitors[10]. As to monoclonal antibodies, although they are highly specific, their high cost of production, large molecular weight, and susceptibility to enzymatic degradation, could be a hurdle for therapeutic development and long-term usage. In addition, recently clinical studies have suggested that the combinational treatment of HER2 inhibitors that inhibit HER2 by different mechanism is more effective than a single HER2 inhibitor. For example, the addition of tyrosine kinase inhibitors lapatinib showed improved activity in patients with monoclonal antibody trastuzumab treatment[11]. Treatment with monoclonal antibody trastuzumab and monoclonal antibody pertuzumab resulted in greater antitumor activity since trastuzumab binds to subdomain IV of the HER2 extracellular domain and pertuzumab binds HER2 at a different epitope of the HER2 extracellular domain (subdomain 11)[12]. Furthermore, the triple combination of pertuzumab, trastuzumab and docetaxel significantly prolonged progression-free survival[13,14]. As such, there is continuing interest in the development of novel efficient HER2 targeting inhibitors which could either overcome the drawbacks of current therapeutic treatment or provide more combinational option needed on the success of HER2-targeted therapy.

Figure 2:
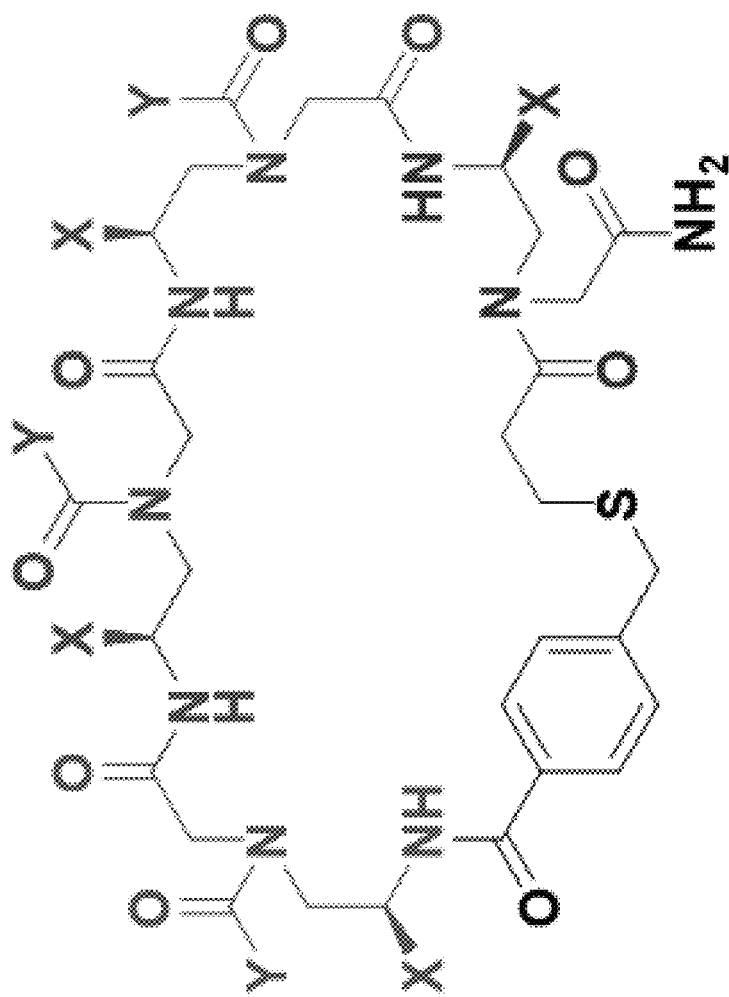
FIG. 2. (A) Structure of the cyclic-γ-AApeptides and (B) Artificial antibody based on cyclic-γ-AApeptides.
Figure 2:
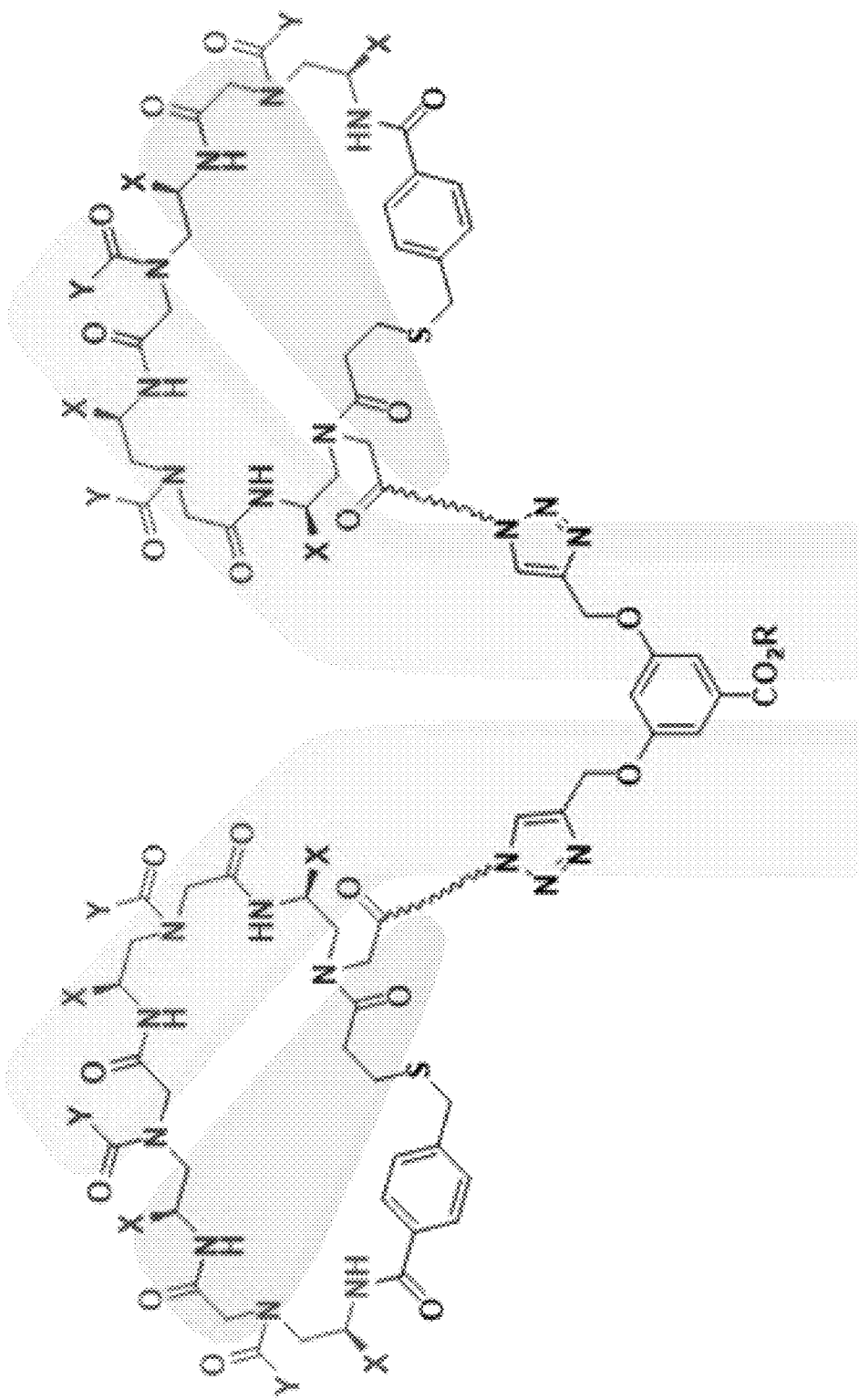

Inspired by chiral PNA backbone, we recently developed a new class of peptidomimetics, γ-AApeptides[15,16] (FIG. 1), which could fold into well-defined protein-like helical structures stabilized by intramolecular hydrogen bond[17-20], providing a novel strategy to rationally design helical mimetics of important protein domain for protein surface recognition as well as disrupt critical protein-protein interactions[21]. Meanwhile, the unique γ-AApeptides backbone also provides a novel platform with remarkable stability and diversity that has been used to develop combinatorial libraries, from which unnatural ligands could be identified to bind to proteins or nucleic acids with high specificity and affinity[22-24]. In the current study, we report a strategy to develop new generation of artificial antibody based on γ-AApeptides. Dimerization strategy has been widely used to enhance the binding affinity of ligands toward protein targets, so as to develop unnatural antibody surrogate[25-29]. It is known that antibody contains two identical binding domains on the arms of the "Y" shape (FIG. 2B), each of which is a pseudo-loop formed by the heavy chain and the light chain. The divalent mode of antibody significantly enhances it binding affinity toward target molecules. We therefore proposed to identify cyclic γ-AApeptides that could target HER2 extracellular domain (ECD), and such molecules could mimic one binding loop of antibody. After such cyclic γ-AApeptides are linked by a bidentate linker, the newly obtained dimeric cyclic γ-AApeptides could theoretically mimic the function of antibody (FIG. 2B). As the molecular weight is much smaller than antibody, and γ-AApeptides are resistant to proteolysis, we could obtain novel peptidomimetic-based artificial antibody targeting HER2. To this end, to identify a new HER2 inhibitor, we developed a one-bead-two-compounds (OBTC) combinatorial library based on cyclic γ-AApeptides, and from which we identified a γ-AApeptide M-3-6 that exhibited high selectivity and excellent binding affinity to HER2. Subsequently, we designed an antibody-like dimer of M-3-6, M-3-6-D, which exhibited remarkable binding affinity to HER2 ECD. Intriguingly, both M-3-6 and M-3-6-D could effectively inhibit cell proliferation, coincided with downregulation of phosphorylation on HER2 and their downstream signaling pathways including AKT and ERK. As anticipated, M-3-6-D showed a much better biological activity than M-3-6. Additionally, xenograft studies with SKBR3 breast cancer cells in mice demonstrated that M-3-6-D could significantly inhibit the tumor growth, with efficiency virtually identical to the marketed monoclonal drug trastuzumab.

Results and Discussion

Library synthesis and Screening

Figure 3:
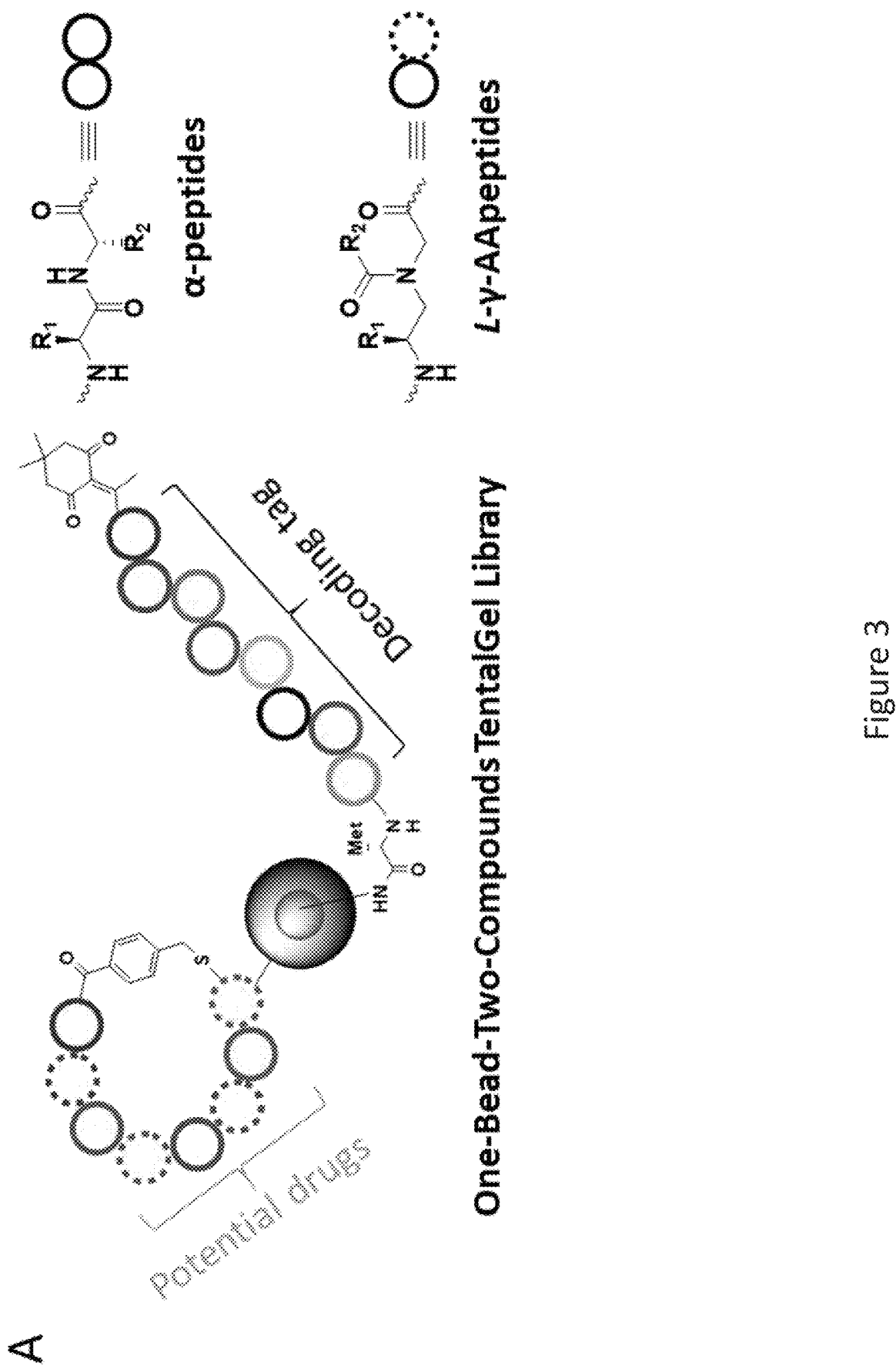
FIG. 3. (A) Schematic presentation of One-Bead-Two-Compounds TentalGel beads for library. (B) Scheme for the synthesis of OBTC cyclic γ-AApeptides library. (a) Soak in water for overnight; (b) (Boc)$_2$O, DCM/ether; (c) Fmoc-Met-OH, HOBt, DIC, DMF; (d) Deprotect Fmoc by 20% piperidine in DMF; (e) split into 5 portions equally; (f) Dde protected amino acids, PyBOP, NEM, DMF; (g) Deprotect Boc by TFA/triisopropylsilane/H$_2$O/Thioanisole (94:2:2:2); (h) Fmoc protected γ-AApeptides, HOBt, DIC, DMF; (i) Deprotecting alloc by Pd(PPh3)$_4$ and Me$_2$NH.BH$_3$ in DCM; (j) Dmt protected mercaptopropionic acid, HOBt, DIC, DMF; (k) Deprotecting Dde by NH$_2$OH.HCl and imidazole in NMP/DCM (5:1); (l) split-and-pool synthesis, repeating the previous steps; (m) Deprotecting Fmoc by 20% piperidine in DMF; (n) 4-(bromomethyl)benzoyl chloride, DIPEA, DCM; (o) Deprotecting Dmt by TFA/triisopropylsilane/DCM (2:2:96); (p) (NH$_4$)$_2$CO$_3$, DMF/H$_2$O (1:1). Xs are regular α-amino acids. (C). Scheme showing the overall strategy involved in library screening against HER2.
Figure 3:
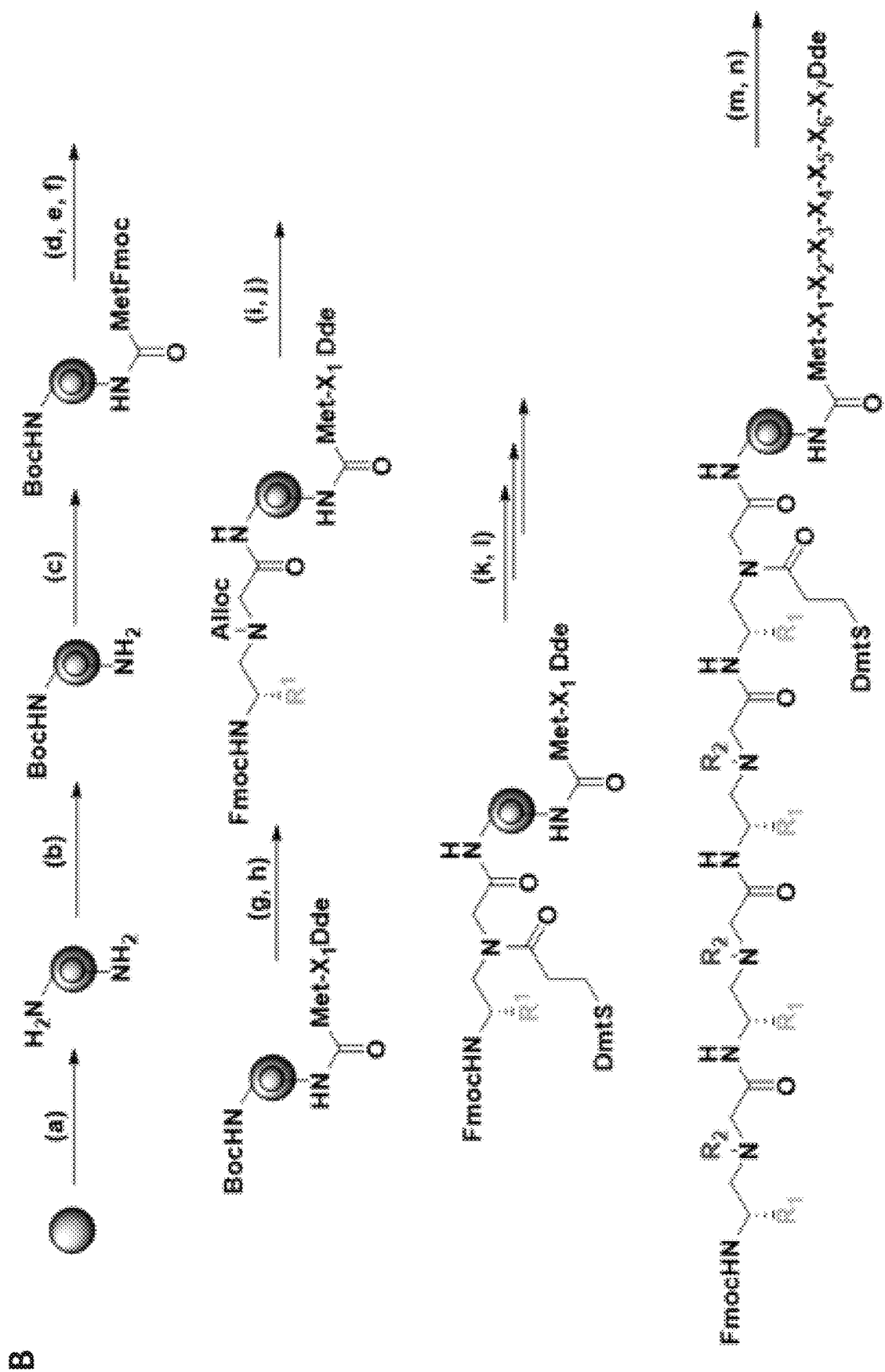
Figure 3:
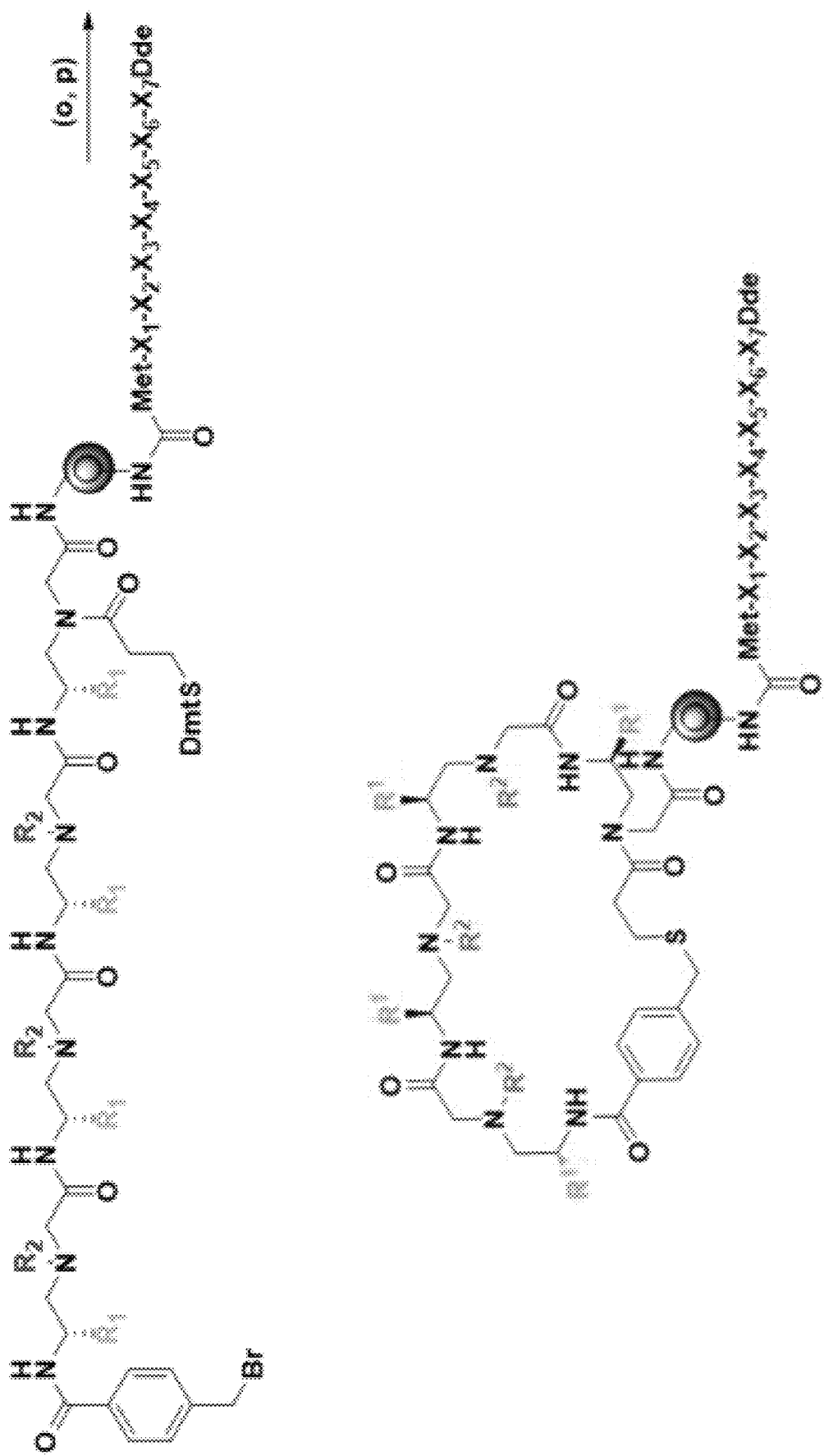
Figure 3:
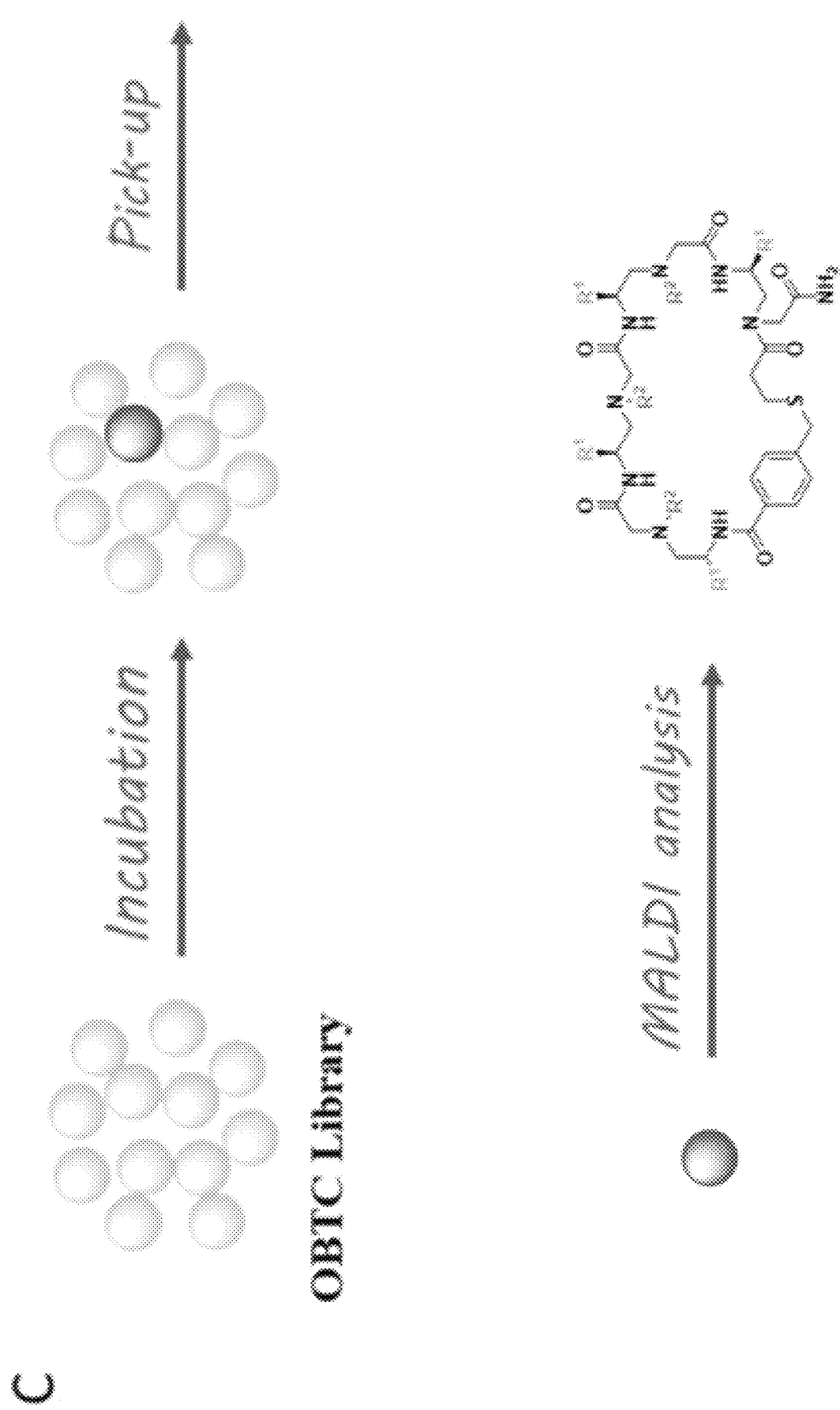

The OBTC combinatorial library was synthesized as reported previously[22] using peptide couplings and the sulfur-mediated SN2 reaction employed to construct thioether bridge for the cyclic γ-AApeptides. Briefly, each TentaGel bead was spatially segregated in two layers, which incorporate a cyclic γ-AApeptides on the surface layer and a linear α-peptides tag on the inner layer (FIG. 3A). The 320,000-member library which were displayed in triple that featured diversity at two positions in both side chains of every γ-AApeptide building block: the chiral side chains ($R_1$ in FIG. 3A) and the achiral side chains ($R_2$ in FIG. 3A) introduced by acylating the secondary amino group on the backbone. In addition, the linear decoding tag consisted of seven α-amino acid residues which were uniquely related to each side chain of the γ-AApeptides and were used for encoding the structure of the cyclic γ-AApeptides. The synthetic route is shown in FIG. 3B and details for library synthesis are provided in the supporting information.

Figure 7:
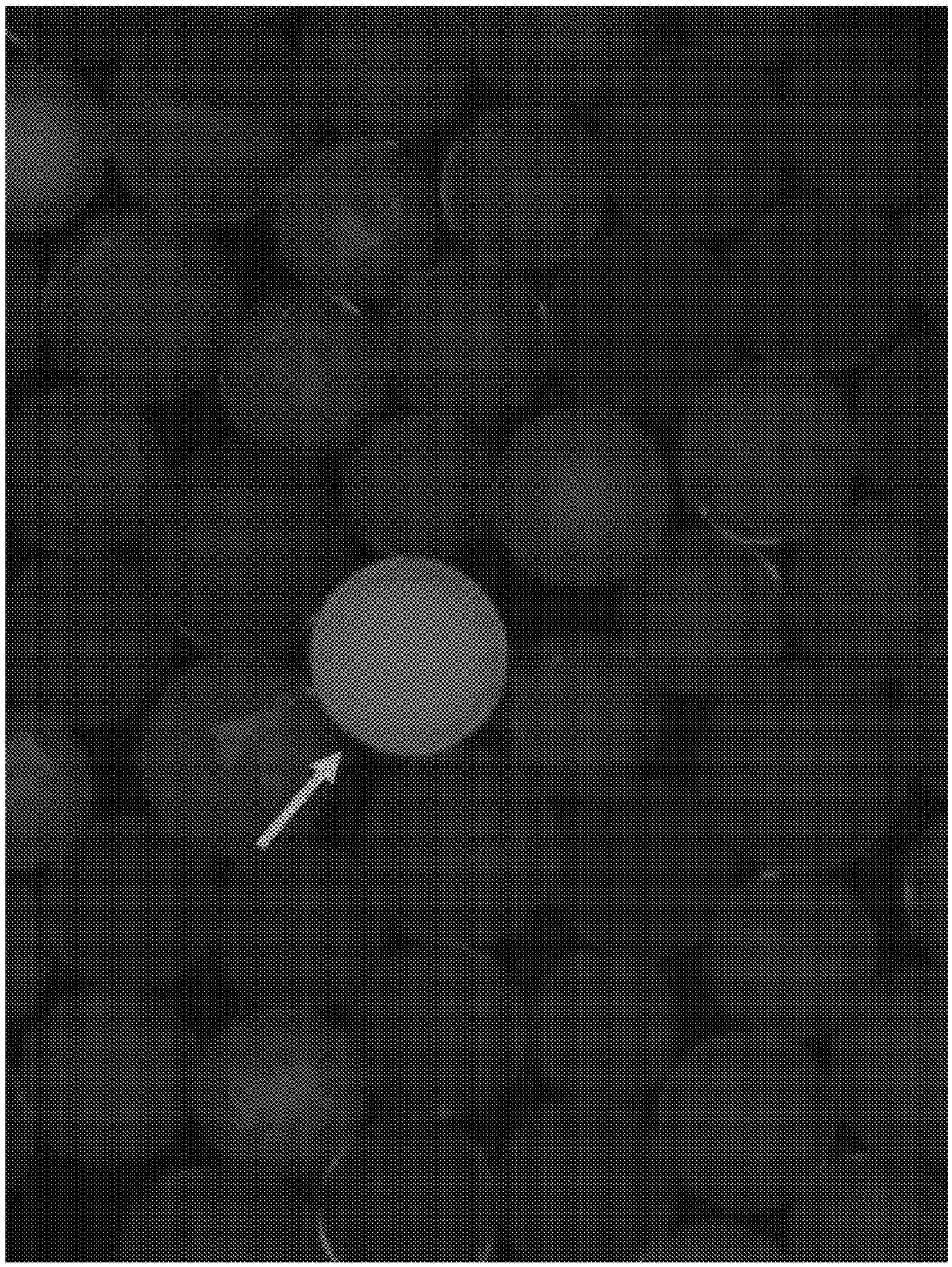
FIG. 7. Representative picture of beads for screening. The brightly red bead is the putative positive bead which was picked up manually.
Figure 8:
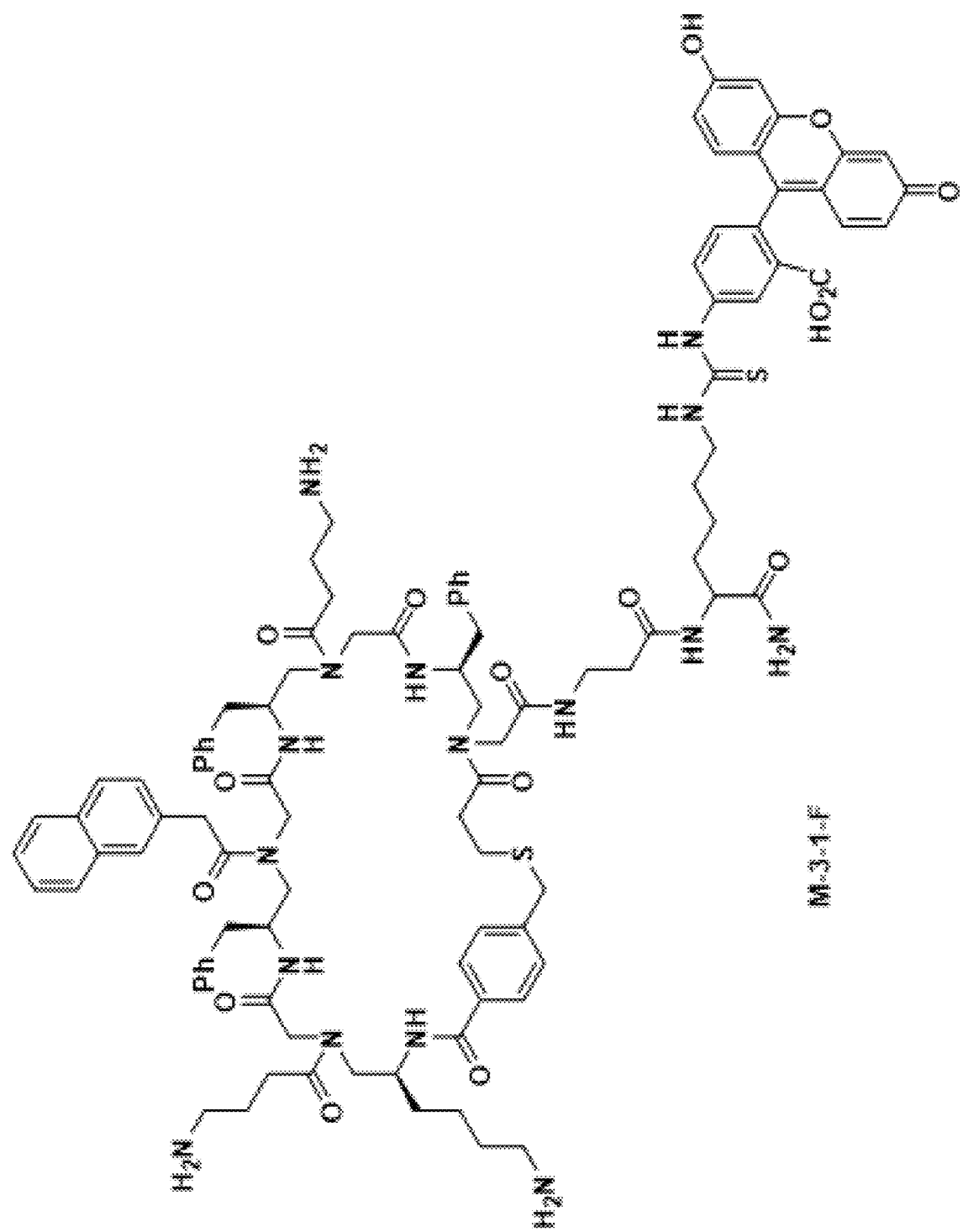
FIG. 8. Chemical structures of FITC-labeled cyclic γ-AA-peptides determined by MS/MS.
Figure 8:
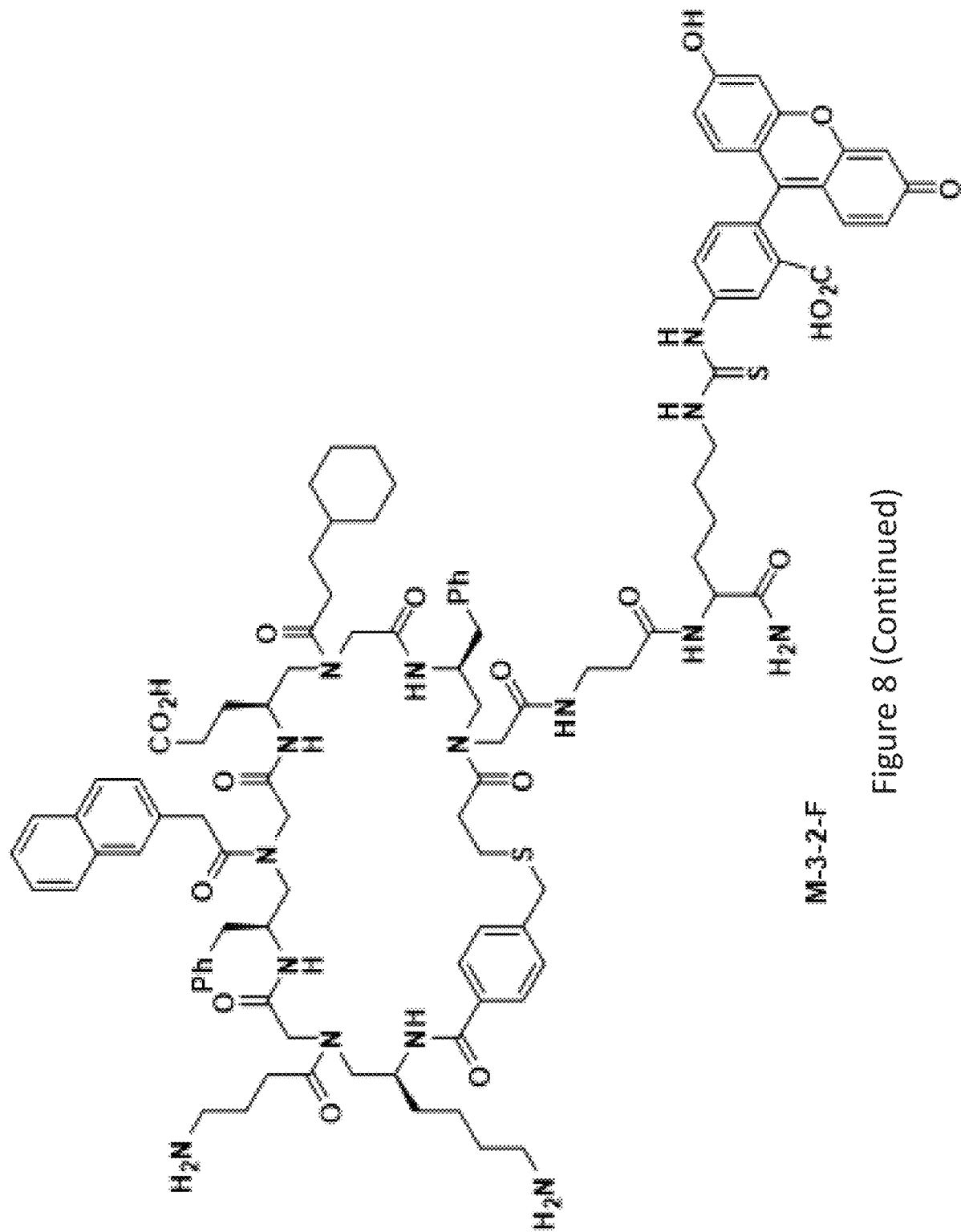
Figure 8:
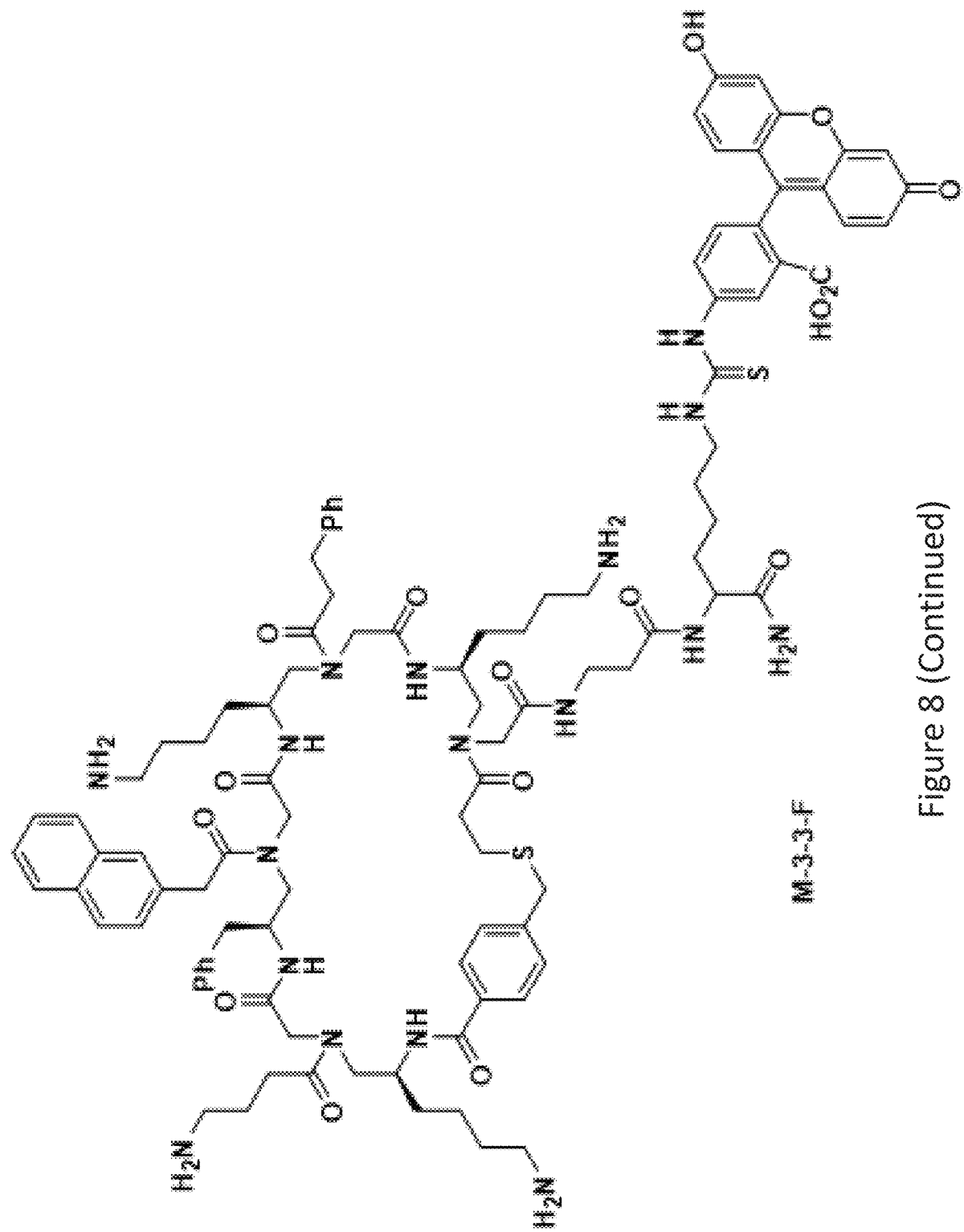
Figure 8:
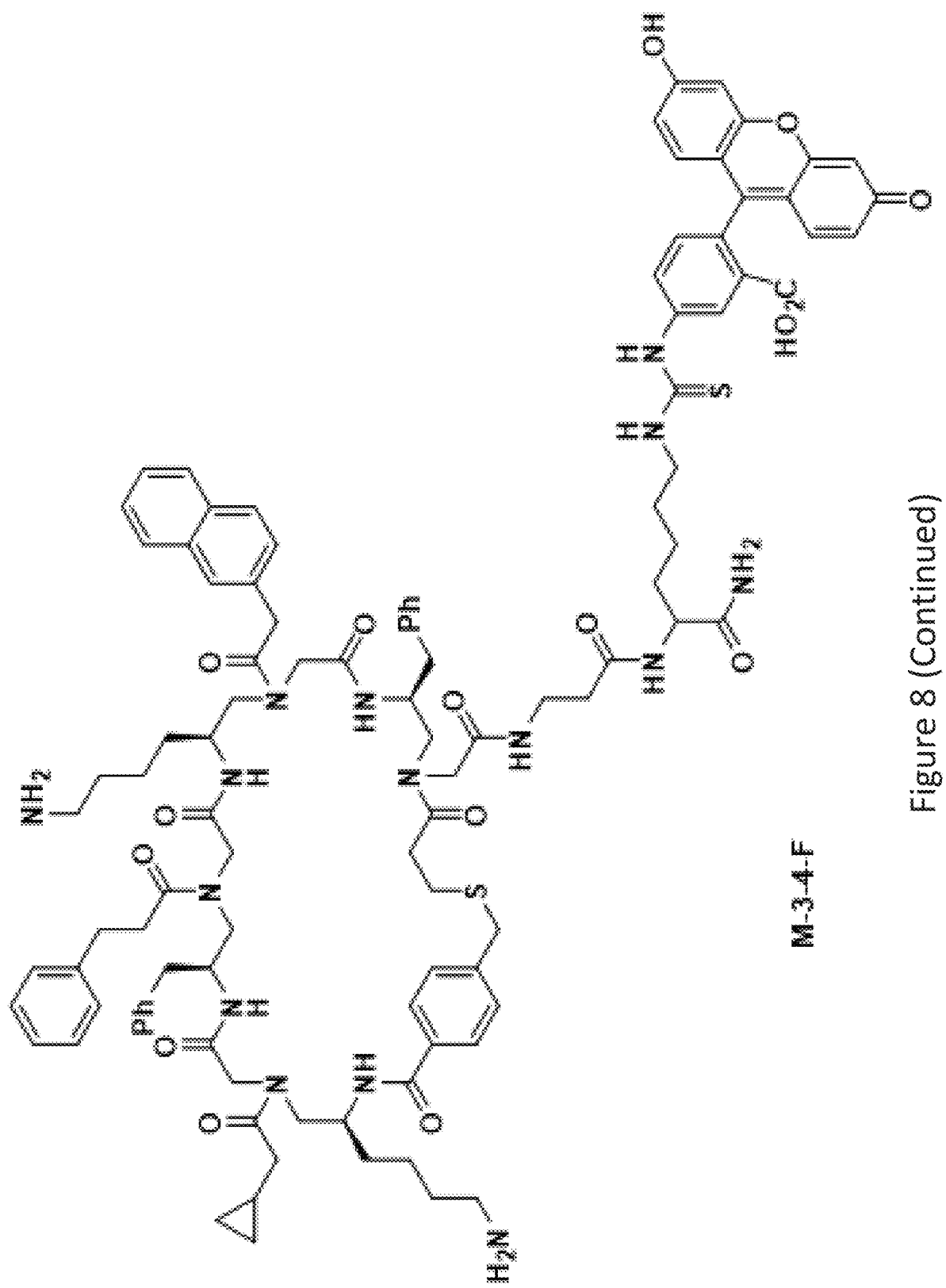
Figure 8:
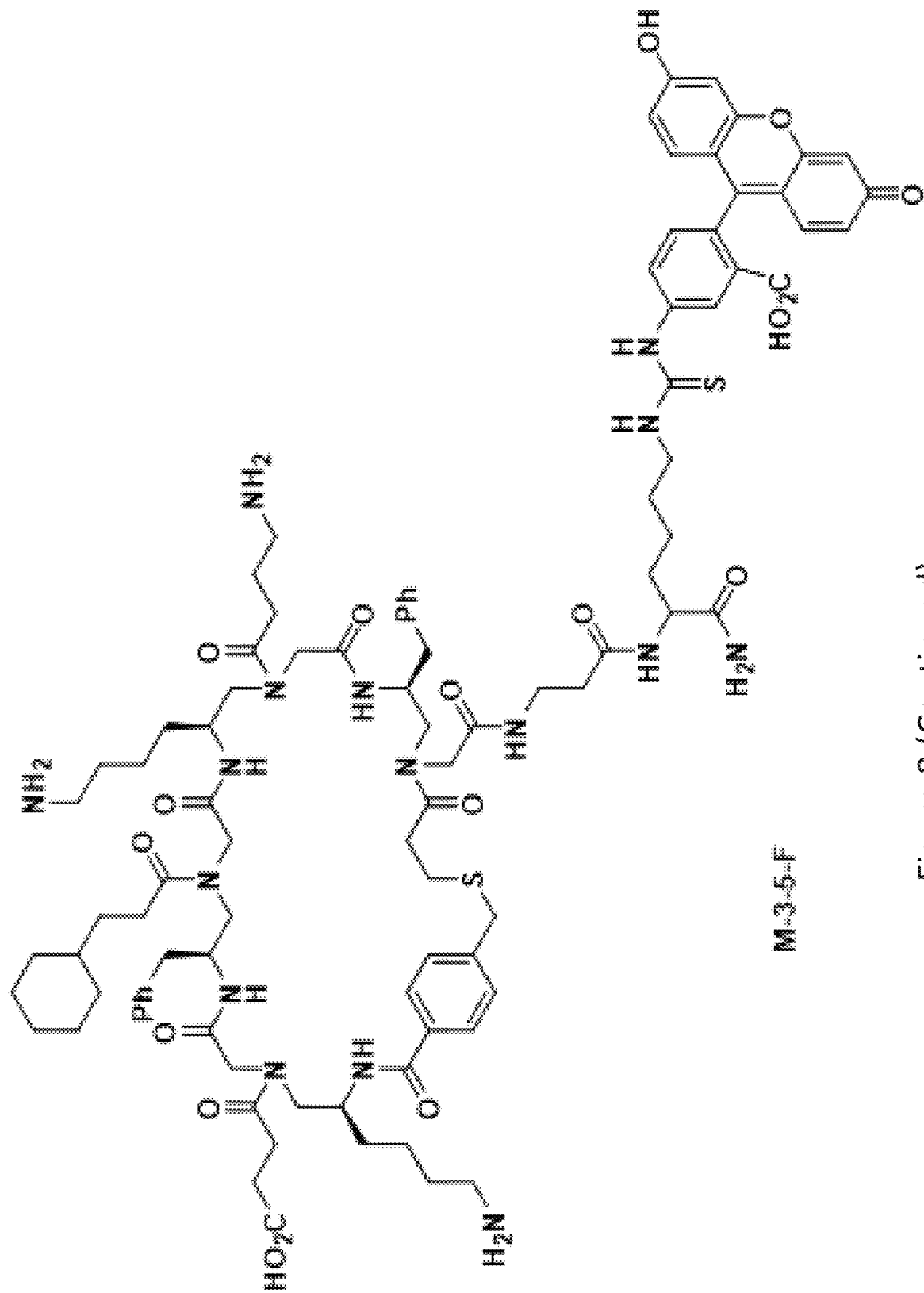
Figure 8:
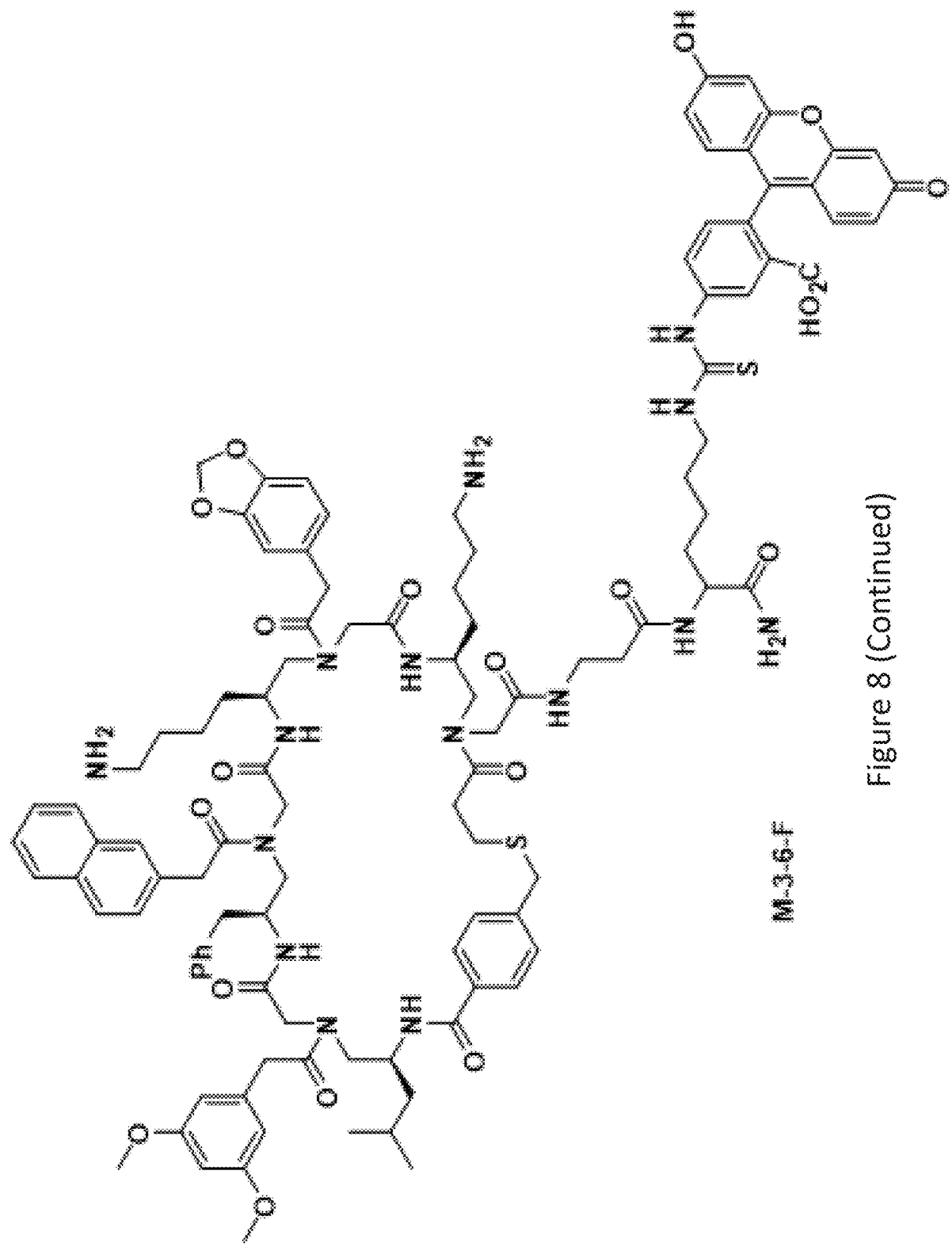
Figure 9:
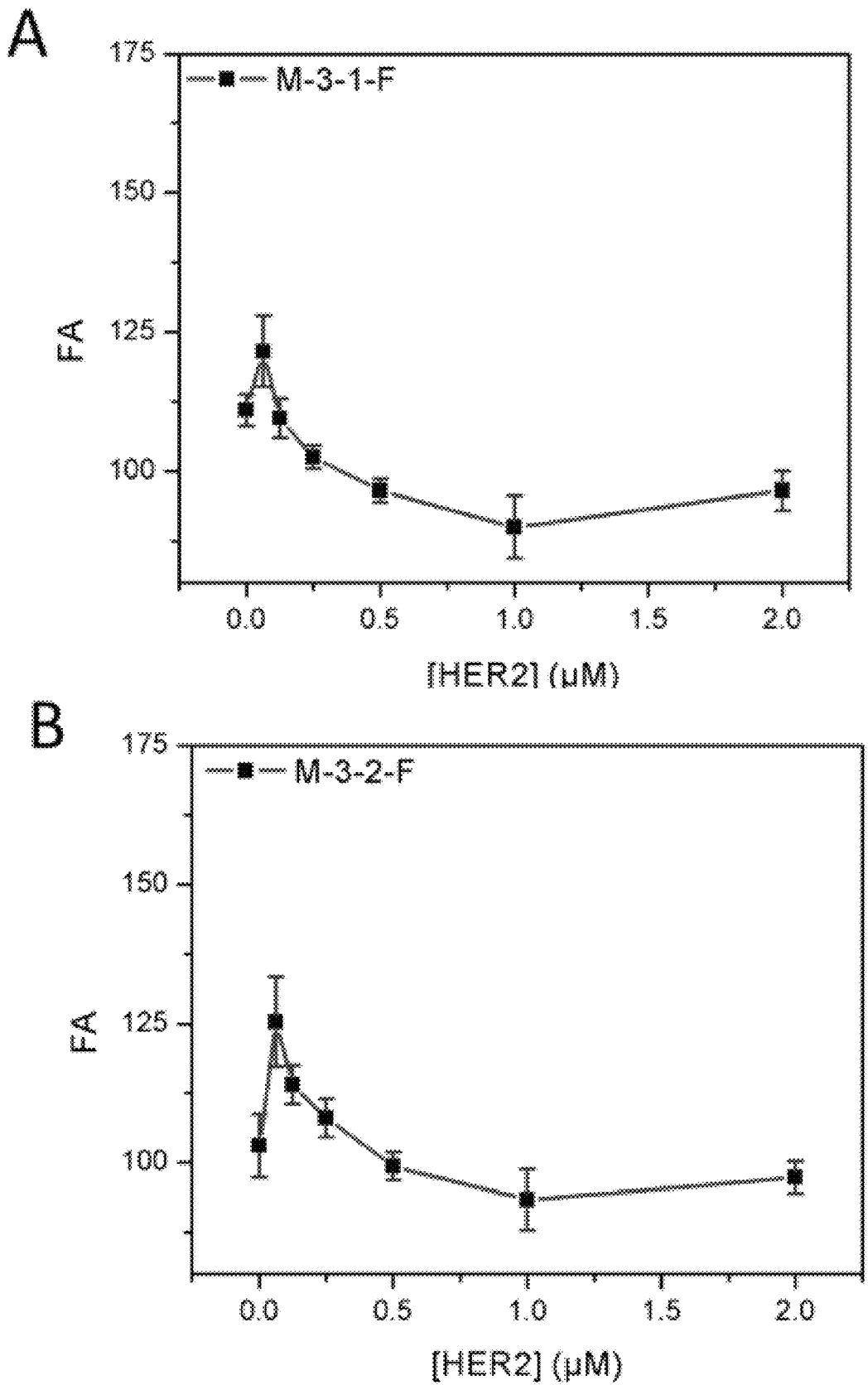
FIG. 9. The Binding affinity of M-3-1-F (A), M-3-2-F (B), M-3-3-F (C), M-3-4-F (D), M-3-5-F (E) and M-3-6-F (F) to HER2 measured by Fluorescence polarization (FP) assay. M-3-6-F had a strong binding to HER2 with a KD value of 278.3 nM.
Figure 9:
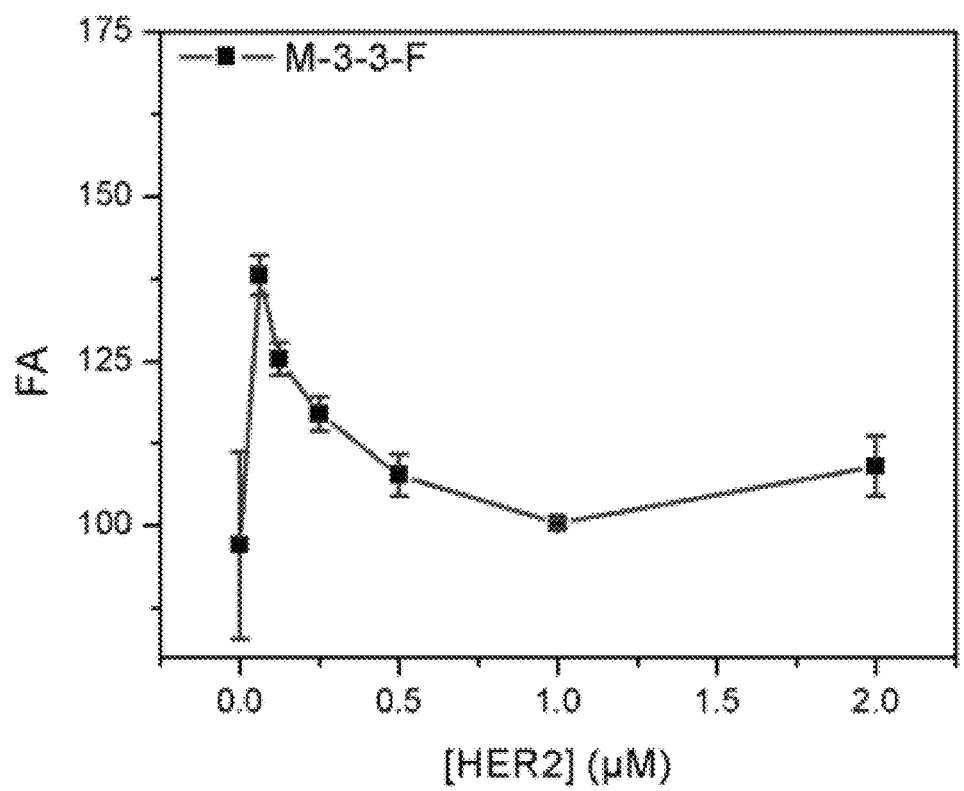
Figure 9:
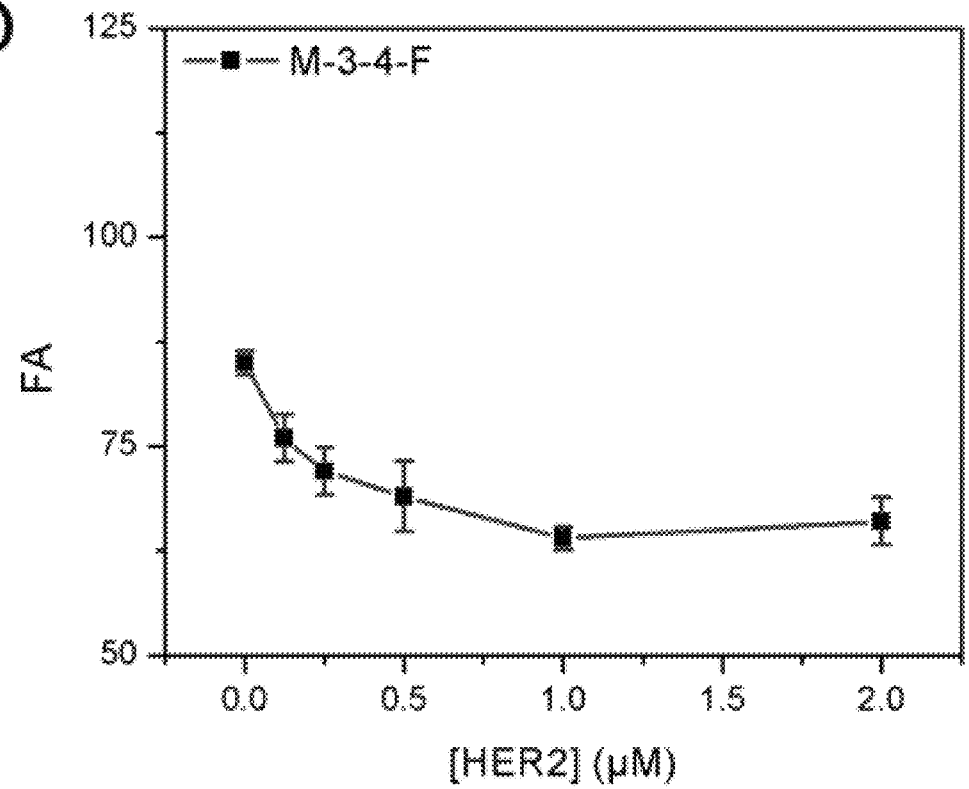
Figure 9:
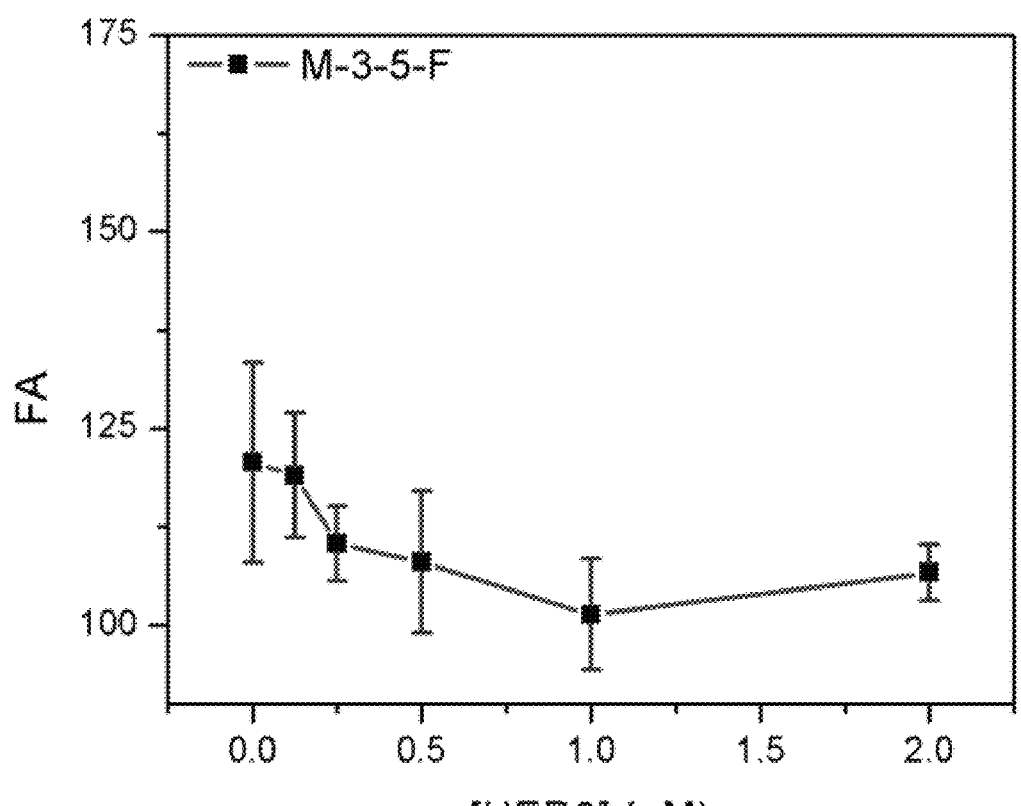
Figure 9:
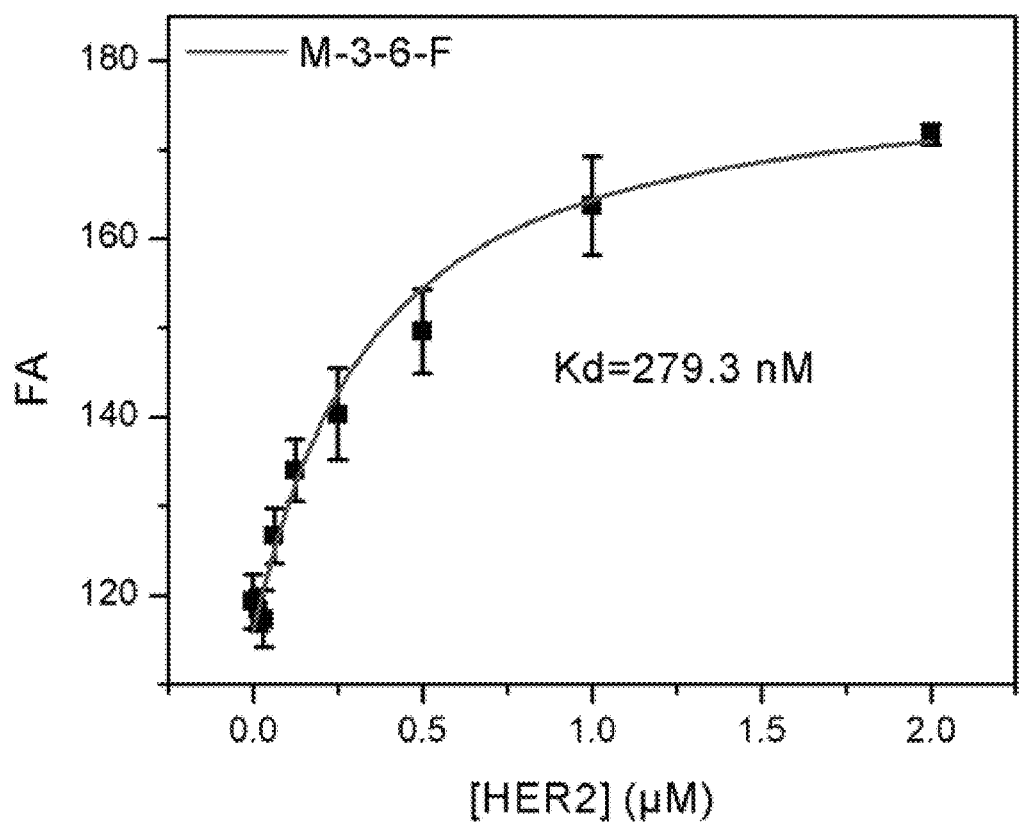

After synthesis, the linear decoding tag of ten randomly selected beads were cleaved off by treatment with CNBr and subsequently analyzed by MALDI-TOF MS/MS. The result showed that eight beads had unambiguous MS/MS fragmentation patterns, suggesting the quality of the beads was excellent. Subsequently, the high-throughput screening for the HER2 protein was directly performed with the library using the protocol detailed in the supporting information[22-24]. Briefly, to avoid the nonspecific binding and to improve the screening efficiency, prescreening was firstly performed, then the OBTC library was incubated with Fc-Tagged recombinant HER2 protein, followed by incubation with Goat anti-human IgG Fc cross adsorbed secondary antibody labeled with Dylight 549 (FIG. 3B). After a thorough wash, six beads that emitting intensive red fluorescence (FIG. 7) were isolated from the library under a fluorescence microscope. These beads were treated with guanidium chloride (GdmCl) and then the linear encoding peptides in the inner layers of the beads were cleaved off and subsequently sequenced by tandem MS/MS of MALDI (FIG. 3B). As a result, all putative hits were determined unambiguously. Then fluorescein labeled putative hits (FIG. 8) were resynthesized on a larger scale individually and test for their ability to bind to HER2 in vitro by fluorescence polarization (FP) assay. Among them, one hit M-3-6-F exhibited strong binding affinity toward HER2 with a $K_D$ of 0.28 μM (Figure S3 in supporting information).

Design and Synthesis of Artificial Antibody Surrogate M-3-6-D.

Figure 4:
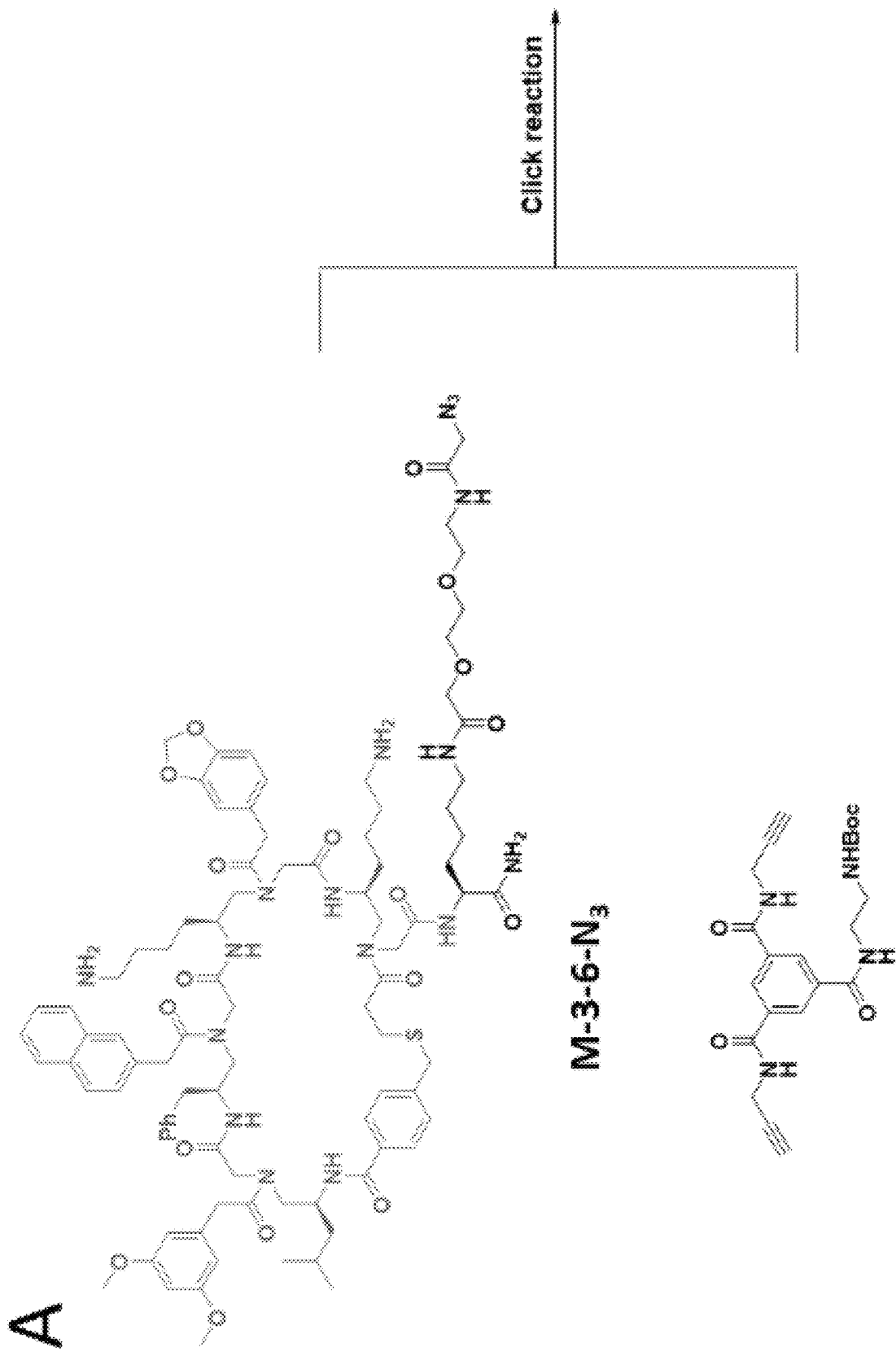
FIG. 4. (A) The design and synthesis of M-3-6-D. (B) Chemical structure of cyclic γ-AApeptide M-3-6. (C) HPLC analytical trace of M-3-6-D after incubation with pronase (0.1 mg/mL) in 100 mM ammonium bicarbonate buffer at 37° C. for 24 h.
Figure 4:
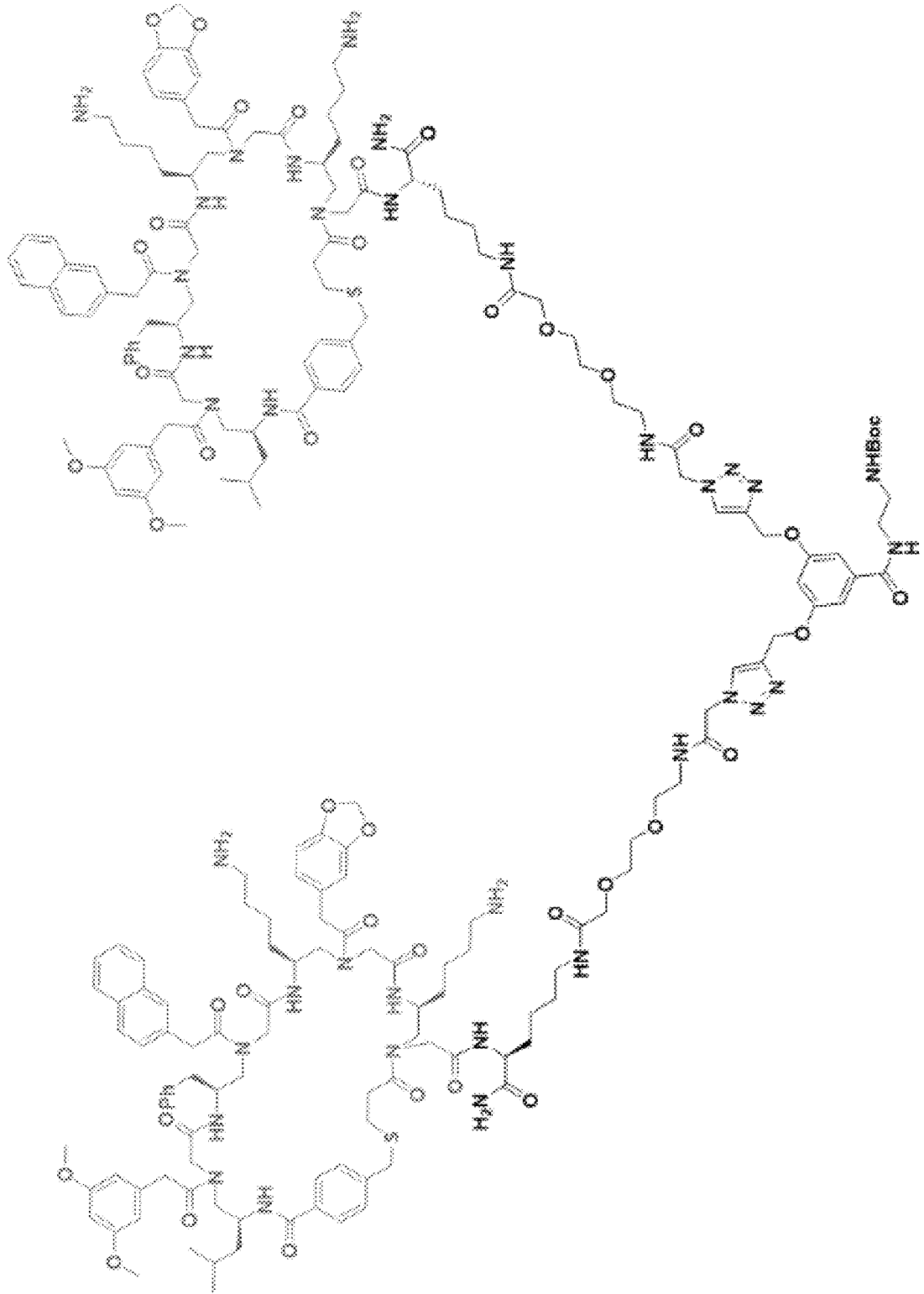
Figure 4:
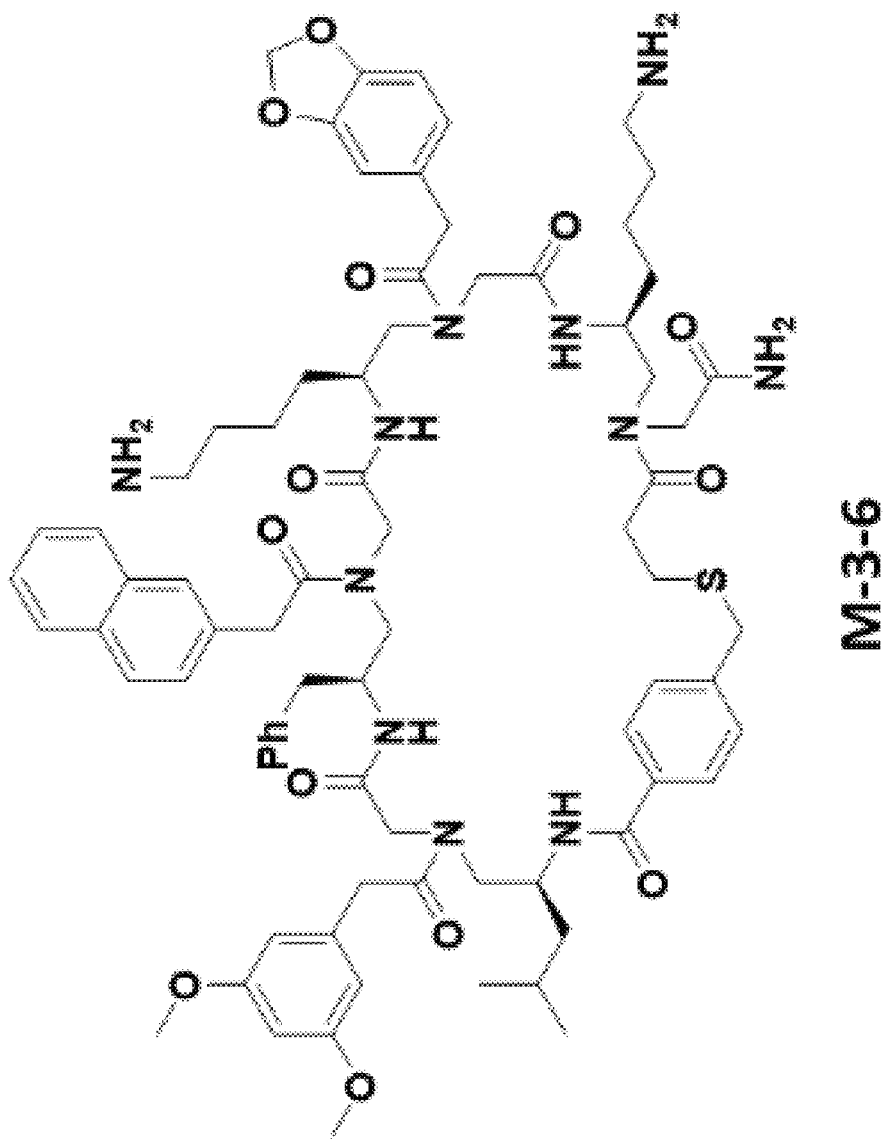
Figure 4:
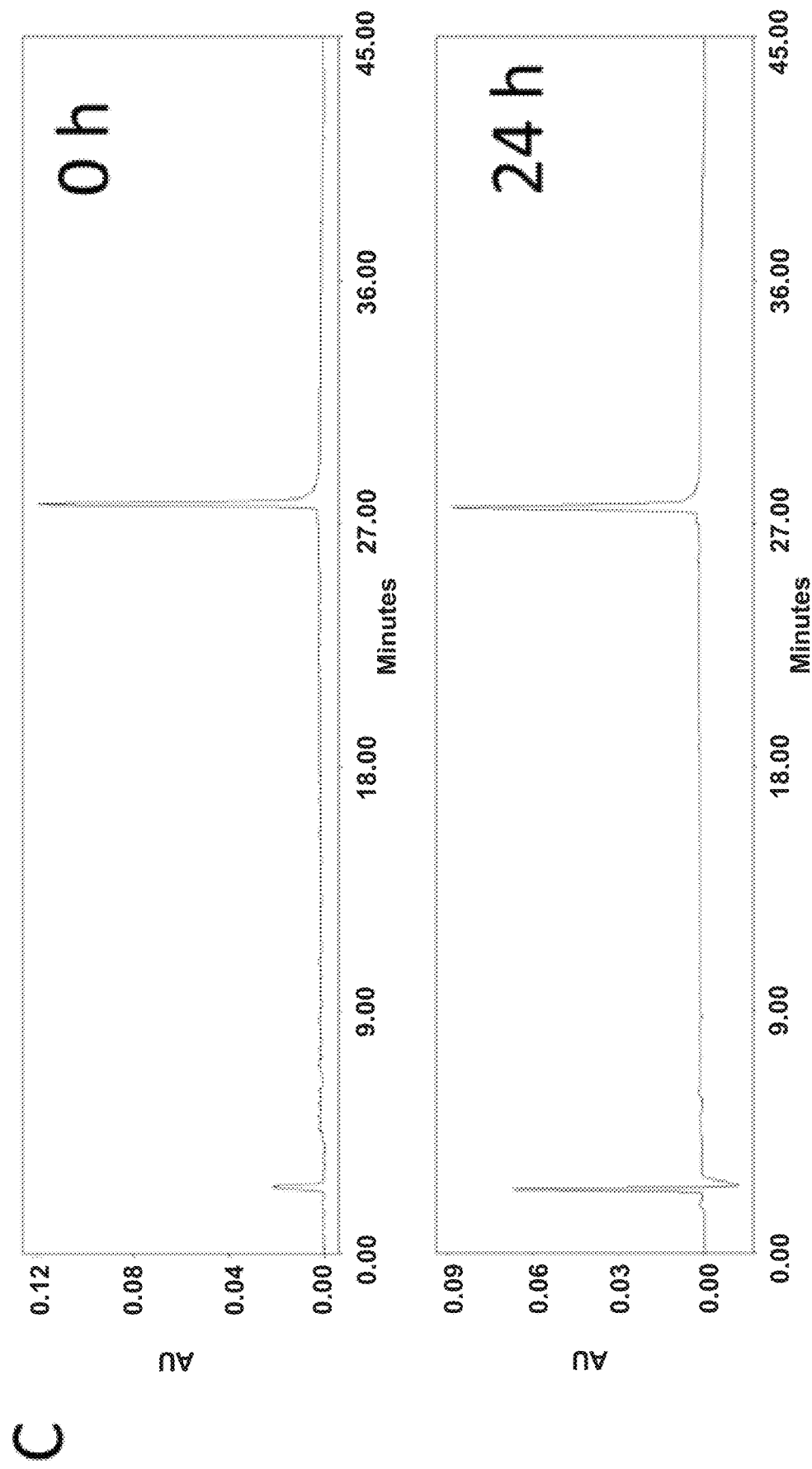

The strong binding affinity of M-3-6 (FIG. 4B) prompted us to move forward for the design of γ-AApeptides based artificial antibody. Dimerization strategy has been widely used to enhance the binding affinity of ligands toward protein targets, so as to develop unnatural antibody surrogate[25-29]. Using the similar strategy, since M-3-6 could mimic a binding loop domain of the "Y" shaped monoclonal antibody (FIG. 2B), we could make a dimer of M-3-6 using a linker so as to mimic the two binding loop domains of antibody. As shown in FIG. 4A, an antibody-like dimer of M-3-6 could be designed in a very straightforward manner, which took advantage of the alkyne-azide click reaction with high reactivity for dimerization. Briefly, azide modified cyclic γ-AApeptide M-3-6-$N_3$ bearing a PEG linker to improve the solubility was synthesized on solid phase synthesis and then purified by HPLC, which could be dimerized with di-alkyne linker by click reaction to form M-3-6-D (FIG. 4A) that could possess the similar function as antibody. It should be noted that the length of PEG linker could be changed, thereby making it easily accessible to further optimize and enhance binding activity of this class of artificial antibody in the future.

Binding Affinity of M-3-6, M-3-6-D

Next, the binding affinity of both M-3-6 and M-3-6-D to HER2 ECD in vitro were measured by surface plasmon resonance (SPR) assay (FIG. 10 in supporting information). M-3-6 shows a strong binding affinity to HER2 with a $K_D$ of 228 nM, which is highly consistent with the FP assay. As anticipated, the proposed artificial antibody, M-3-6-D, exhibited an excellent binding affinity toward HER2 with a $K_D$ of 30 nM, which has a ~7-fold improvement of binding compared with monomer M-3-6, demonstrating the strategy of novel antibody-like design. In addition, EGFR, known as ERBB1, another member of the human epidermal growth factor receptor family was chosen to test the selectivity of M-3-6. The SPR assay shows that M-3-6 exhibited a 10-fold weaker binding to EGFR with a $K_D$ of 1.95 μM, demonstrating the good binding selectivity of M-3-6 to HER2 (Fig. S5 in supporting information).

Stability of M-3-6-D Toward Proteolysis

As M-3-6-D shows strong binding ability to HER2 in vitro, we further evaluated its proteolysis stability toward pronase (the pronase theoretically digesting peptides into single amino acids) in buffer, which is critical for their biological activity. Upon incubation with pronase in 100 mM ammonium bicarbonate buffer at 37° C. for 24 h, no detectable degradation was observed for M-3-6-D monitored by HPLC (FIG. 4C), demonstrating its extraordinary stability against proteolytic degradation.

Inhibition of HER2, AKT, ERK Phosphorylation In Vitro

Having confirmed the binding activity in vitro, we set out to test the monomer M-3-6 and antibody-like M-3-6-D for their ability to modulate HER2-mediated signaling pathways in cellular assays. Unlike HER1, HER3 and HER4, which interact with specific sets of ligands, HER2 has no known direct activating ligand but instead is constitutively able to activate by heterodimerization with other ligand-activated family members such as HER1 and HER34'[30] Upon heterodimerization, conformational changes lead to autophosphorylation and initiation of divergent signal transduction cascades, and the PI3K/AKT axis and the Raf/MAPK cascade are the two most important and most extensively studied downstream signaling pathways that are activated by the HER receptors[31-33]. Our cyclic γ-AApeptides, especially for our antibody-like M-3-6-D, which have potent binding affinity to HER2 ECD and may have the ability to inhibit HER2 heterodimerization (FIG. 5A), thereby inhibiting phosphorylation and downstream signal transduction.

As such, HER2-positive SKBR3 cells[34] were incubated with M-3-6 or M-3-6-D for 4 h and cell lysates were analyzed by western blotting. As shown in FIG. 5B, treatment of SKBR3 cells with M-3-6 (0-30 µM) for 4 h resulted in a concentration-dependent inhibition of HER2 phosphorylation with an $IC_{50}$ of 12.9 µM, suggesting the compound blocked HER2 heterodimerization. Furthermore, downstream activation of phosphorylation of both AKT and ERK were also inhibited by M-3-6 in vitro with the consistent potency ($IC_{50}$ for P-AKT is 16.9 µM; and $IC_{50}$ for P-ERK is 10.6 µM) in a dose-dependent manner. As expected, the antibody-like molecule M-3-6-D showed even stronger inhibition of phosphorylation than M-3-6, which is in agreement with their binding affinity to HER2. As shown in FIG. 5C, the expression of P-HER2 was almost complete blocked with the treatment of 10 µM M-3-6-D, while the expression of P-HER2 was relatively high with the incubation of M-3-6 at the same concentration (FIG. 5B). In addition, for the regulation of downstream signaling pathways, it is very interesting that M-3-6-D showed more pronounced effect on the suppression of P-ERK compared with P-AKT, which may be provide mechanistic insight into the HER2 mediated cell signaling. Together, these data indicated that both M-3-6 and M-3-6-D are potent inhibitors of HER2 and its downstream signaling pathways, and M-3-6-D demonstrated considerably higher efficiency which confirmed the antibody-like dimer design strategy.

M-3-6, M-3-6-D Inhibited Cell Proliferation in Vitro

Cell proliferation assay was subsequently carried out to further analyzed the effect of both M-3-6 and M-3-6-D on EGF-driven proliferation of SKBR3 cells in vitro, which is an important outcome of tumorigenesis. SKBR3 cells were treated with serum-reduced EGF-containing (100 ng/mL) McCoy's 5A Medium in the presence of M-3-6 and M-3-6-D at different concentration (0-30 µM) for 72 h. As shown in FIG. 5D, SKBR3 cells showed significantly enhanced proliferation upon the stimulation of EGF, in contrast, a significantly antiproliferative activity of M-3-6 on EGF-stimulated cells was observed in a dose-dependent manner with an $IC_{50}$ of 17.9 µM. It is intriguing that again M-3-6-D exhibited much stronger suppression of cells growth ($IC_{50}$ is 1.66 µM), which illustrated its therapeutic potential as novel anticancer agent.

The Short-Term Therapeutic Efficacy of M-3-6 and M-3-6-D in Vivo.

To further assess the potential of the new compounds as anticancer therapeutics, we evaluated the antitumor activity of both M-3-6 and M-3-6-D in a SKBR3 xenograft mouse model. The SKBR3 tumor xenograft mice were administrated with PBS (control), M-3-6 (8 mg/kg or 32 mg/kg), M-3-6-D (8 mg/kg) or trastuzumab (8 mg/kg) by intraperitoneral (i.p.) injection respectively every two days for two weeks. The mice were allowed to grow for another 12 days before sacrifice. As shown in FIG. 6A, the injection of M-3-6 or M-3-6-D has ignorable effect on the body weight gain of SKBR3 tumor xenograft mice, indicating they negligible systematic cytotoxicity. The tumor size was measured with calipers showed extensive growth of the PBS-treated tumor. Though no significant reduction in tumor volume was observed of 8 mg/kg M-3-6 treatment, M-3-6 in higher dose (32 mg/kg) showed a much more improved antitumor effect, particularly in the period of drug administration. In comparison, antibody-like molecule M-3-6-D showed a significant antitumor effect, which is very comparable to that of the marketed monoclonal antibody Trastuzumab in the same concentration (FIG. 6B). It should be noted that after the last drug injection on day 12, the significant reduction in tumor volume was still observed for trastuzumab and antibody-like M-3-6-D, suggesting that M-3-6-D exhibited antibody-like prolonged anticancer activity. On the contrary, a significant tumor growth was found between the PBS group and M-3-6 treatment, which may suggest binding affinity of ligands is crucial for continuous anticancer therapeutic effect. Subsequently, after mice were sacrificed, tumors were resected, and the phosphorylation level of HER2 in the SKBR3 tumor sections was analyzed by immunohistochemical staining. As shown in FIG. 6C, consistent to tumor volume, M-3-6 showed modest inhibitory effect, but antibody-like molecule M-3-6-D has comparable efficiency with trastuzumab. Taken together, these data show that M-3-6-D exhibits similar antitumor effectiveness compared to trastuzumab in SKBR3 xenografted model, which could be further investigated for promising clinical anti-cancer drug development.

CONCLUSION we reported the development of novel artificial antibody by using a proper linker to dimerize two cyclic γ-AApeptides, so as to mimic both binding loops of monoclonal antibody. We demonstrated this strategy by identifying a novel HER2 inhibitor, cyclic γ-AApeptide M-3-6 through an OBTC combinatorial library screening, which could bind toward HER2 with high affinity and selectivity, and inhibited HER2-mediated phosphorylation and downstream signaling transduction. The dimerization of M-3-6 using a properly designed linker led to an antibody-like molecule M-3-6-D, which showed remarkable binding affinity to HER2. This artificial antibody M-3-6-D could potently inhibit HER2 phosphorylation and downstream signal transduction, as well as suppressing cell proliferation. More importantly, M-3-6-D also demonstrated a similar robust antitumor activity to mAb Trastuzumab in tumor xenografts. With the small molecular weight, remarkable resistance to proteolysis, as well as antibody-like property, M-3-6-D could be a promising candidate for the development of novel antibody surrogate for the new generation of anti-cancer therapeutics. Moreover, our strategy of artificial antibody surrogate based on dimers of cyclic peptidomimetics could be applied to a myriad of disease-related receptor targets in future.

Materials and Methods

One-Bead-Two-Compound Library Synthesis, Screening and Analysis

The one-bead-two-compound library was synthesized as our previous work[1]. 6.26 g TentaGel $NH_2$ resin was used for the library synthesis. The building blocks, side chains, linkers and Dde-protected amino acids that were used in this library were as followed.

For the HER2 targeted library screening, it contains two main parts, prescreening and screening.

Firstly, for the prescreening, all the TentaGel beads were swelled in DMF for 1 h. After being washed with Tris buffer for five times, the beads were equilibrated in Tris buffer overnight at room temperature, followed by incubation with the blocking buffer (1% BSA in Tris buffer with a 1000× excess of cleared E. coli lysate) for 1 h. After a thorough wash with Tris buffer, the beads were incubated with Goat anti-human IgG His cross adsorbed secondary antibody—Dylight 549 (1:1000 dilution) for 2 h at room temperature. The beads were washed with the Tris buffer for five times and then the beads emitting red fluorescence were picked up manually and excluded from formal screening.

Secondly, for the screening, the rest of beads after prescreening were washed with Tris buffer, and treated with 8 M guandine.HCl at room temperature for 1 h, followed by wash with DI water (5×), tris buffer (5×) and DMF (5×). The beads were then incubated in DMF for 1 h, followed by washing and equilibration in Tris buffer overnight. The beads were incubated in 1% BSA/Tris buffer and 1000× excess of E. coli lysate for 1 h at room temperature. After wash with Tris buffer for five times, the beads were incubated with HER2 protein at a concentration of 50 nM for 4 h at room temperature with a 1000× excess of E. coli lysate. After the thorough wash with Tris buffer, the library beads were incubated with and Goat anti-human IgG Fc cross adsorbed secondary antibody-Dylight 549 (1:1000 dilution) for 2 h at room temperature. The beads were washed with the Tris buffer for five times and then the beads emitting red fluorescence were picked up for future analysis.

For the hit structure analysis, each putative hit was transferred to an Eppendorf microtube, and denatured in 100 μL 8M guanidine.HCl for 1 h at room temperature respectively. The bead was rinsed with Tris buffer 3×10 min, water 3×10 min, DMF 3×10 min, and ACN 3×10 min. At last the resin was placed in ACN overnight in each microtube and then ACN was evaporated. The bead was incubated in the cocktail of 5:4:1 (v:v:v) of ACN: glacial acetic acid: $H_2O$ containing cyanogen bromide (CNBr) at a concentration of 50 mg/mL overnight at room temperature. The cleavage solution was then evaporated, and the cleaved peptide was dissolved in ACN: $H_2O$ (4:1) and subject to MALDI-TOF for MS/MS analysis.

All chemicals were purchased from commercial suppliers and used without further purification. Fmoc-protected amino acids were purchased from Chem-impex. TentaGel resin (0.23 mmol/g) was purchased from RAPP Polymere. Rink Amide-MBHA resin (0.55 mmol/g) was purchased from GL Biochem. Solid phase synthesis was conducted in peptide synthesis vessels on a Burrell Wrist-Action shaker. Cyclic γ-AApeptides were analyzed and purified on a Waters Breeze 2 HPLC system, and then lyophilized on a Labcono lyophilizer. The purity of the compounds was determined to be >95% by analytical HPLC. Masses of γ-AApeptides and the MS/MS analysis were obtained on an Applied Biosystems 4700 Proteomics Analyzer.

The SKBR3 cell lines were kindly provided by Prof. Lixin Wan at the Moffitt Cancer Center, Tampa, USA. HER2 was purchased from Creative BioMart; Anti-phospho-HER2 antibody was purchased from Thermo Fisher Scientific; Anti-phospho-AKT and Anti-phospho-ERK antibodies were from Cell Signaling Technology; GAPDH Loading control monoclonal antibody was purchased from Invitrogen.

Synthesis of Cyclic γ-AApeptides

The FITC-labeled hits were resynthesized on the Rink Amide resin[2]. Briefly, the Fmoc-Lys (Dde)-OH was first attached to the Rink amide resin. The Fmoc protection group was then removed, followed by the desired building blocks needed for the sequence synthesis. After the γ-AApeptides were cyclized, the Dde group was removed and Fmoc-β-Ala was added, the Fmoc protection group was then removed and FITC (2 equiv.) and DIPEA (6 equiv.) in DMF were added to the resin and shaken for 12 h at room temperature. The FITC labeled cyclic γ-AApeptides was cleaved by 1:1 (v/v) DCM/TFA containing 2% triisopropylsilane. The crude was purified by the Waters HPLC system.

M-3-1-F: MS: calcd. For $C_{102}H_{120}N_{16}NaO_{16}S_2^+[(M+Na)^+]$: 1913.2872; MALDI-TOF found: m/z 1913.3544

M-3-2-F: MS: calcd. For $C_{103}H_{126}N_{15}O_{18}S_2^+[(M+H)^+]$: 1926.3475; MALDI-TOF found: m/z 1926.4503

M-3-3-F: MS: calcd. For $C_{101}H_{127}N_{17}NaO_{16}S_2^+[(M+Na)^+]$: 1922.3392; MALDI-TOF found: m/z 1922.3264

M-3-4-F: MS: calcd. For $C_{105}H_{124}N_{15}O_{16}S_2^+[(M+H)^+]$: 1916.3555; MALDI-TOF found: m/z 1916.3585

M-3-5-F: MS: calcd. For $C_{96}H_{126}N_{16}NaO_{18}S_2^+[(M+Na)^+]$: 1879.2672; MALDI-TOF found: m/z 1878.5530

M-3-6-F: MS: calcd. For $C_{107}H_{128}N_{15}O_{20}S_2^+[(M+H)^+]$: 2008.4055; MALDI-TOF found: m/z 2008.4491

The synthesis of M-3-6 was conducted on the Rink Amide resin with general solid phrase synthesis. After the γ-AA-peptides were cyclized, the compound was cleaved by 1:1 (v/v) DCM/TFA containing 2% triisopropylsilane and purified by the Waters HPLC system.

M-3-6: MS: calcd. For $C_{77}H_{99}N_{11}NaO_{13}S^+[(M+Na)^+]$: 1441.7522; MALDI-TOF found: m/z 1441.2733

The synthesis of M-3-6-$N_3$ was conducted on the Rink Amide resin. Briefly, the Fmoc-Lys (Dde)-OH was first attached to the Rink amide resin. The Fmoc protection group was then removed, followed by the desired building blocks needed for the sequence synthesis. After the γ-AApeptides were cyclized, the Dde group was removed and FmocNH-$PEG_2$-$CH_2CO_2H$ was added, the Fmoc protection group was then removed and 2-Azidoacetic acid was added to the resin and shaken for 3 h at room temperature. The FITC labeled cyclic γ-AApeptides was cleaved by 1:1 (v/v) DCM/TFA containing 2% triisopropylsilane. The crude was purified by the Waters HPLC system.

M-3-6-$N_3$: MS: calcd. For $C_{91}H_{124}N_{17}O_{18}S^+[(M+Na)^+]$: 1774.9025; MALDI-TOF found: m/z 1775.6213

For the Synthesis of M-3-6-D

M-3-6-$N_3$ (10 mg, 0.0056 mmol) and linker (0.95 mg, 0.0026 mmol) was dissolved in DMSO (1 mL), then $CuSO_4 \cdot 5H_2O$ (1.4 mg, 0.0056 mmol, dissolved in 100 μL DI water) and sodium ascorbate (2.2 mg, 0.0112 mmol, dissolved in 100 DI water) were added respectively. The mixture was stirred at room temperature overnight and purified by the Waters HPLC system.

M-3-6-D: HRMS (ESI): Calcd. For $C_{202}H_{270}N_{36}O_{41}S_2$: 3919.9258; found: 1308.3184 $[M+3H]^{3+}$, 981.4900 $[M+4H]^{4+}$.

Fluorescence Polarization Assay

The FP experiment was performed by incubating 50 nM FITC labeled AApeptides with HER2 (0 to 2 μM) in PBS. Dissociation constants (Kd) was determined by plotting the fluorescence anisotropy values as a function of protein concentration, and the plots were fitted to the following equation. The Lst is the concentration of the AApeptides and the x stands for the concentration of the protein. The experiments were conducted in triplicates and repeated for three times.

$y=FPmin+(FPmax-FPmin)*(KD+Lst+x-sqrt((KD+Lst+x)^2-4*Lst*x))/(2*Lst)$

Surface Plasmon Resonance Assay

Binding kinetics of M-3-6 or M-3-6-D to HER2 was measured by surface plasmon resonance (OpenSPR, Nicoyalife). After HER2 was covalently coupled to the carboxyl sensor chips (Nicoyalife), M-3-6 or M-3-6-D in PBS running buffer (pH 7.4) was slowly flowed over the sensor chip for 5 min to allow interaction. The running buffer was then allowed to flow for 10 min to collect the dissociation data. After subtracting the background, the signal response vs. time curve was obtained, binding kinetic parameters were obtained by fitting the curve to a one-to-one binding model using Trace-Drawer (Nicoyalife) software.

Enzymatic Stability Assay

Cyclic γ-AApeptides M-3-6-D (0.1 mg/mL) were incubated with 0.1 mg/mL protease in 100 mM ammonium bicarbonate buffer (pH 7.8) at 37° C. for 24 h. Then, the reaction mixtures were concentrated in a speed vacuum to remove water and ammonium bicarbonate. The resulting residues were re-dissolved in $H_2O$/MeCN and analyzed on a Waters analytical HPLC system.

Cell Cultures and Inhibition of EGF-Induced Cell Proliferation

SKBR3 cells were cultured in McCoy's 5A Medium (Gibco) medium containing 10% fetal bovine serum and 1% penicillin/streptomycin in an atmosphere of 5% $CO_2$ at 37° C.

SKBR3 cells in good condition were seeded into a 96-well plate at a concentration of $1\times10^3$ cells/well in 100 μL of complete growth medium. After 24 hours of attachment at 37° C. and 5% $CO_2$, medium was replaced by fresh serum reduced McCoy's 5A Medium and cell were serum-starved overnight. Then serum-reduced EGF (100 ng/mL) McCoy's 5A Medium in the presence of different concentration of M-3-6 and M-3-6-D was added to the cells in hexaplicate. After 72 h, the CCK-8 reagents were added according to the manufacturer's recommendations.

Western Blot Assay

SKBR3 cells were seeded into a 6-well plate at a concentration of $1\times10^5$ cells/well. After 12 h attachment at 37° C. and 5% $CO_2$, the cells were starved overnight in serum-reduced McCoy's 5A Medium followed by treatment with different concentration of M-3-6 or M-3-6-D for 4 h, and then washed with ice-cold PBS and resuspended in ice-cold RIPA buffer supplemented with Halt Protease and Phosphatase Inhibitor Cocktail. Subsequently, the cells were incubated on ice for 10 min and centrifuged at 14,000×g at 4° C. for 10 min. An equal amount of protein was run on 4-12% Bis-Tris gels, transferred to polyvinylidene difluoride membranes (Millipore) and western blotted with anti-phosphorylated HER2, anti-phosphorylated AKT, anti-phosphorylated ERK and GAPDH. The experiments were conducted in triplicates and repeated for three times.

Antitumor Studies in Nude Mice

Male BALB/c nude mice, 4-6 weeks old, were provided by the Shanghai Bikai Experimental Animal Center, with the license number SOXK (Hu) 2008-0016, and maintained under specific-pathogen-free conditions. All animal protocols were approved by the Institutional Animal Use and Care Committee. All the experiments and animal care were approved by Shanghai Medical Experimental Animal Care Commission and in accordance with the Provision and General Recommendation of Chinese Experimental Animals Administration Legislation.

SKBR3 cells were harvested, resuspended in PBS, and injected subcutaneously into 4-6 weeks old Male BALB/c nude mice. When the tumors reach an average size of 100 $mm^3$, the mice were then randomized divided into four treatment groups: Control (PBS), M-3-6 (8 mg/kg), M-3-6 (32 mg/kg), M-3-6-D (8 mg/kg) and trastuzumab (8 mg/kg). Mice were injected through the intraperitoneal every two days for seven injections. 12 days after injection, the mice in each group were killed, and the tumors were removed for examination. The tumor volumes were determined by measuring length (1) and width (w) and calculating volume ($V=lw^2/2$).

For the immunohistochemical analysis, the hydrated paraffin section was incubated in a blocking solution (10% donkey serum +5% nonfat dry milk +4% BSA +0.1% Triton X-100) for 10 min, and then incubated at 4° C. overnight with anti-P-HER2, P-AKT, P-ERK. After washing with PBS, the sections were incubated with diluted (1:200) biotinylated secondary antibody for 30 min. Subsequently, the sections were washed again in PBS and incubated for 30 min with the preformed avidin-horseradish peroxidase macromolecular complex. Development of peroxidase reaction was achieved by incubation in 0.01% 3, 3-diaminobenzidine tetrahydrochloride (DAB) in PBS containing 0.01% hydrogen peroxide for approximately 5 min at room temperature. Sections were then washed thoroughly in tap water, counterstained in haematoxylin, dehydrated in absolute alcohol, cleared in xylene and mounted in synthetic resin for microscopic examination.

REFERENCES

1. Hynes, N. E.; Lane, H. A., ERBB receptors and cancer: the complexity of targeted inhibitors. *Nat. Rev. Cancer* 2005, 5 (5), 341-354.
2. Petrelli, F.; Tomasello, G.; Barni, S.; Lonati, V.; Passalacqua, R.; Ghidini, M., Clinical and pathological characterization of HER2 mutations in human breast cancer: a systematic review of the literature. *Breast Cancer Res. Tr.* 2017, 166 (2), 339-349.
3. King, C.; Kraus, M.; Aaronson, S., Amplification of a novel v-erbB-related gene in a human mammary carcinoma. *Science* 1985, 229 (4717), 974-976.
4. Arteaga, Carlos L.; Engelman, Jeffrey A., ERBB Receptors: From Oncogene Discovery to Basic Science to Mechanism-Based Cancer Therapeutics. *Cancer Cell* 2014, 25 (3), 282-303.
5. Burstein, H. J., The Distinctive Nature of HER2-Positive Breast Cancers. *N Engl. J. Med.* 2005, 353 (16), 1652-1654.
6. Vogel, C. L.; Cobleigh, M. A.; Tripathy, D.; Gutheil, J. C.; Harris, L. N.; Fehrenbacher, L.; Slamon, D. J.; Murphy, M.; Novotny, W. F.; Burchmore, M.; Shak, S.; Stewart, S. J.; Press, M., Efficacy and Safety of Trastuzumab as a Single Agent in First-Line Treatment of HER2-Overexpressing Metastatic Breast Cancer. *J. Clin. Oncol.* 2002, 20 (3), 719-726.
7. Capelan, M.; Pugliano, L.; De Azambuja, E.; Bozovic, I.; Saini, K. S.; Sotiriou, C.; Loi, S.; Piccart-Gebhart, M. J., Pertuzumab: new hope for patients with HER2-positive breast cancer. *Ann. Oncol.* 2012, 24 (2), 273-282.
8. Moy, B.; Goss, P. E., Lapatinib: Current Status and Future Directions in Breast Cancer. *Oncol.* 2006, 11 (10), 1047-1057.
9. Chan, A., Neratinib in HER-2-positive breast cancer: results to date and clinical usefulness. *Ther. Adv. Med. Oncol.* 2016, 8 (5), 339-350.
10. Garrett, J. T.; Arteaga, C. L., Resistance to HER2-directed antibodies and tyrosine kinase inhibitors. *Cancer Bio. Ther.* 2011, 11 (9), 793-800.
11. Xu, Z.-q.; Zhang, Y.; Li, N.; Liu, P. j.; Gao, L.; Gao, X.; Tie, X. j., Efficacy and safety of lapatinib and trastuzumab for HER2-positive breast cancer: a systematic review and meta-analysis of randomised controlled trials. *BMJ Open* 2017, 7 (3), e013053.
12. Scheuer, W.; Friess, T.; Burtscher, H.; Bossenmaier, B.; Endl, J.; Hasmann, M., Strongly Enhanced Antitumor Activity of Trastuzumab and Pertuzumab Combination Treatment on HER2-Positive Human Xenograft Tumor Models. *Cancer Res.* 2009, 69 (24), 9330-9336.
13. Baselga, J.; Cortes, J.; Kim, S.-B.; Im, S.-A.; Hegg, R.; Im, Y.-H.; Roman, L.; Pedrini, J. L.; Pienkowski, T.; Knott, A.; Clark, E.; Benyunes, M. C.; Ross, G.; Swain, S. M., Pertuzumab plus Trastuzumab plus Docetaxel for Metastatic Breast Cancer. *N Engl. J. Med.* 2011, 366 (2), 109-119.
14. Swain, S. M.; Baselga, J.; Kim, S.-B.; Ro, J.; Semiglazov, V.; Campone, M.; Ciruelos, E.; Ferrero, J.-M.; Schneeweiss, A.; Heeson, S.; Clark, E.; Ross, G.; Benyunes, M. C.; Cortes, J., Pertuzumab, Trastuzumab, and Docetaxel in HER2-Positive Metastatic Breast Cancer. *N Engl. J. Med.* 2015, 372 (8), 724-734.
15. Shi, Y.; Teng, P.; Sang, P.; She, F.; Wei, L.; Cai, J., γ-AApeptides: Design, Structure, and Applications. *Acc. Chem. Res* 2016, 49 (3), 428-441.
16. Teng, P.; Shi, Y.; Sang, P.; Cai, J., γ-AApeptides as a New Class of Peptidomimetics. *Chem. Eur. 1* 2016, 22 (16), 5458-5466.
17. Teng, P.; Ma, N.; Cerrato, D. C.; She, F.; Odom, T.; Wang, X.; Ming, L.-J.; van der Vaart, A.; Wojtas, L.; Xu, H.; Cai, J., Right-Handed Helical Foldamers Consisting of De Novo d-AApeptides. *J. Am. Chem. Soc.* 2017, 139 (21), 7363-7369.
18. She, F.; Teng, P.; Peguero-Tejada, A.; Wang, M.; Ma, N.; Odom, T.; Zhou, M.; Gjonaj, E.; Wojtas, L.; van der Vaart, A.; Cai, J., De Novo Left-Handed Synthetic Peptidomimetic Foldamers. *Angew. Chem. Int. Ed.* 2018, 57 (31), 9916-9920.
19. Teng, P.; Niu, Z.; She, F.; Zhou, M.; Sang, P.; Gray, G. M.; Verma, G.; Wojtas, L.; van der Vaart, A.; Ma, S.; Cai, J., Hydrogen-Bonding-Driven 3D Supramolecular Assembly of Peptidomimetic Zipper. *J. Am. Chem. Soc.* 2018, 140 (17), 5661-5665.
20. Teng, P.; Gray, G. M.; Zheng, M.; Singh, S.; Li, X.; Wojtas, L.; van der Vaart, A.; Cai, J., Orthogonal Halogen-Bonding-Driven 3D Supramolecular Assembly of Right-Handed Synthetic Helical Peptides. *Angew. Chem. Int. Ed.* 2019, 58 (23), 7778-7782.
21. Sang, P.; Zhang, M.; Shi, Y.; Li, C.; Abdulkadir, S.; Li, Q.; Ji, H.; Cai, J., Inhibition of β-catenin/B cell lymphoma 9 protein—protein interaction using α-helix—mimicking sulfono-γ-AApeptide inhibitors. *Proc. Natl. Acad. Sci. U S. A.* 2019, 116 (22), 10757-10762.
22. Shi, Y.; Challa, S.; Sang, P.; She, F.; Li, C.; Gray, G. M.; Nimmagadda, A.; Teng, P.; Odom, T.; Wang, Y.; van der Vaart, A.; Li, Q.; Cai, J., One-Bead—Two-Compound Thioether Bridged Macrocyclic γ-AApeptide Screening Library against EphA2. *J. Med. Chem.* 2017, 60 (22), 9290-9298.
23. Shi, Y.; Parag, S.; Patel, R.; Lui, A.; Murr, M.; Cai, J.; Patel, N. A., Stabilization of lncRNA GASS by a Small Molecule and Its Implications in Diabetic Adipocytes. *Cell Chem. Bio.* 2019, 26 (3), 319-330.e6.
24. Yan, H.; Zhou, M.; Bhattarai, U.; Song, Y.; Zheng, M.; Cai, J.; Liang, F.-S., Cyclic Peptidomimetics as Inhibitor for miR-155 Biogenesis. *Mol. Pharm.* 2019, 16 (2), 914-920.
25. Handl, H. L.; Sankaranarayanan, R.; Josan, J. S.; Vagner, J.; Mash, E. A.; Gillies, R. J.; Hruby, V. J., Synthesis and Evaluation of Bivalent NDP-α-MSH(7) Peptide Ligands for Binding to the Human Melanocortin Receptor 4 (hMC4R). *Bioconjugate Chemistry* 2007, 18 (4), 1101-1109.
26. Udugamasooriya, D. G.; Dineen, S. P.; Brekken, R. A.; Kodadek, T., A Peptoid "Antibody Surrogate" That Antagonizes VEGF Receptor 2 Activity. *J. Am. Chem. Soc.* 2008, 130 (17), 5744-5752.
27. Kodadek, T., Development of antibody surrogates for the treatment of cancers and autoimmune disease. *Curr. Opin. Chem. Bio.* 2010, 14 (6), 721-727.
28. Sarkar, M.; Liu, Y.; Morimoto, J.; Peng, H.; Aquino, C.; Rader, C.; Chiorazzi, N.; Kodadek, T., Recognition of Antigen-Specific B-Cell Receptors from Chronic Lymphocytic Leukemia Patients by Synthetic Antigen Surrogates. *Chem. Bio.* 2014, 21 (12), 1670-1679.
29. Sarkar, M.; Liu, Y.; Qi, J.; Peng, H.; Morimoto, J.; Rader, C.; Chiorazzi, N.; Kodadek, T., Targeting Stereotyped B Cell Receptors from Chronic Lymphocytic Leukemia Patients with Synthetic Antigen Surrogates. *J. Bio. Chem.* 2016, 291 (14), 7558-7570.
30. Garrett, T. P. J.; McKern, N. M.; Lou, M.; Elleman, T. C.; Adams, T. E.; Lovrecz, G. O.; Kofler, M.; Jorissen, R. N.; Nice, E. C.; Burgess, A. W.; Ward, C. W., The Crystal Structure of a Truncated ErbB2 Ectodomain Reveals an Active Conformation, Poised to Interact with Other ErbB Receptors. *Molecular Cell* 2003, 11 (2), 495-505.
31. Yarden, Y.; Pines, G., The ERBB network: at last, cancer therapy meets systems biology. *Nat. Rev. Cancer* 2012, 12 (8), 553-563.

32. Larionov, A. A., Current Therapies for Human Epidermal Growth Factor Receptor 2-Positive Metastatic Breast Cancer Patients. *Front Oncol* 2018, 8, 89-89.
33. Ritter, C. A.; Perez-Torres, M.; Rinehart, C.; Guix, M.; Dugger, T.; Engelman, J. A.; Arteaga, C. L., Human Breast Cancer Cells Selected for Resistance to Trastuzumab <em>In vivo</em> Overexpress Epidermal Growth Factor Receptor and ErbB Ligands and Remain Dependent on the ErbB Receptor Network. *Clin. Cancer Res.* 2007, 13 (16), 4909-4919.
34. Holliday, D. L.; Speirs, V., Choosing the right cell line for breast cancer research. *Breast Cancer Res.* 2011, 13 (4), 215.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A cyclic γ-amino acid peptide compound (cyclic γ-AA) comprising:

formula (i)

wherein R1 comprises H, a tag, a linker or a linker-tag complex.

2. The compound of claim 1, wherein R1 is a tag.

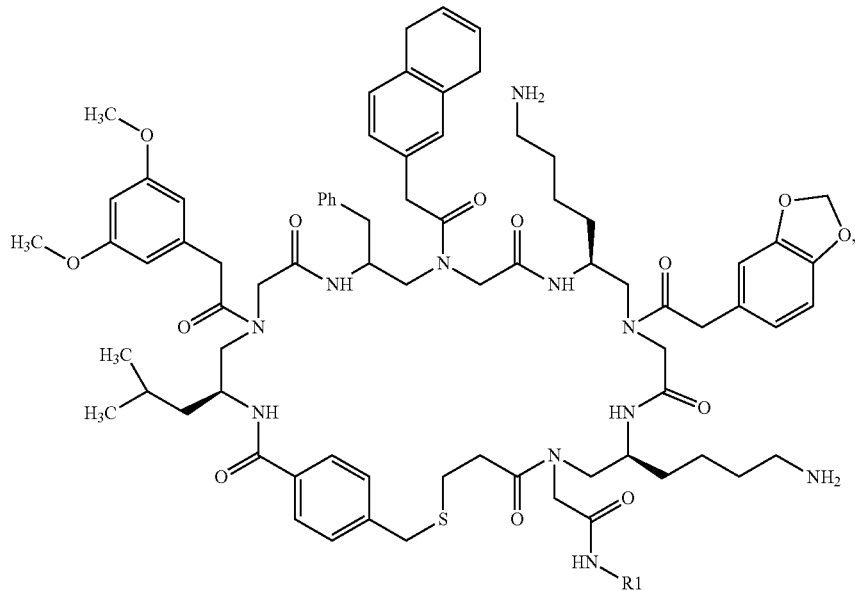

3. The compound of claim 2, wherein the tag is a fluorophore.
4. The compound of claim 3, wherein the tag is FITC, and the compound is formula (ii):
5. The compound of claim 1, wherein R1 is a linker.
6. The compound of claim 5, wherein the linker is selected from an unsubstituted $C_1$-$C_{20}$ alkyl, substituted $C_1$-$C_{20}$ alkyl, $C_2$-$C_{20}$ alkenyl, phenyl, phenyl substituted C1-C20
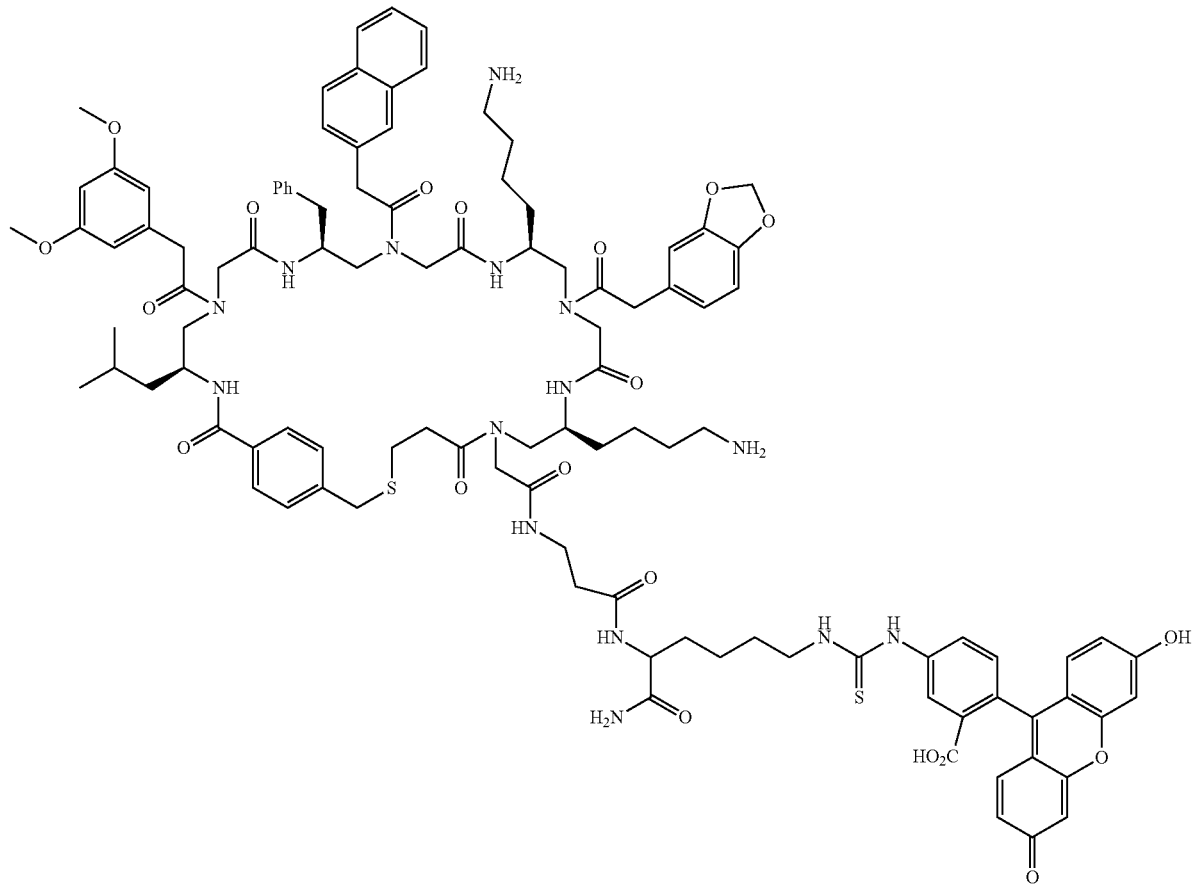 [SMILES: COc1cc(CC(=O)N2CC(=O)N[C@@H](Cc3ccccc3)CN(C(=O)Cc3ccc4ccccc4c3)CC(=O)N[C@@H](CCCCN)CN(C(=O)Cc3ccc4c(c3)OCO4)CC(=O)N[C@@H](CCCCN)CN(CC(=O)NCCC(=O)NC(CCCCNC(=S)Nc3ccc(-c4c5ccc(=O)cc-5oc5cc(O)ccc45)c(C(=O)O)c3)C(N)=O)C(=O)CCSCc3ccc(cc3)C(=O)N[C@@H](CC(C)C)C2)cc(OC)c1]

alkyl, cycloalkyl substituted $C_1$-$C_{20}$ alkyl, an amino acid, and polyethylene glycol (PEG).

7. The compound of claim 6, wherein the linker is a PEG chain, and the compound is formula (iii)

formula (i)-linker-formula (i), wherein the first and second formula (i) compounds are linked via a linker through R1.

9. The dimeric compound of claim 8, wherein the linker is selected from an unsubstituted $C_1$-$C_{20}$ alkyl, substituted $C_1$-$C_{20}$ alkyl, $C_2$-$C_{20}$ alkenyl, phenyl, phenyl substituted $C_1$-$C_{20}$ alkyl, cycloalkyl substituted $C_1$-$C_{20}$ alkyl, an amino acid, and polyethylene glycol (PEG).

8. A dimeric compound comprising the cyclic γ-AA of claim 1, wherein the structure of the dimeric compound is

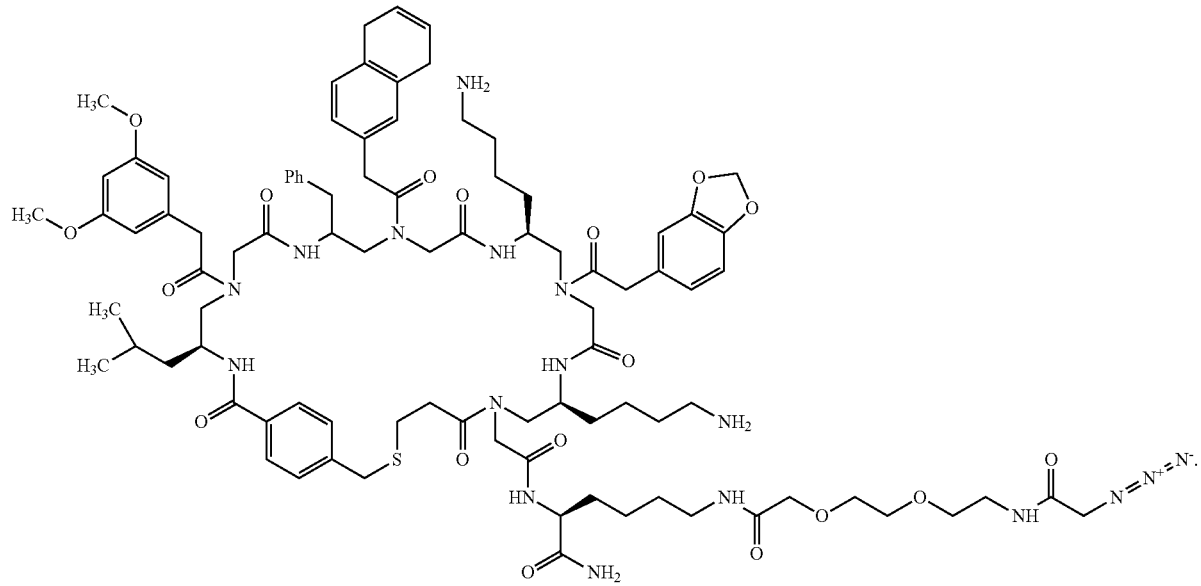

10. The dimeric compound of claim 9, wherein the compound is formula

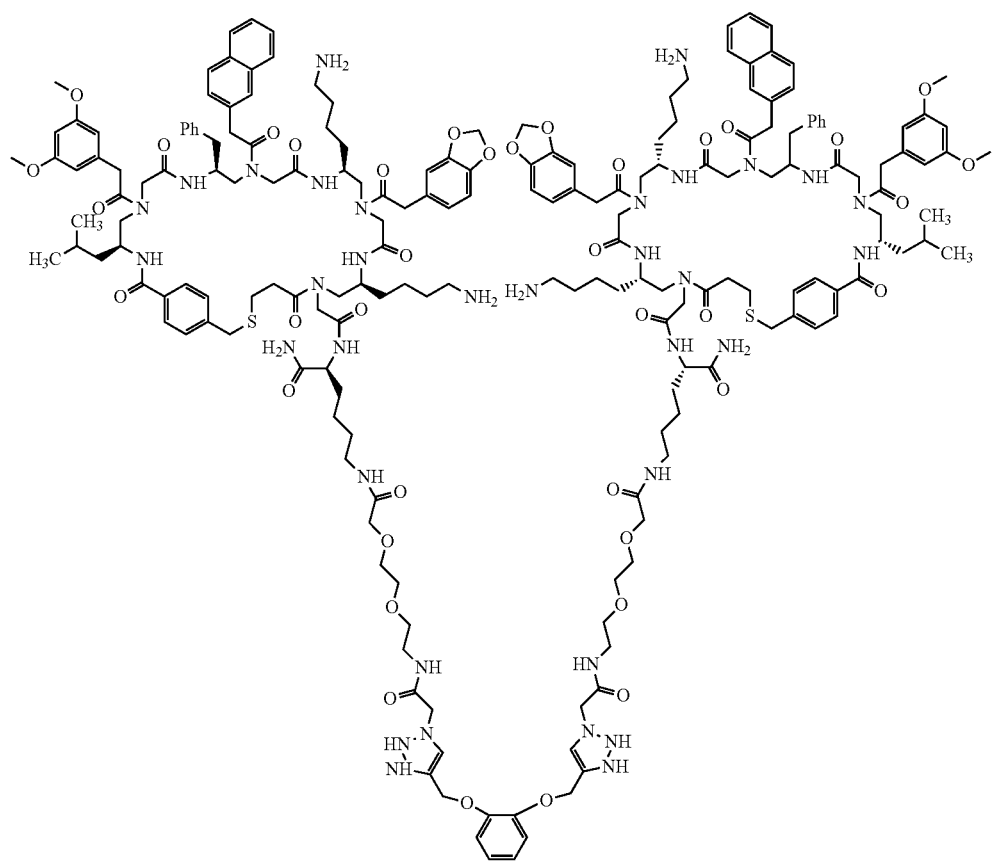

11. The compound of claim 1, wherein the compound binds to Her2 with a dissociation constant ($K_d$) of less than about 230 nM.

12. The compound of claim 10, wherein the compound binds to Her2 with a dissociation constant ($K_d$) of less than about 50 nM.

13. The compound of claim 1, wherein the compound binds to Her2 and prevents heterodimerization of Her2.

14. A pharmaceutical composition comprising a cyclic γ-amino acid peptide (cyclic γ-AA) selected from the compounds having the formula:

formula (i)
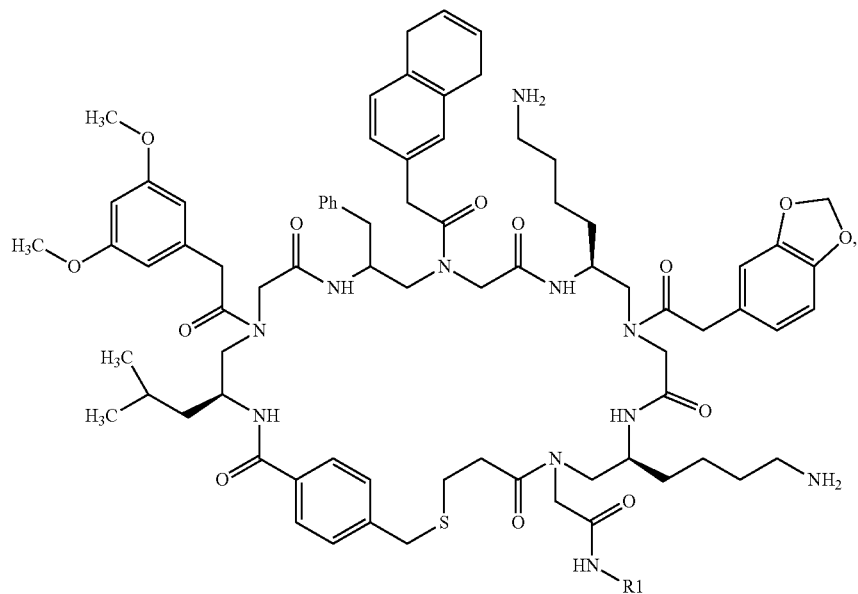
wherein R1
comprises H, a tag, a linker or a linker-tag complex,
formula (iii)
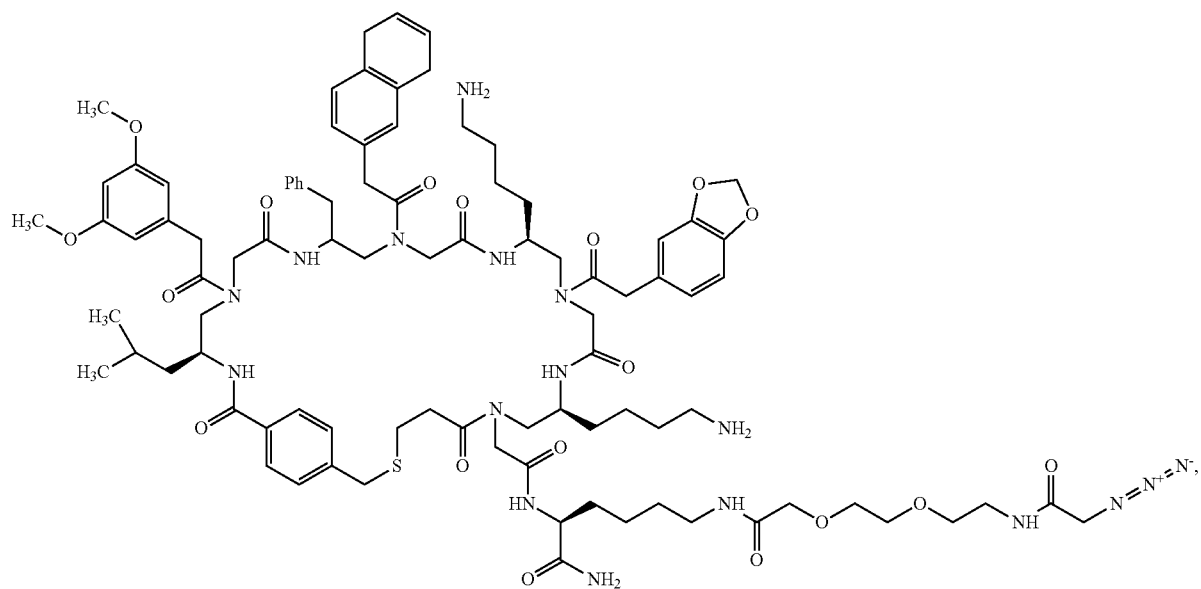

or formula (iv)

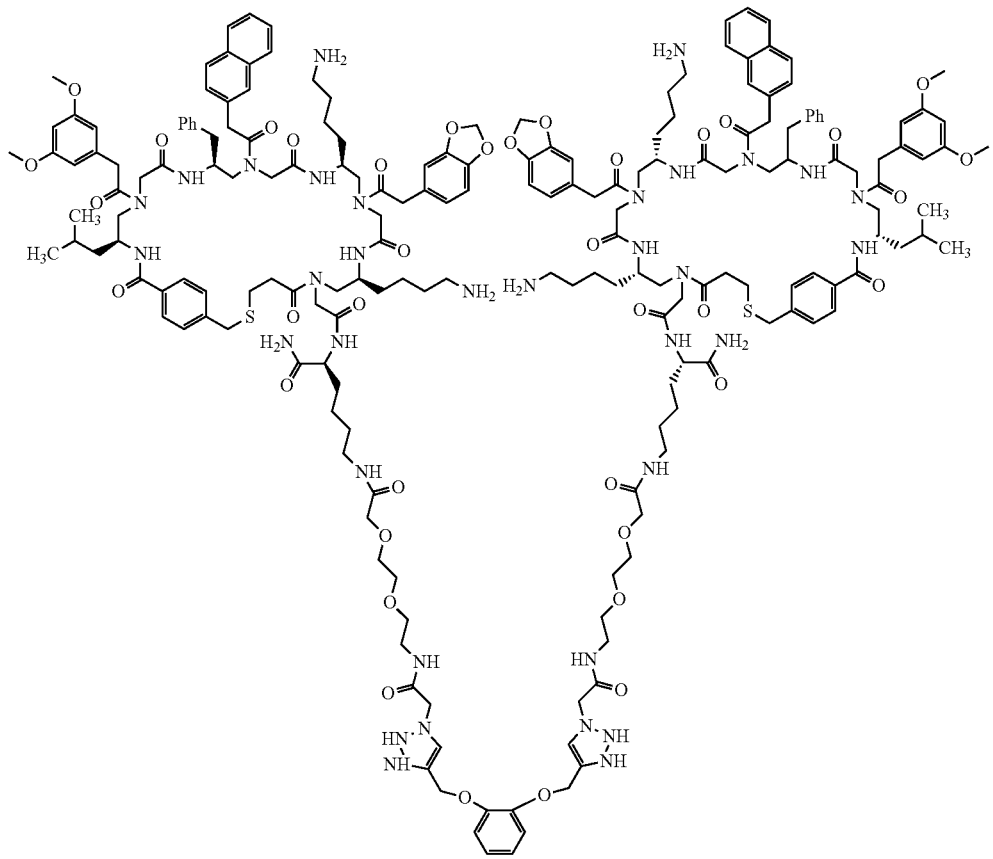

, and a pharmaceutically acceptable carrier.

15. A method of treating a cancer in a subject in need thereof, the method comprising: administering a therapeutically effective amount of the pharmaceutical composition of claim 14 to the subject to treat the cancer, wherein the cancer is characterized by the overexpression of Her2.

16. The method of claim 15, wherein the cancer is breast cancer.

17. The method of claim 15, wherein the method reduces the growth of the cancer in the subject.

18. The method of claim 15, wherein the method reduces phosphorylation of Her2, Erk, or Akt in the cancer.

19. The method of claim 15, wherein the method reduces proliferation of cancer cells in the subject.

20. The method of claim 15, wherein the cancer comprises a tumor and wherein the method reduces the volume of the tumor in the subject.

21. The method of claim 15, further comprising administering a therapeutically effective amount of an additional chemotherapeutic or immunotherapeutic agent to the subject.

22. A method of detecting Her2 in a sample from a subject suffering from a cancer suspected of expressing Her2 comprising:
i) contacting the sample with the cyclic γ-amino acid peptide compound of claim 1 to generate cyclic γ-amino acid peptide-Her2 complex,
ii) detecting the presence of the complex wherein the presence of the complex indicates the presence of Her2 in a sample from the subject.

23. The method of claim 22, further comprising
iii) administering a therapeutically effective amount of an anti-Her2 therapy.

24. A kit comprising:
i) the cyclic γ-amino acid peptide compound (cyclic γ-AA) of claim 1, and
ii) a detection reagent.

25. The kit of claim 24 further comprising:
iii) a solid support.

26. The kit of claim 25, wherein the solid support comprises a microplate, a lateral flow device, or a microfluidic device.

27. The kit of claim 24, wherein the cyclic γ-AA is formula (ii)
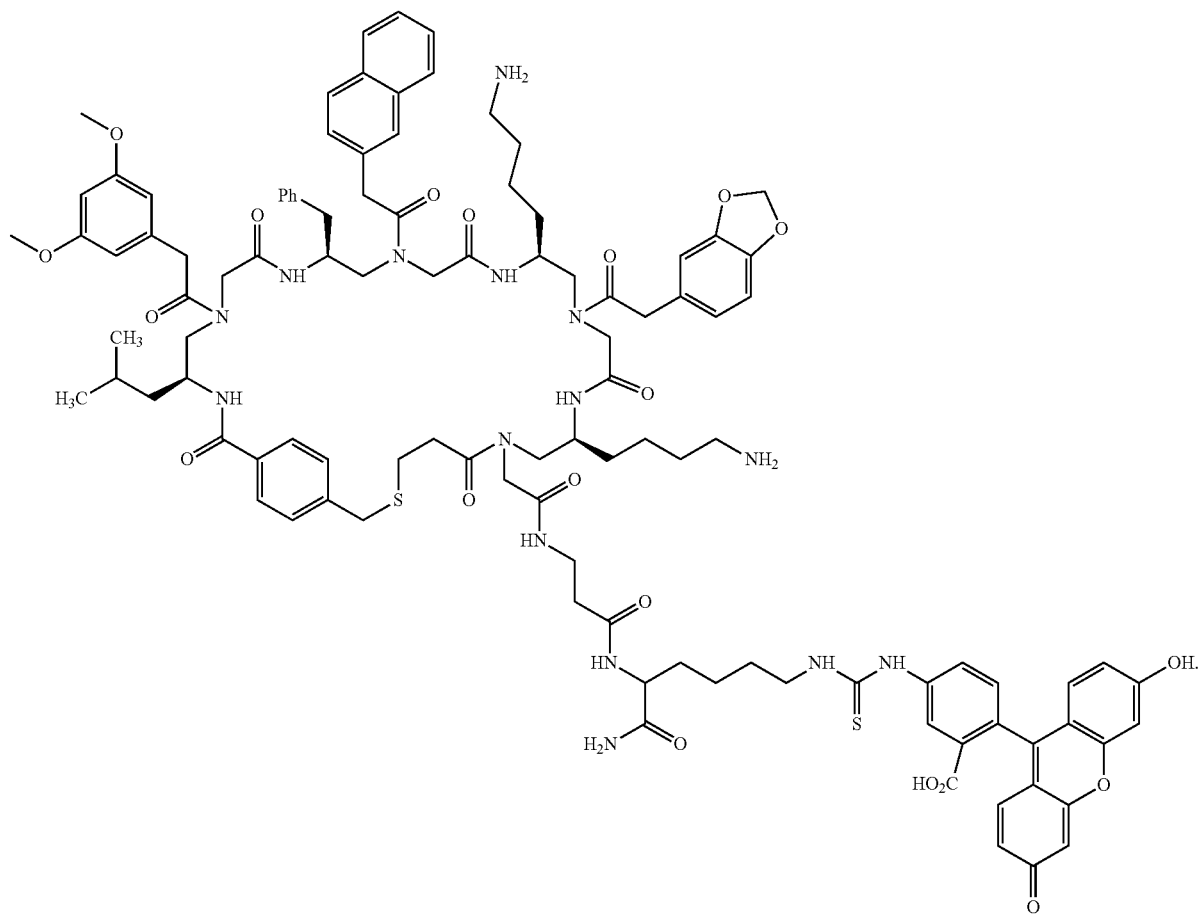 [SMILES: COc1cc(CC(=O)N2CC(=O)N[C@@H](Cc3ccccc3)CN(C(=O)Cc3ccc4ccccc4c3)CC(=O)N[C@@H](CCCCN)CN(C(=O)Cc3ccc4c(c3)OCO4)CC(=O)N[C@@H](CCCCN)CN(CC(=O)NCCC(=O)NC(CCCCNC(=S)Nc3ccc(-c4c5ccc(=O)cc-5oc5cc(O)ccc45)c(C(=O)O)c3)C(N)=O)C(=O)CCSCc3ccc(cc3)C(=O)N[C@@H](CC(C)C)C2)cc(OC)c1]
40
28. The kit of claim 24, wherein the detection reagent comprises a secondary antibody specific for the cyclic γ-AA.
29. A method comprising administering the pharmaceutical composition of claim 14 to a subject.
* * * * *